United States Patent
Önder et al.

(10) Patent No.: US 12,421,560 B2
(45) Date of Patent: Sep. 23, 2025

(54) ASSAYS FOR THE DETECTION OF SARS-COV-2 MUTANTS

(71) Applicant: Procomcure Biotech GmbH, Thalgau (AT)

(72) Inventors: Kamil Önder, Seekirchen am Wallersee (AT); Sven Breunig, Seekirchen am Wallersee (AT)

(73) Assignee: Procomcure Biotech GmbH, Thalgau (AT)

( * ) Notice: Subject to any disclaimer, the term of this patent is extended or adjusted under 35 U.S.C. 154(b) by 45 days.

(21) Appl. No.: 17/338,774

(22) Filed: Jun. 4, 2021

(65) Prior Publication Data

US 2022/0259679 A1    Aug. 18, 2022

(30) Foreign Application Priority Data

| Feb. 10, 2021 | (EP) | ................................... | 21156411 |
| Feb. 12, 2021 | (EP) | ................................... | 21156929 |
| Feb. 17, 2021 | (EP) | ................................... | 21157716 |
| Feb. 19, 2021 | (EP) | ................................... | 21158203 |
| May 7, 2021 | (EP) | ................................... | 21172801 |

(51) Int. Cl.

| *C12Q 1/68* | (2018.01) |
| *C12Q 1/6816* | (2018.01) |
| *C12Q 1/6827* | (2018.01) |
| *C12Q 1/686* | (2018.01) |
| *C12Q 1/6888* | (2018.01) |
| *C12Q 1/70* | (2006.01) |

(52) U.S. Cl.
CPC ......... *C12Q 1/6888* (2013.01); *C12Q 1/6816* (2013.01); *C12Q 1/6827* (2013.01); *C12Q 1/686* (2013.01); *C12Q 1/70* (2013.01); *C12Q 2600/156* (2013.01)

(58) Field of Classification Search
None
See application file for complete search history.

(56) References Cited

U.S. PATENT DOCUMENTS 7,109,312 B2 *  9/2006  Cook ..................... C07H 21/00
                                                       536/26.6

FOREIGN PATENT DOCUMENTS

| CN | 111304372 A | 6/2020 |
| CN | 111996290 A | 11/2020 |
| CN | 112063764 A | 12/2020 |

OTHER PUBLICATIONS

Ortuso et al., biorxiv, Sep. 9, 2020 (Year: 2020).*
Zimmer, TheScientist, Jan. 26, 2021 (Year: 2021).*
SNPsig SARS-CoV-2 (N501Y) kit handbook (Version1, 01, published Jan. 2, 2021) (Year: 2021).*
TaqMan SNP genotyping Assays (Life Technologies Corporation, 2014). (Year: 2014).*
Liu et al., 2006, Journal of Microbiological Methods, 65, 21-31 (Year: 2006).*
Farkas et al., "Large-scale population analysis of SARS-CoV-2 whole genome sequences reveals host-mediated viral evolution with emergence of mutations in the viral Spike protein associated with elevated mortality rates", med.Rxiv, Oct. 27, 2020, 50 pages. Retrieved from the Internet: https://www.medrxiy.org/content/10.110_1/2020.10.23.20218511v1.full.pdf.
International Search Report and Written Opinion, for PCT/EP2022.052927, dated Jul. 4, 2022, 29 pages.
Al-Jaf et al., "Rapid detection of SARS CoV-2 N501Y mutation in clinical samples", medRxiv, Apr. 20, 2021, 10 pages.
Anonymous, "SNPsig SARSCoV-2 (N501Y) kit handbook", Primerdesign Ltd., Feb. 1, 2021, 10 pages.
Durner et al., "Fast and cost-effective screening for SARS-CoV-2 variants in a routine diagnostic setting", Dental Materials, Elsevier, Amsterdam, NL, vol. 37, No. 3, Jan. 29, 2021, 3 pages.
Korukluoglu et al., "40 minutes RD-qPCR Assay for Screening Spike N501Y and HV69-70del Mutations", bioRxiv, Jan. 26, 2021, 17 pages.
Zimmer, Katarina "A Guide to Emerging SARS-CoV-2 Variants", The Scientist, Jan. 26, 2021, 7 pages.
Extended European Search Report, for Application No. 21172801.9-1118, dated Oct. 15, 2021, 12 pages.

* cited by examiner

*Primary Examiner* — Jehanne S Sitton
(74) *Attorney, Agent, or Firm* — Dority & Manning, P.A.

(57) ABSTRACT

An oligonucleotide, having a 5' terminus and a 3' terminus, wherein said oligonucleotide is detectably labeled and has a nucleotide sequence that consists essentially of one of the nucleotide sequences selected from SEQ ID NO:5, SEQ ID NO:6, SEQ ID NO:11, SEQ ID NO:12, SEQ ID NO:17, SEQ ID NO:18, SEQ ID NO:23, SEQ ID NO:24, SEQ ID NO:29, SEQ ID NO:30, SEQ ID NO:35, SEQ ID NO:36, SEQ ID NO:41, SEQ ID NO:42, SEQ ID NO:47, SEQ ID NO:48, SEQ ID NO:53, SEQ ID NO:54, SEQ ID NO:59 and SEQ ID NO:60.

16 Claims, 6 Drawing Sheets

Specification includes a Sequence Listing.

```
                        SEQUENCE LISTING

<160> NUMBER OF SEQ ID NOS: 76

<210> SEQ ID NO 1
<211> LENGTH: 63
<212> TYPE: DNA
<213> ORGANISM: Severe acute respiratory syndrome coronavirus 2

<400> SEQUENCE: 1
actttccttt acaatcatat ggtttccaac ccactaatgg tgttggttac caaccataca        60
gag                                                                     63

<210> SEQ ID NO 2
<211> LENGTH: 63
<212> TYPE: DNA
<213> ORGANISM: Severe acute respiratory syndrome coronavirus 2
<220> FEATURE:
<223> OTHER INFORMATION: Target sequence (A) mutant N501Y

<400> SEQUENCE: 2
actttccttt acaatcatat ggtttccaac ccacttatgg tgttggttac caaccataca        60
gag                                                                     63

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Forward Primer (A)

<400> SEQUENCE: 3
actttccttt acaatcatat gg                                                 22

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Reverse Primer (A)

<400> SEQUENCE: 4
ctctgtatgg ttggtaacc                                                     19

<210> SEQ ID NO 5
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      probe
<220> FEATURE:
<223> OTHER INFORMATION: Wildtype Probe (A)

<400> SEQUENCE: 5
tccaacccac taatggtg                                                  18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Mutant Probe (A)

<400> SEQUENCE: 6
tccaacccac ttatggtg                                                  18

<210> SEQ ID NO 7
<211> LENGTH: 82
<212> TYPE: DNA
<213> ORGANISM: Severe acute respiratory syndrome coronavirus 2

<400> SEQUENCE: 7
ctcaggactt gttcttacct ttcttttcca atgttacttg gttccatgct atacatgtct    60
ctgggaccaa tggtactaag ag                                             82

<210> SEQ ID NO 8
<211> LENGTH: 76
<212> TYPE: DNA
<213> ORGANISM: Severe acute respiratory syndrome coronavirus 2
<220> FEATURE:
<223> OTHER INFORMATION: Target Sequence (B) Mutant del HV69/70

<400> SEQUENCE: 8
ctcaggactt gttcttacct ttcttttcca atgttacttg gttccatgct atctctggga    60
ccaatggtac taagag                                                    76

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Forward Primer (B)

<400> SEQUENCE: 9
ctcaggactt gttcttacc                                                 19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Reverse Primer (B)

<400> SEQUENCE: 10
```

```
ctcttagtac cattggtcc                                                    19
```

```
<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Wildtype Probe (B)

<400> SEQUENCE: 11
tccatgctat acatgtctct                                                   20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Mutant Probe (B)

<400> SEQUENCE: 12
acttggttcc atgctatctc t                                                 21

<210> SEQ ID NO 13
<211> LENGTH: 72
<212> TYPE: DNA
<213> ORGANISM: Severe acute respiratory syndrome coronavirus 2

<400> SEQUENCE: 13
ccaggaacaa atacttctaa ccaggttgct gttctttatc aggatgttaa ctgcacagaa       60
gtccctgttg ct                                                           72

<210> SEQ ID NO 14
<211> LENGTH: 72
<212> TYPE: DNA
<213> ORGANISM: Severe acute respiratory syndrome coronavirus 2
<220> FEATURE:
<223> OTHER INFORMATION: Target Sequence (C) Mutant D614G

<400> SEQUENCE: 14
ccaggaacaa atacttctaa ccaggttgct gttctttatc agggtgttaa ctgcacagaa       60
gtccctgttg ct                                                           72

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Forward Primer (C)

<400> SEQUENCE: 15
ccaggaacaa atacttctaa cc                                                22

<210> SEQ ID NO 16
<211> LENGTH: 17
<212> TYPE: DNA
<213> ORGANISM: Artificial Sequence
<220> FEATURE:
```

<223> OTHER INFORMATION: Description of Artificial Sequence: Synthetic
      primer
<220> FEATURE:
<223> OTHER INFORMATION: Reverse Primer (C)

<400> SEQUENCE: 16
agcaacaggg acttctg 17

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Wildtype Probe (C)

<400> SEQUENCE: 17
tgttctttat caggatgtta actg 24

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Mutant Probe (C)

<400> SEQUENCE: 18
tgttctttat cagggtgtta act 23

<210> SEQ ID NO 19
<211> LENGTH: 74
<212> TYPE: DNA
<213> ORGANISM: Severe acute respiratory syndrome coronavirus 2

<400> SEQUENCE: 19
tcagacaaat cgctccaggg caaactggaa agattgctga ttataattat aaattaccag 60
atgattttac aggc 74

<210> SEQ ID NO 20
<211> LENGTH: 74
<212> TYPE: DNA
<213> ORGANISM: Severe acute respiratory syndrome coronavirus 2
<220> FEATURE:
<223> OTHER INFORMATION: Target Sequence (D) Mutant K417N

<400> SEQUENCE: 20
tcagacaaat cgctccaggg caaactggaa atattgctga ttataattat aaattaccag 60
atgattttac aggc 74

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Forward Primer (D)

<400> SEQUENCE: 21
tcagacaaat cgctcca 17

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Reverse Primer (D)

<400> SEQUENCE: 22
gcctgtaaaa tcatctggta                                                  20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Wildtype Probe (D)

<400> SEQUENCE: 23
caaactggaa agattgctg                                                   19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Mutant Probe (D)

<400> SEQUENCE: 24
caaactggaa atattgctg                                                   19

<210> SEQ ID NO 25
<211> LENGTH: 69
<212> TYPE: DNA
<213> ORGANISM: Severe acute respiratory syndrome coronavirus 2

<400> SEQUENCE: 25
aggtatatgc gctagttatc agactcagac taattctcct cggcgggcac gtagtgtagc      60
tagtcaatc                                                              69

<210> SEQ ID NO 26
<211> LENGTH: 69
<212> TYPE: DNA
<213> ORGANISM: Severe acute respiratory syndrome coronavirus 2
<220> FEATURE:
<223> OTHER INFORMATION: Target Sequence (E) Mutant P681H

<400> SEQUENCE: 26
aggtatatgc gctagttatc agactcagac taattctcat cggcgggcac gtagtgtagc      60
tagtcaatc                                                              69

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic

```
            primer
<220> FEATURE:
<223> OTHER INFORMATION: Forward Primer (E)

<400> SEQUENCE: 27
aggtatatgc gctagttatc aga                                          23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Reverse Primer (E)

<400> SEQUENCE: 28
gattgactag ctacactacg t                                            21

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Wildtype Probe (E)

<400> SEQUENCE: 29
actaattctc ctcggcg                                                 17

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Mutant Probe (E)

<400> SEQUENCE: 30
actaattctc atcggcg                                                 17

<210> SEQ ID NO 31
<211> LENGTH: 80
<212> TYPE: DNA
<213> ORGANISM: Severe acute respiratory syndrome coronavirus 2

<400> SEQUENCE: 31
cgcctattaa tttagtgcgt gatctccctc agggtttttc ggctttagaa ccattggtag   60
atttgccaat aggtattaac                                              80

<210> SEQ ID NO 32
<211> LENGTH: 80
<212> TYPE: DNA
<213> ORGANISM: Severe acute respiratory syndrome coronavirus 2
<220> FEATURE:
<223> OTHER INFORMATION: Target Sequence (F) Mutant A222V

<400> SEQUENCE: 32
cgcctattaa tttagtgcgt gatctccctc agggtttttc ggttttagaa ccattggtag   60
atttgccaat aggtattaac                                              80
```

```
<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Forward Primer (F)

<400> SEQUENCE: 33
cgcctattaa tttagtgcgt                                                    20

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Reverse Primer (F)

<400> SEQUENCE: 34
gttaatacct attggcaaat ctac                                               24

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Wildtype Probe (F)

<400> SEQUENCE: 35
agggtttttc ggctttagaa c                                                  21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Mutant Probe (F)

<400> SEQUENCE: 36
agggtttttc ggttttagaa c                                                  21

<210> SEQ ID NO 37
<211> LENGTH: 82
<212> TYPE: DNA
<213> ORGANISM: Severe acute respiratory syndrome coronavirus 2

<400> SEQUENCE: 37
agagagatat ttcaactgaa atctatcagg ccggtagcac accttgtaat ggtgttgaag        60
gttttaattg ttactttcct tt                                                 82

<210> SEQ ID NO 38
<211> LENGTH: 82
<212> TYPE: DNA
<213> ORGANISM: Severe acute respiratory syndrome coronavirus 2
<220> FEATURE:
<223> OTHER INFORMATION: Target Sequence (G) Mutant S477N
```

<400> SEQUENCE: 38
agagagatat tcaactgaa atctatcagg ccggtaacac accttgtaat ggtgttgaag    60
gttttaattg ttactttcct tt    82

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Forward Primer (G)

<400> SEQUENCE: 39
agagagatat ttcaactgaa atct    24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Reverse Primer (G)

<400> SEQUENCE: 40
aaaggaaagt aacaattaaa acct    24

<210> SEQ ID NO 41
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Wildtype Probe (G)

<400> SEQUENCE: 41
aggccggtag cacac    15

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Mutant Probe (G)

<400> SEQUENCE: 42
aggccggtaa cacac    15

<210> SEQ ID NO 43
<211> LENGTH: 78
<212> TYPE: DNA
<213> ORGANISM: Severe acute respiratory syndrome coronavirus 2

<400> SEQUENCE: 43
ccagatgttg atttaggtga catctctggc attaatgctt cagttgtaaa c

<210> SEQ ID NO 44
<211> LENGTH: 78
<212> TYPE: DNA
<213> ORGANISM: Severe acute respiratory syndrome coronavirus 2
<220> FEATURE:
<223> OTHER INFORMATION: Target Sequence (H) Mutant V1176F

<400> SEQUENCE: 44
ccagatgttg atttaggtga catctctggc attaatgctt catttgtaaa cattcaaaaa        60
gaaattgacc gcctcaat        78

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Forward Primer (H)

<400> SEQUENCE: 45
ccagatgttg atttaggtga c        21

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Reverse Primer (H)

<400> SEQUENCE: 46
attgaggcgg tcaatttc        18

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Wildtype Probe (H)

<400> SEQUENCE: 47
tggcattaat gcttcagttg taaa        24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Mutant Probe (H)

<400> SEQUENCE: 48
tggcattaat gcttcatttg taaa        24

<210> SEQ ID NO 49
<211> LENGTH: 77
<212> TYPE: DNA
<213> ORGANISM: Severe acute respiratory syndrome coronavirus 2

<400> SEQUENCE: 49 agatgattttt acaggctgcg ttatagcttg gaattctaac aatcttgatt ctaaggttgg    60
tggtaattat aattacc                                                   77

<210> SEQ ID NO 50
<211> LENGTH: 77
<212> TYPE: DNA
<213> ORGANISM: Severe acute respiratory syndrome coronavirus 2
<220> FEATURE:
<223> OTHER INFORMATION: Target Sequence (I) Mutant N439K

<400> SEQUENCE: 50 agatgattttt acaggctgcg ttatagcttg gaattctaaa aatcttgatt ctaaggttgg    60
tggtaattat aattacc                                                   77

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Forward Primer (I)

<400> SEQUENCE: 51 agatgattttt acaggctgc                                                19

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Reverse Primer (I)

<400> SEQUENCE: 52
ggtaattata attaccacca acct                                           24

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Wildtype Probe (I)

<400> SEQUENCE: 53
tagcttggaa ttctaacaat cttga                                          25

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Mutant Probe (I)

<400> SEQUENCE: 54

```
tagcttggaa ttctaaaaat cttga                                          25

<210> SEQ ID NO 55
<211> LENGTH: 94
<212> TYPE: DNA
<213> ORGANISM: Severe acute respiratory syndrome coronavirus 2

<400> SEQUENCE: 55
agagagatat ttcaactgaa atctatcagg ccggtagcac accttgtaat ggtgttgaag    60
gttttaattg ttactttcct ttacaatcat atgg                                94

<210> SEQ ID NO 56
<211> LENGTH: 94
<212> TYPE: DNA
<213> ORGANISM: Severe acute respiratory syndrome coronavirus 2
<220> FEATURE:
<223> OTHER INFORMATION: Target Sequence (J) Mutant E484K

<400> SEQUENCE: 56
agagagatat ttcaactgaa atctatcagg ccggtagcac accttgtaat ggtgttaaag    60
gttttaattg ttactttcct ttacaatcat atgg                                94

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Forward Primer (J)

<400> SEQUENCE: 57
agagagatat ttcaactgaa atct                                           24

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Reverse Primer (J)

<400> SEQUENCE: 58
ccatatgatt gtaaaggaaa gtaac                                          25

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Wildtype Probe (J)

<400> SEQUENCE: 59
ttgtaatggt gttgaaggtt tta                                            23

<210> SEQ ID NO 60
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: Mutant Probe (J)

<400> SEQUENCE: 60
ttgtaatggt gttaaaggtt tta                                              23

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 2019-nCoV_N1 forward primer

<400> SEQUENCE: 61 gacccccaaaa tcagcgaaat                                                 20

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 2019-n-CoV_N1 reverse primer

<400> SEQUENCE: 62
tctggttact gccagttgaa tctg                                             24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 2019-n-CoV_N1 reverse probe

<400> SEQUENCE: 63
accccgcatt acgtttggtg gacc                                             24

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 2019-nCoV_N2 forward primer

<400> SEQUENCE: 64
ttacaaacat tggccgcaaa                                                  20

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 2019-nCoV_N2 reverse primer
```

<400> SEQUENCE: 65
gcgcgacatt ccgaagaa                                                       18

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 2019-nCoV_N2 probe

<400> SEQUENCE: 66
acaatttgcc cccagcgctt cag                                                 23

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 2019-nCoV_N3 forward primer

<400> SEQUENCE: 67
gggagccttg aatacaccaa aa                                                  22

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 2019-nCoV_N3 reverse primer

<400> SEQUENCE: 68
tgtagcacga ttgcagcatt g                                                   21

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 2019-nCoV_N3 probe

<400> SEQUENCE: 69
aycacattgg cacccgcaat cctg                                                24

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: RNAse P forward primer

<400> SEQUENCE: 70
agatttggac ctgcgagcg                                                      19

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: RNAse P reverse primer

<400> SEQUENCE: 71
gagcggctgt ctccacaagt                                              20

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: RNAse P probe

<400> SEQUENCE: 72
ttctgacctg aaggctctgc gcg                                          23

<210> SEQ ID NO 73
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 4 bp shortened on 3' end compared to patented
      wildtype probe

<400> SEQUENCE: 73
tccaacccac ttat                                                    14

<210> SEQ ID NO 74
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 2 bp shortened on 3' end compared to patented
      wildtype probe

<400> SEQUENCE: 74
tccaacccac ttatgg                                                  16

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 2 bp lengthened on 3' end compared to patented
      wildtype probe

<400> SEQUENCE: 75
tccaacccac ttatggtgtt                                              20

```
<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 4 bp lengthened on 3' end compared to patented
      wildtype probe

<400> SEQUENCE: 76
tccaacccac ttatggtgtt gg                                          22
```

ASSAYS FOR THE DETECTION OF SARS-COV-2 MUTANTS

CROSS REFERENCE TO RELATED APPLICATIONS

This application claims priority to and the benefit of European Patent Application No. 21156411.7 filed in the European Patent Office on Feb. 10, 2021, European Patent Application No. 21156929.8 filed in the European Patent Office on Feb. 12, 2021, European Patent Application No. 21157716.8 filed in the European Patent Office on Feb. 17, 2021, European Patent Application No. 21558203.6 filed in the European Patent Office on Feb. 19, 2021, and European Patent Application No. 21172801.9 filed in the European Patent Office May 7, 2021, the entire contents of which are incorporated herein by reference.

SEQUENCE LISTING

This application contains a Sequence Listing which has been submitted electronically in ASCII format and is hereby incorporated by reference in its entirety. Said ASCII copy is named KSW-44_Sequence_List.txt, was created on Jul. 2, 2021, and is 20,861 bytes in size.

FIELD OF THE INVENTION

The present invention is directed to methods for assaying for the presence of SARS-CoV-2 and/or SARS-CoV-2 in a sample, including a clinical sample, and to oligonucleotides, reagents and kits useful in such assays. In particular, the present invention is directed to such assays that are rapid, accurate and specific for the detection of SARS-CoV-2 as well as its mutants.

BACKGROUND OF THE INVENTION

I. SARS-CoV-2

Severe Acute Respiratory Syndrome Coronavirus 2 (SARS-CoV-2) is a newly identified coronavirus species (the virus was previously provisionally named "2019 novel coronavirus" or "2019-nCoV"). SARS-CoV-2 infection is spread by human-to-human transmission via droplets or direct contact, and infection has been estimated to have a mean incubation period of 6.4 days and a Basic Reproduction Number of 2.24-3.58 (i.e., an epidemic doubling time of 6-8 days) (Fang, Y. et al. (2020) "Transmission Dynamics Of The COVID-19 Outbreak And Effectiveness Of Government Interventions: A Data-Driven Analysis," J. Med. Virol. doi: 10.1002/jmv.25750; Zhao, W. M. et al. (2020) "The 2019 Novel Coronavirus Resource," Yi Chuan. 42(2):212-221; Zhu, N. et al. (2020) "A Novel Coronavirus from Patients with Pneumonia in China, 2019," New Engl. J. Med. 382(8):727-733).

Patients infected with SARS-CoV-2 exhibit COVID-19, a condition initially characterized by fever and cough (Kong, I. et al. (2020) "Early Epidemiological and Clinical Characteristics of 28 Cases of Coronavirus Disease in South Korea," Osong Public Health Res Perspect. 11(1):8-14). In approximately 20% of patients, COVID-19 progresses to a severe respiratory disease and pneumonia that has a mortality of 5-10% (1-2% overall mortality).

Coronaviruses (CoVs) belong to the subfamily Orthocoronavirinae in the family Coronaviridae and the order Nidovirales. The Coronaviridae family of viruses are enveloped, single-stranded, RNA viruses that possess a positive-sense RNA genome of 26 to 32 kilobases in length. Four genera of coronaviruses have been identified, namely, Alphacoronavirus (αCoV), Betacoronavirus (βCoV), Deltacoronavirus (δCoV), and Gammacoronavirus (γCoV) (Chan, J. F. et al. (2013) "Interspecies Transmission And Emergence Of Novel Viruses: Lessons From Bats And Birds," Trends Microbiol. 21(10):544-555). Evolutionary analyses have shown that bats and rodents are the gene sources of most αCoVs and βCoVs, while avian species are the gene sources of most CoVs and γCoVs.

Prior to 2019, only six coronavirus species were known to be pathogenic to humans. Four of these species were associated with mild clinical symptoms, but two coronaviruses, Severe Acute Respiratory Syndrome (SARS) coronavirus (SARS-CoV) (Marra, M. A. et al. (2003) "The Genome Sequence of the SARS-Associated Coronavirus," Science 300(5624):1399-1404) and Middle East Respiratory Syndrome (MERS) coronavirus (MERS-CoV) (Mackay, I. M. (2015) "MERS Coronavirus: Diagnostics, Epidemiology And Transmission," Virol. J. 12:222. doi: 10.1186/s12985-015-0439-5) were associated with human mortalities approaching 10% (Su, S. et al. (2016) "Epidemiology, Genetic Recombination, And Pathogenesis Of Coronaviruses," Trends Microbiol. 24:490-502; Al Johani, S. et al. (2016) "MERS-CoV Diagnosis: An Update," J. Infect. Public Health 9(3):216-219).

SARS-CoV-2 is closely related (88%) to two bat-derived Severe Acute Respiratory Syndrome-like coronaviruses, bat-SL-CoVZC45 and bat-SL-CoVZXC21, and is more distantly related to SARS-CoV (79%) and MERS-CoV (50%) (Xie, C. et al. (2020) "Comparison Of Different Samples For 2019 Novel Coronavirus Detection By Nucleic Acid Amplification Tests" Int. J. Infect. Dis./doi.org/10.1016/j.ijid.2020.02.050; Mackay, I. M. (2015) "MERS Coronavirus: Diagnostics, Epidemiology And Transmission," Virol. J. 12:222. doi: 10.1186/s12985-015-0439-5; Gong, S. R. et al. (2018) "The Battle Against SARS And MERS Coronaviruses: Reservoirs And Animal Models," Animal Model Exp. Med. 1(2):125-133; Yin, Y. et al. (2018) "MERS, SARS And Other Coronaviruses As Causes Of Pneumonia," Respirology 23(2):130-137). Phylogenetic analysis revealed that SARS-CoV-2 fell within the subgenus Sarbecovirus of the genus Betacoronavirus, with a relatively long branch length to its closest relatives bat-SL-CoVZC45 and bat-SL-CoVZXC21, and was genetically distinct from SARS-CoV (Drosten et al. (2003) "Identification Of A Novel Coronavirus In Patients With Severe Acute Respiratory Syndrome," New Engl. J. Med. 348:1967-1976; Lai, C. C. et al. (2020) "Severe Acute Respiratory Syndrome Coronavirus 2 (SARS-CoV-2) And Coronavirus Disease-2019 (COVID-19): The Epidemic And The Challenges," Int. J. Antimicrob. Agents. 55(3):105924; Lu, R. et al. (2020) "Genomic Characterisation And Epidemiology Of 2019 Novel Coronavirus: Implications For Virus Origins And Receptor Binding," The Lancet 395(10224): 565-574; Zhou, Y. et al. (2020) "Network-Based Drug Repurposing For Novel Coronavirus 2019-nCoV/SARS-CoV-2," Cell Discov. 6(14): doi.org/10.1038/s41421-020-0153-3).

The SARS-CoV-2 genome has been sequenced from at least 170 isolates. The reference sequence is GenBank NC 045512 (Wang, C. et al. (2020) "The Establishment Of Reference Sequence For SARS-CoV-2 And Variation Analysis," J. Med. Virol. doi: 10.1002/jmv.25762; Chan, J. F. et al. (2020) "Genomic Characterization Of The 2019 Novel Human-Pathogenic Coronavirus Isolated From A Patient With Atypical Pneumonia After Visiting Wuhan," Emerg. Microbes. Infect. 9(1):221-236).

Comparisons of the sequences of multiple isolates of the virus (MN988668 and NC 045512, isolated from Wuhan, China, and MN938384.1, MN975262.1, MN985325.1, MN988713.1, MN994467.1, MN994468.1, and MN997409.1) reveal greater than 99.99% identity (Sah, R. et al. (2020) "Complete Genome Sequence of a 2019 Novel Coronavirus (SARS-CoV-2) Strain Isolated in Nepal," Microbiol. Resource Announcements 9(11): e00169-20, pages 1-3; Brussow, H. (2020) "The Novel Coronavirus-A Snapshot of Current Knowledge," Microbial Biotechnology 0:(0):1-6). The SARS-CoV-2 genome is highly similar to that of human SARS-CoV, with an overall nucleotide identity of approximately 82% (Chan, J. F. et al. (2020) "Genomic Characterization Of The 2019 Novel Human-Pathogenic Corona Virus Isolated From A Patient With Atypical Pneumonia After Visiting Wuhan," Emerg Microbes Infect 9:221-236; Chan, J. F. et al. (2020) "Improved Molecular Diagnosis Of COVID-19 By The Novel, Highly Sensitive And Specific COVID-19-RdRp/Hel Real-Time Reverse Transcription-Polymerase Chain Reaction Assay Validated In Vitro And With Clinical Specimens," J Clin. Microbiol. JCM.00310-20. doi: 10.1128/JCM.00310-20). Based on its homology to related coronaviruses, SARS-CoV-2 is predicted to encode 12 open reading frame (ORFs) coding regions (ORF1ab, S (spike protein), 3, E (envelope protein), M (matrix), 7, 8, 9, 10b, N, 13 and 14. The arrangement of these coding regions is shown in FIG. 1.

The S gene (spike gene) coding region is of particular significance to the present invention and has been characterised in the NCBI Genbank MN908947.

The S Gene

The S gene encodes the SARS-CoV-2 spike protein. The S protein of SARS-CoV is functionally cleaved into two subunits: the S1 domain and the S2 domain (He, Y. et al. (2004) "Receptor-Binding Domain Of SARS-CoV Spike Protein Induces Highly Potent Neutralizing Antibodies: Implication For Developing Subunit Vaccine," Biochem. Biophys. Res. Commun. 324:773-781). The SARS-CoV S1 domain mediates receptor binding, while the SARS-CoV S2 domain mediates membrane fusion (Li, F. (2016) "Structure, Function, And Evolution Of Coronavirus Spike Proteins," Annu. Rev. Virol. 3:237-261; He, Y. et al. (2004) "Receptor-Binding Domain Of SARS-CoV Spike Protein Induces Highly Potent Neutralizing Antibodies: Implication For Developing Subunit Vaccine, Biochem. Biophys. Res. Commun. 324:773-781). The S gene of SARS-CoV-2 may have a similar function. Thus, the spike protein of coronaviruses is considered crucial for determining host tropism and transmission capacity (Lu, G. et al. (2015) "Bat-To-Human: Spike Features Determining 'Host Jump' Of Coronaviruses SARS-CoV, MFRS-CoV, And Beyond," Trends Microbiol. 23:468-478; Wang, Q. et al. (2016) "MERS-CoV Spike Protein: Targets For Vaccines And Therapeutics," Antiviral. Res. 133:165-177). In this regard, the S2 domain of the SARS-CoV-2 spike protein shows high sequence identity (93%) with bat-SL-CoVZC45 and bat-SL-CoVZXC21, but the SARS-CoV-2 S1 domain shows a much lower degree of identity (68%) with these bat-derived viruses (Lu, R. et al. (2020) "Genomic Characterisation And Epidemiology Of 2019 Novel Coronavirus: Implications For Virus Origins And Receptor Binding," Lancet 395(10224):565-574). Thus, SARS-CoV-2 may bind to a different receptor than that bound by its related bat-derived viruses. It has been proposed that SARS-CoV-2 may bind to the angiotensin-converting enzyme 2 (ACE2) as a cell receptor (Lu, R. et al. (2020) "Genomic Characterisation And Epidemiology Of 2019 Novel Coronavirus: Implications For Virus Origins And Receptor Binding," Lancet 395(10224):565-574).

II. Assays for the Detection of SARS-CoV-2

SARS-CoV-2 was first identified in late 2019, and is believed to be a unique virus that had not previously existed. The first diagnostic test for SARS-CoV-2 used a real-time reverse transcription-PCR (rRT-PCR) assay that employed probes and primers of the SARS-CoV-2 E, N and nsp12 (RNA-dependent RNA polymerase; RdRp) genes (the "SARS-CoV-2-RdRp-P2" assay) (Corman, V. M. et al. (2020) "Detection Of 2019 Novel Coronavirus (2019-nCoV) By Real-Time RT-PCR," Eurosurveill. 25(3): 2000045; Spiteri, G. et al. (2020) "First Cases Of Coronavirus Disease 2019 (COVID-19) In The WHO European Region, 24 Jan. to 21 Feb. 2020," Eurosurveill. 25(9) doi: 10.2807/1560-7917.ES.2020.25.9.2000178).

The probes employed in such assays were "TaqMan" oligonucleotide probes that were labeled with a fluorophore on the oligonucleotide's 5' terminus and complexed with a quencher on the oligonucleotide's 3' terminus. The "TaqMan" probe principle relies on the 5"→3" exonuclease activity of Taq polymerase (Peake, I. (1989) "The Polymerase Chain Reaction," J. Clin. Pathol.; 42(7):673-676) to cleave the dual-labeled probe when it has hybridized to a complementary target sequence. The cleavage of the molecule separates the fluorophore from the quencher and thus leads to the production of a detectable fluorescent signal.

In the SARS-CoV-2-RdRp-P2 assay of Corman, V. M. et al. (2020), the RdRp Probe 2 and the probes of the E and N genes are described as being specific for SARS-CoV-2, whereas the RdRp Probe 2 is described as being a "PanSarbeco-Probe" that detects SARS-CoV and bat-SARS-related coronaviruses in addition to SARS-CoV-2. The assay is stated to have provided its best results using the E gene and nsp12 (RdRp) gene primers and probes (5.2 and 3.8 copies per 25 µL reaction at 95% detection probability, respectively). The resulting limit of detection (LoD) from replicate tests was 3.9 copies per 25 µL reaction (156 copies/mL) for the E gene assay and 3.6 copies per 25 µL reaction (144 copies/mL) for the nsp12 (RdRp) assay. The assay was reported to be specific for SARS-CoV-2 and to require less than 60 minutes to complete.

The US Center for Disease Control and Prevention (CDC) developed an rRT-PCR based assay protocol that targeted the SARS-CoV-2 N gene (Won, J. et al. (2020) "Development Of A Laboratory-Safe And Low-Cost Detection Protocol For SARS-CoV-2 Of The Coronavirus Disease 2019 (COVID-19)," Exp. Neurobiol. 29(2) doi: 10.5607/en20009).

Pfefferle, S. et al. (2020) ("Evaluation Of A Quantitative RT-PCR Assay For The Detection Of The Emerging Coronavirus SARS-CoV-2 Using A High Throughput System," Eurosurveill. 25(9) doi: 10.2807/1560-7917.ES.2020.25.9.2000152) discloses the use of a custom-made primer/probe set targeting the E gene. The employed primers were modified with 2'-O-methyl bases in their penultimate base to prevent formation of primer dimers. ZEN double-quenched probe (IDT) were used to lower background fluorescence. The LoD was 689.3 copies/mL with 275.72 copies per reaction at 95% detection probability. The assay was reported to be specific for SARS-CoV-2 and to require less than 60 minutes.

Chan, J. F. et al. (2020) ("Improved Molecular Diagnosis Of COVID-19 By The Novel, Highly Sensitive And Specific COVID-19-RdRp/Hel Real-Time Reverse Transcription-Polymerase Chain Reaction Assay Validated In Vitro And With Clinical Specimens," J. Clin. Microbiol. JCM.00310-20. doi: 10.1128/JCM.00310-20) explored the use of conserved and/or abundantly expressed SARS-CoV-2 genes as preferred targets of coronavirus RT-PCR assays. Such genes include the structural S and N genes, and the non-structural RdRp gene and ORF1ab. Chan, J. F. et al. (2020) describes the development of three real-time reverse transcriptase PCR (rRT-PCR) assays targeting the RNA-dependent RNA polymerase (RdRp)/helicase (Hel), spike (S), and nucleocapsid (N) genes of SARS-CoV-2 and compares such assays to the RdRp-P2 assay of Corman, V. M. et al. The LoD of the SARS-CoV-2-RdRp/Hel assay, the SARS-CoV-2-S assay, and the SARS-CoV-2-N assay was 1.8 TCID50/ml, while the LoD of the SARS-CoV-2-RdRp-P2 assay was 18 TCID50/ml. The TCID50 is the median tissue culture infectious dose.

An rt-PCR-based assay protocol targeting the E, N, S and RdRp genes was designed for specimen self-collection from a subject via pharyngeal swab. The assay required Trizol-based RNA purification, and detection was accomplished via an RT-PCR assay using SYBR Green as a detection fluor. The assay was reported to require approximately 4 hours to complete (Won, J. et al. (2020) ("Development Of A Laboratory-Safe And Low-Cost Detection Protocol For SARS-CoV-2 Of The Coronavirus Disease 2019 (COVID-19)," Exp. Neurobiol. 29(2) doi: 10.5607/en20009).

Although prior rRT-PCR assays, such as the SARS-CoV-2-RdRp-P2 assay of Corman V. M. et al., are capable of detecting SARS-CoV-2, researchers have found them to suffer from major deficiencies. In use, such prior assays have been found to require laborious batch-wise manual processing and to not permit random access to individual samples (Cordes, A. K. et al. (2020) "Rapid Random Access Detection Of The Novel SARS-Coronavirus-2 (SARS-CoV-2, Previously 2019-nCoV) Using An Open Access Protocol For The Panther Fusion," J. Clin. Virol. 125:104305 doi: 10.1016/j.jcv.2020.104305). Additionally, long turnaround times and complicated operations are required. These factors cause such assays to generally take more than 2-3 hours to generate results. Due to such factors, certified laboratories are required to process such assays. The need for expensive equipment and trained technicians to perform such prior rRT-PCR assays encumbers the use of such assays in the field or at mobile locations. Thus, researchers have found such prior assays to have limited suitability for use in the rapid and simple diagnosis and screening of patients required to contain an outbreak (Li, Z. et al. (2020) "Development and Clinical Application of A Rapid IgM-IgG Combined Antibody Test for SARS-CoV-2 Infection Diagnosis," J. Med. Virol. doi: 10.1002/jmv.25727).

More significantly, prior rRT-PCR assays, such as the SARS-CoV-2-RdRp-P2 assay of Corman V. M. et al., have been found to lack specificity for SARS-CoV-2 (cross-reacting with SARS-CoV or other pathogens) (Chan, J. F. et al. (2020) "Improved Molecular Diagnosis Of COVID-19 By The Novel, Highly Sensitive And Specific COVID-19-RdRp/Hel Real-Time Reverse Transcription-Polymerase Chain Reaction Assay Validated In Vitro And With Clinical Specimens," J. Clin. Microbiol. JCM.00310-20) and to provide a significant number of false negative results (Li, Z. et al. (2020) "Development and Clinical Application of A Rapid IgM-IgG Combined Antibody Test for SARS-CoV-2 Infection Diagnosis," J. Med. Virol. doi: 10.1002/jmv.25727).

For example, a retrospective analysis of 4880 clinically-identified COVID-19 patients. Samples obtained from the respiratory tracts of the patients were subjected to rRT-PCR amplification of the SARS-CoV-2 open reading frame 1ab (ORF1ab) and nucleocapsid protein (N) genes. Nasal and pharyngeal swabs of patients were evaluated for COVID-19 using a quantitative rRT-PCR (qRT-PCR) test. Only 38.42% (1875 of 4880) of actual COVID-19 patients were identified as positive using the rRT-PCR test. Of those testing positive, 39.80% were positive as determined by probes of the SARS-CoV-2 N gene and 40.98% were positive as determined by probes of the SARS-CoV-2 ORF1 ab (Liu, R. et al. (2020) "Positive Rate Of RT-PCR Detection Of SARS-CoV-2 Infection In 4880 Cases From One Hospital In Wuhan, China, From January To February 2020," Clinica Chimica Acta 505:172-175).

The study of Chan, J. F. et al. (2020) ("Improved Molecular Diagnosis Of COVID-19 By The Novel, Highly Sensitive And Specific COVID-19-RdRp/Hel Real-Time Reverse Transcription-Polymerase Chain Reaction Assay Validated In Vitro And With Clinical Specimens," J. Clin. Microbiol. JCM.00310-20. doi: 10.1128/JCM.00310-20) found that of 273 specimens from 15 patients with laboratory-confirmed COVID-19, only 28% were SARS-CoV-2 positive by both the SARS-CoV-2-RdRp/Hel and RdRp-P2 assays. The SARS-CoV-2-RdRp/Hel assay was more sensitive, but still confirmed only 43.6% of the patients as having SARS-CoV-2 infection.

In a different study, RNA was extracted from 1070 clinical samples of 205 patients suffering from COVID-19. Real-time reverse transcription-PCR (rRT-PCR) was then used to amplify SARS-CoV-2 ORF1ab in order to confirm the COVID-19 diagnosis (Wang, W. et al. (2020) ("Detection of SARS-CoV-2 in Different Types of Clinical Specimens," JAMA doi: 10.1001/jama.2020.3786). Bronchoalveolar lavage fluid specimens were reported to exhibit the highest positive rates (14 of 15; 93%), followed by sputum (72 of 104; 72%), nasal swabs (5 of 8; 63%), fibrobronchoscope brush biopsy (6 of 13; 46%), pharyngeal swabs (126 of 398; 32%), feces (44 of 153; 29%), and blood (3 of 307; 1%). None of the 72 urine specimens tested indicated a positive result. Thus, for example, pharyngeal swabs from such actual COVID-19 patients failed to accurately diagnose SARS-CoV-2 infection in 68% of those tested. Zhang, W. et al. (2020) ("Molecular And Serological Investigation Of 2019-nCoV Infected Patients: Implication Of Multiple Shedding Routes," Emerg. Microbes Infect. 9(1):386-389) also discloses the presence of SARS-CoV-2 in feces of COVID-19 patients, however, its rRT-PCR assay results showed more anal swab positives than oral swab positives in a later stage of infection, suggesting viral shedding and the capacity of the infection to be transmitted through an oral-fecal route. A similar teaching is provided by Tang, A. et al. (2020) ("Detection of Novel Coronavirus by RT-PCR in Stool Specimen from Asymptomatic Child, China," Emerg Infect Dis. 26(6). doi: 10.3201/eid2606.200301). This document discloses that RT-PCR assays targeting ORF1ab and nucleoprotein N gene failed to detect SARS-CoV-2 in nasopharyngeal swab and sputum samples, but were able to detect virus in stool samples.

In a further study of individuals suffering from COVID-19, repeated assays for SARS-CoV-2 were also found to report negative results (Wu, X. et al. (2020) ("Co-infection with SARS-CoV-2 and Influenza A Virus in Patient with Pneumonia, China," 26(6):pages 1-7. The publication teaches that existing assays for SARS-CoV-2 lack sufficient sensitivity, and thus lead to false negative diagnoses.

In light of the deficiencies encountered in using prior rRT-PCR assays, such as the SARS-CoV-2-RdRp-P2 assay of Corman V. M. et al., other approaches to assaying for SARS-CoV-2 have been explored. Li, Z. et al. (2020) ("Development and Clinical Application of A Rapid IgM-IgG Combined Antibody Test for SARS-CoV-2 Infection Diagnosis," J. Med. Virol. doi: 10.1002/jmv.25727) teaches that a point-of-care lateral flow immunoassay could be used to simultaneously detect anti-SARS-CoV-2 IgM and IgG antibodies in human blood and thus avoid the problems of the RdRp-P2 assay of Corman, V. M. et al. Immunoassays, however, may fail to discriminate between individuals suffering from COVID-19 and individuals who were previously infected with SARS-CoV-2, but have since recovered.

U.S. Pat. No. 10,815,539 B1 describes methods for assaying SARS-CoV-2 wildtype by using probes specifically hybridizing at the spike gene.

With the developing pandemic situation worldwide several mutants of the SARS-CoV-2 wildtype appeared (Preliminary genomic characterisation of an emergent SARS-CoV-2 lineage in the UK defined by a novel set of spike mutations—SARS-CoV-2 coronavirus/nCoV-2019 Genomic Epidemiology—Virological) with different and partly higher contagious rates.).

Most of the mutants which could be identified so far are genetic variations of the spike gene of the SARS-CoV-2 wildtype (NCBI Genbank MN908947).

In particular the genetic variation of the spike gene of SARS-CoV-2 which are selected from the group consisting of A23063T, de121765-770, A23403G, G22813T, C23604A, C22227T, G22992A, G25088T, C22879A and G23012A are widely spread and developing fast.

Due to the rapid development of some of the mutants in certain areas mutants may become the dominating SARS-CoV-2 infection source in some populations. Mutants of SARS-CoV-2 may require different treatments or vaccination of humans.

G. Korukluoglu, et al. describes in bioRxiv preprint doi: https://doi.org/10.1101/2021.01.26.428302 methods for assaying N501Y and HV69-70del mutations at the spike gene of SARS-CoV-2. The used forward primer show a CTT at the 3'end. However, with this CTT end no effective binding can be established. The labeled probe and the reverse primer can always bind as they are outside the SNP. The forward primer have the mismatch at the 3'end which leads to no polymerase reaction with the consequence that no signal can be observed in case of presence of a mutant or there is only a signal observed if the last base at the 3'end of the forward primer fits to the mutant.

Thus, a demand for the rapid discrimination of the SARS-CoV-2 wildtype and the respective mutants thereof exists. This requires a high specificity of the method to distinguish between the wildtype form and the genetic variation.

The present invention is advantageous over the prior art as the mismatch is located in the probes and consequently the method of the present invention leads to PCR products of the same lengths with the mutation in the middle area. The prior art obtains a PCR product only if there is a fit, thus with a suitable allele. Furthermore, the advantage of the present invention is that it can be simultaneously distinguished between a wildtype and a mutant or even among different mutants.

SUMMARY OF THE INVENTION

The specific Sequence ID No to which it is referred to in the following are reflected in Table 1 to 10 and Table A and Aa as well as the sequence listing which forms full part of the present invention.

For various genetic variations of the SARS-CoV-2 wildtype specific systems which can be used for the specific mutants are reflected in Table 1 to 10.

The present invention is directed to methods for assaying for the presence of mutants of SARS-CoV-2 in a sample, including a clinical sample, and to oligonucleotides, reagents and kits useful in such assays. In particular, the present invention is directed to such assays that are rapid, accurate and specific for the detection of SARS-CoV-2 mutants as well as the discrimination of SARS-CoV-2 wildtype and mutants of SARS-CoV-2.

One embodiment of the present invention provides an oligonucleotide, having a 5' terminus and a 3' terminus, wherein the oligonucleotide has a nucleotide sequence that consists essentially of the nucleotide sequence that consists of, consists essentially of, or is a variant of, the nucleotide sequence selected from the group consisting of SEQ ID NO:5, SEQ ID NO:6, SEQ ID NO:11, SEQ ID NO:12, SEQ ID NO:17, SEQ ID NO:18, SEQ ID NO:23, SEQ ID NO:24, SEQ ID NO:29, SEQ ID NO:30, SEQ ID NO:35, SEQ ID NO:36, SEQ ID NO:41, SEQ ID NO:42, SEQ ID NO:47, SEQ ID NO:48, SEQ ID NO:53, SEQ ID NO:54, SEQ ID NO:59 and SEQ ID NO:60.

One embodiment of the invention is a nucleotide consisting of SEQ ID NO:5.

One embodiment of the invention is a nucleotide consisting of SEQ ID NO:6.

One embodiment of the invention is a nucleotide consisting of SEQ ID NO:11.

One embodiment of the invention is a nucleotide consisting of SEQ ID NO:12.

One embodiment of the invention is a nucleotide consisting of SEQ ID NO:17.

One embodiment of the invention is a nucleotide consisting of SEQ ID NO:18.

One embodiment of the invention is a nucleotide consisting of SEQ ID NO:23.

One embodiment of the invention is a nucleotide consisting of SEQ ID NO:24.

One embodiment of the invention is a nucleotide consisting of SEQ ID NO:29.

One embodiment of the invention is a nucleotide consisting of SEQ ID NO:30.

One embodiment of the invention is a nucleotide consisting of SEQ ID NO:35.

One embodiment of the invention is a nucleotide consisting of SEQ ID NO:36.

One embodiment of the invention is a nucleotide consisting of SEQ ID NO:41.

One embodiment of the invention is a nucleotide consisting of SEQ ID NO:42.

One embodiment of the invention is a nucleotide consisting of SEQ ID NO:47.

One embodiment of the invention is a nucleotide consisting of SEQ ID NO:48.

One embodiment of the invention is a nucleotide consisting of SEQ ID NO:53.

One embodiment of the invention is a nucleotide consisting of SEQ ID NO:54.

One embodiment of the invention is a nucleotide consisting of SEQ ID NO:59.

One embodiment of the invention is a nucleotide consisting of SEQ ID NO:60.

One aspect of the invention is an oligonucleotide, having a 5' terminus and a 3' terminus, wherein said oligonucleotide is detectably labeled and has a nucleotide sequence that consists essentially of one of the nucleotide sequences selected from SEQ ID NO:6 and SEQ ID NO:60 and SEQ ID NO: 24.

The oligonucleotides form the basis for specifically designed probes which can preferably be used in PCR methods to detect SARS-CoV-2 wildtype virus or mutants thereof.

A further embodiment of the invention is an oligonucleotide, having a 5' terminus and a 3' terminus, wherein said oligonucleotide is detectably labeled and has a nucleotide sequence that consists or consists essentially of one of the nucleotide sequences selected from SEQ ID NO:5, SEQ ID NO:6, SEQ ID NO:11, SEQ ID NO:12, SEQ ID NO:17, SEQ ID NO:18, SEQ ID NO:23, SEQ ID NO:24, SEQ ID NO:29, SEQ ID NO:30, SEQ ID NO:35, SEQ ID NO:36, SEQ ID NO:41, SEQ ID NO:42, SEQ ID NO:47, SEQ ID NO:48, SEQ ID NO:53, SEQ ID NO:54, SEQ ID NO:59 and SEQ ID NO:60.

In a preferred aspect of the invention said oligonucleotide is a probe of SARS-CoV-2 wild type said probe having a nucleotide sequence that consists essentially of one of the nucleotide sequences selected from SEQ ID NO:5, SEQ ID NO:11, SEQ ID NO:17, SEQ ID NO:23, SEQ ID NO:29, SEQ ID NO:35, SEQ ID NO:41, SEQ ID NO:47, SEQ ID NO:53 and SEQ ID NO:59.

In a further preferred aspect of the invention said oligonucleotide is a Mutant probe of SARS-CoV-2 said probe having a nucleotide sequence that consists essentially of one of the nucleotide sequences selected from SEQ ID NO:6, SEQ ID NO:12, SEQ ID NO:18, SEQ ID NO:24, SEQ ID NO:30, SEQ ID NO:36, SEQ ID NO:42, SEQ ID NO:48, SEQ ID NO:54 and SEQ ID NO:60, preferably selected from SEQ ID NO:6 and SEQ ID NO:60 and SEQ ID NO: 24.

Preferably the oligonucleotide of the invention has a 5' terminus that is labeled with a fluorophore and a 3' terminus that is connected or complexed to a quencher of fluorescence of said fluorophore.

Preferably said quencher quenches fluorescent signals of 480-580 nm.

In a further preferred aspect said fluorophore has an excitation wavelength in the range of about 352-538 nm and an emission wavelength in the range of about 447-559 nm.

In a further preferred aspect of the invention the oligonucleotide of the invention has a quencher which is a black hole quencher 1 (BHQ1), preferably comprising or consisting of a moiety of 4'-(2-Nitro-4-toluyldiazo)-2'-methoxy-5'-methyl-azobenzene-4"-(N-ethyl)-N-ethyl.

According to a preferred embodiment the oligonucleotide has a 5' terminus that is labeled with a 5-carboxyfluorescein (5-FAM") or 6-carboxyfluorescein (6-FAM) or mixtures thereof (FAM) and a 3' terminus that is connected or complexed to a quencher of fluorescence of said fluorophore.

In a further preferred aspect the oligonucleotide has a 5' terminus that is labeled with Hexachlorofluorescein (HEX) and a 3' terminus that is connected or complexed to a quencher of fluorescence of said fluorophore.

In a particular preferred embodiment of the invention the oligonucleotide is a probe of SARS-CoV-2 wild type said probe having a nucleotide sequence that consists or consists essentially of one of the nucleotide sequences selected from SEQ ID NO:5, SEQ ID NO:11, SEQ ID NO:17, SEQ ID NO:23, SEQ ID NO:29, SEQ ID NO:35, SEQ ID NO:41, SEQ ID NO:47, SEQ ID NO:53 and SEQ ID NO:59; and wherein said oligonucleotide has a 5' terminus that is labeled with a 5-carboxyfluorescein (5-FAM") or 6-carboxyfluorescein (6-FAM) or mixtures thereof (FAM) and a 3' terminus that is connected or complexed to a quencher wherein said quencher is preferably a black hole quencher 1 (BHQ1), more preferably comprising or consisting of a moiety of 4'-(2-Nitro-4-toluyldiazo)-2'-methoxy-5'-methyl-azobenzene-4"-(N-ethyl)-N-ethyl.

In a further aspect the oligonucleotide of the invention is a mutant probe of SARS-CoV-2 said probe having a nucleotide sequence that consists essentially of one of the nucleotide sequences selected from SEQ ID NO:6 and SEQ ID NO:60 and SEQ ID NO:24; and wherein said oligonucleotide has a 5' terminus that is labeled with Hexachlorofluorescein (HEX) and a 3' terminus that is connected or complexed to a quencher wherein said quencher is preferably a black hole quencher 1 (BHQ1), more preferably comprising or consisting of a moiety of 4'-(2-Nitro-4-toluyldiazo)-2'-methoxy-5'-methyl-azobenzene-4"-(N-ethyl)-N-ethyl.

In another preferred embodiment of the invention the oligonucleotide of the invention is a mutant probe of SARS-CoV-2 said probe having a nucleotide sequence that consists or consists essentially of one of the nucleotide sequences selected from SEQ ID NO:6, SEQ ID NO:12, SEQ ID NO:18, SEQ ID NO:24, SEQ ID NO:30, SEQ ID NO:36, SEQ ID NO:42, SEQ ID NO:48, SEQ ID NO:54 and SEQ ID NO:60; and wherein said oligonucleotide has a 5' terminus that is labeled with Hexachlorofluorescein (HEX) and a 3' terminus that is connected or complexed to a quencher wherein said quencher is preferably a black hole quencher 1 (BHQ1), more preferably comprising or consisting of a moiety of 4'-(2-Nitro-4-toluyldiazo)-2'-methoxy-5'-methyl-azobenzene-4"-(N-ethyl)-N-ethyl.

The present invention can be used to specifically identify or detect mutants of the SARS-CoV-2 wildtype. Especially genetic variants of the spike gene of the SARS-CoV-2 can be detected. Therefore, another embodiment of the present invention is a method for detecting the presence of a genetic variation (mutant) of SARS-CoV-2 wildtype in a sample, wherein said method comprises 1) contacting a sample with
   a) amplification primers specifically hybridizing to a target sequence selected from oligonucleotides comprising the genetic variation of the spike gene of SARS-CoV-2 or a fragment thereof comprising said genetic variation;
   b) a mutant probe said mutant probe being a detectably labeled oligonucleotide that is able to specifically hybridize to the genetic variation of the spike gene of SARS-CoV-2 or a fragment thereof, wherein said mutant probe is preferably labeled with a fluorophore and a quencher of fluorescence of said fluorophore,
2) performing a primer extension reaction; and
3) determining whether the genetic variation of the spike gene of SARS-CoV-2 or a fragment thereof is present in said sample, preferably by determining whether a fluorescent signal of said fluorophore has become detectable.

Specifically the method of the present invention allows for the detection of the genetic variation of the spike gene of SARS-CoV-2 selected from the group consisting of A23063T, del21765-770, A23403G, G22813T, C23604A, C22227T, G22992A, G25088T, C22879A and G23012A.

A further aspect of the method of the invention is a method for detecting the presence of a genetic variation (mutant) of SARS-CoV-2 wildtype in a sample, wherein the genetic variation of the spike gene of SARS-CoV-2 is selected from the group consisting of A23063T and/or G23012A and optionally G22813T, preferably selected from the consisting A23063T, G23012A and G22813T, wherein said method comprises
1) contacting a sample with
    a) amplification primers specifically hybridizing to a target sequence selected from oligonucleotides comprising said genetic variation of the spike gene of SARS-CoV-2 or a fragment thereof comprising said genetic variation;
   b) mutant probe(s) having a nucleotide sequence that consists essentially of the nucleotide sequences SEQ ID NO:6 and/or SEQ ID NO:60 and optionally SEQ ID NO: 24, preferably mutant probes different from each other and having the nucleotide sequences SEQ ID NO:6, SEQ ID NO:60 and SEQ ID NO: 24, said mutant probe being a detectably labeled oligonucleotide that is able to specifically hybridize to said genetic variation of the spike gene of SARS-CoV-2 or a fragment thereof, wherein said mutant probe is preferably labeled with a fluorophore and a quencher of fluorescence of said fluorophore,
2) performing a primer extension reaction; and
3) determining whether said genetic variation of the spike gene of SARS-CoV-2 or a fragment thereof is present in said sample, preferably by determining whether a fluorescent signal of said fluorophore has become detectable.

The spike gene of the wildtype is reflected in NCBI Genbank MN908947.

In a preferred embodiment of the method the oligonucleotides of the target sequence comprising the genetic variation comprise or are consisting or are a variant of one of SEQ ID NO:2, SEQ ID NO:8, SEQ ID NO:14, SEQ ID NO:20, SEQ ID NO:26, SEQ ID NO:32, SEQ ID NO:38, SEQ ID NO:44, SEQ ID NO:50 and SEQ ID NO:56.

In one aspect of the invention the oligonucleotides of the target sequence comprising the genetic variation comprise or are consisting of one of SEQ ID NO:2 and SEQ ID NO:56 and optionally SEQ ID NO:20.

According to a specifically preferred aspect of the method of the present invention the oligonucleotides of the mutant probes are selected from the group consisting of SEQ ID NO:6, SEQ ID NO:12, SEQ ID NO:18, SEQ ID NO:24, SEQ ID NO:30, SEQ ID NO:36, SEQ ID NO:42, SEQ ID NO:48, SEQ ID NO:54 and SEQ ID NO:60, especially selected from SEQ ID NO:6, SEQ ID NO:24 and SEQ ID NO:60.

A further preferred embodiment of the method of the invention is a method for detecting the presence of a genetic variation (mutant) of SARS-CoV-2 wildtype in a sample, wherein said method comprises 1) contacting a sample with
   a) amplification primers specifically hybridizing to a target sequence selected from the group comprising or consisting of or a variant of one of SEQ ID NO:2, SEQ ID NO:8, SEQ ID NO:14, SEQ ID NO:20, SEQ ID NO:26, SEQ ID NO:32, SEQ ID NO:38, SEQ ID NO:44, SEQ ID NO:50 and SEQ ID NO:56;
   b) a mutant probe said mutant probe being a detectably labeled oligonucleotide that is able to specifically hybridize to the genetic variation of the spike gene of SARS-CoV-2 or a fragment thereof, wherein said mutant probe is labeled with a fluorophore and a quencher of fluorescence of said fluorophore, and wherein the oligonucleotides of the mutant probe are selected from the group comprising or consisting of SEQ ID NO:6, SEQ ID NO:12, SEQ ID NO:18, SEQ ID NO:24, SEQ ID NO:30, SEQ ID NO:36, SEQ ID NO:42, SEQ ID NO:48, SEQ ID NO:54 and SEQ ID NO:60;
2) performing a primer extension reaction; and
3) determining whether the genetic variation of the spike gene of SARS-CoV-2 or a fragment thereof is present in said sample by determining whether a fluorescent signal of said fluorophore has become detectable, wherein
   i) presence of the target sequence SEQ ID NO:2 or presence of said sequence within the nucleotide sequences of the sample; and use of a mutant probe having an oligonucleotide consisting of SEQ ID NO:6 indicates the genetic variation A23063T;
   ii) presence of the target sequence SEQ ID NO:8 or presence of said sequence within the nucleotide sequences of the sample; and use of a mutant probe having an oligonucleotide consisting of SEQ ID NO:12 indicates the genetic variation del21765-770;
   iii) presence of the target sequence SEQ ID NO:14 or presence of said sequence within the nucleotide sequences of the sample; and use of a mutant probe having an oligonucleotide consisting of SEQ ID NO:18 indicates the genetic variation A23403G;
   iv) presence of the target sequence SEQ ID NO:20 or presence of said sequence within the nucleotide sequences of the sample; and use of a mutant probe having an oligonucleotide consisting of SEQ ID NO:24 indicates the genetic variation G22813T;
   v) presence of the target sequence SEQ ID NO:26 or presence of said sequence within the nucleotide sequences of the sample; and use of a mutant probe having an oligonucleotide consisting of SEQ ID NO:30 indicates the genetic variation C23604A;
   vi) presence of the target sequence SEQ ID NO:32 or presence of said sequence within the nucleotide sequences of the sample; and use of a mutant probe having an oligonucleotide consisting of SEQ ID NO:36 indicates the genetic variation C22227T;
   vii) presence of the target sequence SEQ ID NO:38 or presence of said sequence within the nucleotide sequences of the sample; and use of a mutant probe having an oligonucleotide consisting of SEQ ID NO:42 indicates the genetic variation G22992A;
   viii) presence of the target sequence SEQ ID NO:44 or presence of said sequence within the nucleotide sequences of the sample; and use of a mutant probe having an oligonucleotide consisting of SEQ ID NO:48 indicates the genetic variation G25088T;
   ix) presence of the target sequence SEQ ID NO:50 or presence of said sequence within the nucleotide sequences of the sample; and use of a mutant probe having an oligonucleotide consisting of SEQ ID NO:54 indicates the genetic variation C22879A; and
   x) presence of the target sequence SEQ ID NO:56 or presence of said sequence within the nucleotide sequences of the sample; and use of a mutant probe having an oligonucleotide consisting of SEQ ID NO:60 indicates the genetic variation G23012A.

A especially preferred method of the invention comprises 1) contacting a sample with
   a) amplification primers specifically hybridizing to a target sequence selected from the group consisting of one of SEQ ID NO:2 or SEQ ID NO:56 or optionally SEQ ID NO: 20;
   b) a mutant probe said mutant probe being a detectably labeled oligonucleotide that is able to specifically hybridize to the genetic variation of the spike gene of SARS-CoV-2 or a fragment thereof, wherein said mutant probe is labeled with a fluorophore and a quencher of fluorescence of said fluorophore, and wherein the oligonucleotides of the mutant probe are selected from the group consisting of SEQ ID NO:6 and/or SEQ ID NO:60 and optionally SEQ ID NO:24, preferably selected from SEQ ID NO:6, SEQ ID NO:60 and SEQ ID NO:24;

2) performing a primer extension reaction; and
3) determining whether the genetic variation of the spike gene of SARS-CoV-2 or a fragment thereof is present in said sample by determining whether a fluorescent signal of said fluorophore has become detectable, wherein
   i) presence of the target sequence SEQ ID NO:2 or presence of said sequence within the nucleotide sequences of the sample; and use of a mutant probe having an oligonucleotide consisting of SEQ ID NO:6 indicates the genetic variation A23063T; and
   ii) presence of the target sequence SEQ ID NO:56 or presence of said sequence within the nucleotide sequences of the sample; and use of a mutant probe having an oligonucleotide consisting of SEQ ID NO:60 indicates the genetic variation G23012A; and
   ii) presence of the target sequence SEQ ID NO:20 or presence of said sequence within the nucleotide sequences of the sample; and use of a mutant probe having an oligonucleotide consisting of SEQ ID NO:24 indicates the genetic variation G22813T.

A further embodiment of the present invention provides for a method a for detecting the presence of the genetic variation A23063T of the spike gene of SARS-CoV-2 wildtype in a sample, wherein said method comprises
   1) contacting a sample with
      a) Forward Primer (A) comprising or consisting of an oligonucleotide having SEQ ID NO: 3,
      b) Reverse Primer (A) comprising or consisting of an oligonucleotide having SEQ ID NO: 4; and
      c) a mutant probe (A) comprising or consisting of or a variant of an oligonucleotide of SEQ ID NO:6 said mutant probe (A) being a detectably labeled oligonucleotide that is able to specifically hybridize to a target sequence (A) having a nucleotide sequence that comprises or consists essentially of SEQ ID NO:2; and
      wherein said mutant probe (A) oligonucleotide is preferably labeled with a fluorophore and a quencher of fluorescence of said fluorophore;
   2) performing a primer extension reaction; and
   3) determining whether the genetic variation A23063T is present in said sample, preferably by determining whether a fluorescent signal of said fluorophore has become detectable.

A further embodiment of the present invention provides for a method for detecting the presence of the genetic variation del21765-770 of the spike gene of SARS-CoV-2 wildtype in a sample, wherein said method comprises
   1) contacting a sample with
      a) Forward Primer (B) comprising or consisting of an oligonucleotide having SEQ ID NO: 9,
      b) Reverse Primer (B) comprising or consisting of an oligonucleotide having SEQ ID NO: 10; and
      c) a mutant probe (B) comprising or consisting of or a variant of an oligonucleotide of SEQ ID NO:12 said mutant probe (B) being a detectably labeled oligonucleotide that is able to specifically hybridize to a target sequence (B) having a nucleotide sequence that comprises or consists essentially of SEQ ID NO:8; and
      wherein said mutant probe (B) oligonucleotide is preferably labeled with a fluorophore and a quencher of fluorescence of said fluorophore;
   2) performing a primer extension reaction; and
   3) determining whether the genetic variation del21765-770 is present in said sample, preferably by determining whether a fluorescent signal of said fluorophore has become detectable.

A further embodiment of the present invention provides for a method for detecting the presence of the genetic variation A23403G of the spike gene of SARS-CoV-2 wildtype in a sample, wherein said method comprises
   1) contacting a sample with
      a) Forward Primer (C) comprising or consisting of an oligonucleotide having SEQ ID NO: 15,
      b) Reverse Primer (C) comprising or consisting of an oligonucleotide having SEQ ID NO: 16; and
      c) a mutant probe (C) comprising or consisting of or a variant of an oligonucleotide of SEQ ID NO:18 said mutant probe (C) being a detectably labeled oligonucleotide that is able to specifically hybridize to a target sequence (C) having a nucleotide sequence that comprises or consists essentially of SEQ ID NO:14; and
      wherein said mutant probe (C) oligonucleotide is preferably labeled with a fluorophore and a quencher of fluorescence of said fluorophore;
   2) performing a primer extension reaction; and
   3) determining whether the genetic variation A23403G is present in said sample, preferably by determining whether a fluorescent signal of said fluorophore has become detectable.

A further embodiment of the present invention provides for a method for detecting the presence of the genetic variation G22813T of the spike gene of SARS-CoV-2 wildtype in a sample, wherein said method comprises
   1) contacting a sample with
      a) Forward Primer (D) comprising or consisting of an oligonucleotide having SEQ ID NO: 21,
      b) Reverse Primer (D) comprising or consisting of an oligonucleotide having SEQ ID NO: 22; and
      c) a mutant probe (D) comprising or consisting of or a variant of an oligonucleotide of SEQ ID NO:24 said mutant probe (D) being a detectably labeled oligonucleotide that is able to specifically hybridize to a target sequence (D) having a nucleotide sequence that comprises or consists essentially of SEQ ID NO:20; and
      wherein said mutant probe (D) oligonucleotide is preferably labeled with a fluorophore and a quencher of fluorescence of said fluorophore;
   2) performing a primer extension reaction; and
   3) determining whether the genetic variation G22813T is present in said sample, preferably by determining whether a fluorescent signal of said fluorophore has become detectable.

A further embodiment of the present invention provides for a method for detecting the presence of the genetic variation C23604A of the spike gene of SARS-CoV-2 wildtype in a sample, wherein said method comprises
   1) contacting a sample with
      a) Forward Primer (E) comprising or consisting of an oligonucleotide having SEQ ID NO: 27, b) Reverse Primer (E) comprising or consisting of an oligonucleotide having SEQ ID NO: 28; and c) a mutant probe (E) comprising or consisting of or a variant of an oligonucleotide of SEQ ID NO:30 said mutant probe (E) being a detectably labeled oligonucleotide that is able to specifically hybridize to a target sequence (E) having a nucleotide sequence that comprises or consists essentially of SEQ ID NO:26; and wherein said mutant probe (E) oligonucleotide is preferably labeled with a fluorophore and a quencher of fluorescence of said fluorophore;

2) performing a primer extension reaction; and 3) determining whether the genetic variation C23604A is present in said sample, preferably by determining whether a fluorescent signal of said fluorophore has become detectable.

A further embodiment of the present invention provides for a method for detecting the presence of the genetic variation C22227T of the spike gene of SARS-CoV-2 wild-type in a sample, wherein said method comprises 1) contacting a sample with
a) Forward Primer (F) comprising or consisting of an oligonucleotide having SEQ ID NO: 33,
b) Reverse Primer (F) comprising or consisting of an oligonucleotide having SEQ ID NO: 34; and c) a mutant probe (F) comprising or consisting of or a variant of an oligonucleotide of SEQ ID NO:36 said mutant probe (F) being a detectably labeled oligonucleotide that is able to specifically hybridize to a target sequence (F) having a nucleotide sequence that comprises or consists essentially of SEQ ID NO:32; and wherein said mutant probe (F) oligonucleotide is preferably labeled with a fluorophore and a quencher of fluorescence of said fluorophore;

2) performing a primer extension reaction; and 3) determining whether the genetic variation C22227T is present in said sample, preferably by determining whether a fluorescent signal of said fluorophore has become detectable.

A further embodiment of the present invention provides for a method for detecting the presence of the genetic variation G22992A of the spike gene of SARS-CoV-2 wild-type in a sample, wherein said method comprises 1) contacting a sample with a) Forward Primer (G) comprising or consisting of an oligonucleotide having SEQ ID NO: 39, b) Reverse Primer (G) comprising or consisting of an oligonucleotide having SEQ ID NO: 40; and c) a mutant probe (G) comprising or consisting of or a variant of SEQ ID NO:42 said mutant probe (G) being a detectably labeled oligonucleotide that is able to specifically hybridize to a target sequence (G) having a nucleotide sequence that comprises or consists essentially of SEQ ID NO:38; and wherein said mutant probe (G) oligonucleotide is preferably labeled with a fluorophore and a quencher of fluorescence of said fluorophore;

2) performing a primer extension reaction; and 3) determining whether the genetic variation G22992A is present in said sample, preferably by determining whether a fluorescent signal of said fluorophore has become detectable.

A further embodiment of the present invention provides for a method for detecting the presence of the genetic variation G25088T of the spike gene of SARS-CoV-2 wild-type in a sample, wherein said method comprises 1) contacting a sample with a) Forward Primer (H) comprising or consisting of an oligonucleotide having SEQ ID NO: 45, b) Reverse Primer (H) comprising or consisting of an oligonucleotide having SEQ ID NO: 46; and c) a mutant probe (H) comprising or consisting of or a variant of an oligonucleotide of SEQ ID NO:48 said mutant probe (H) being a detectably labeled oligonucleotide that is able to specifically hybridize to a target sequence (H) having a nucleotide sequence that comprises or consists essentially of SEQ ID NO:44; and wherein said mutant probe (H) oligonucleotide is preferably labeled with a fluorophore and a quencher of fluorescence of said fluorophore;

2) performing a primer extension reaction; and 3) determining whether the genetic variation G25088T is present in said sample, preferably by determining whether a fluorescent signal of said fluorophore has become detectable.

A further embodiment of the present invention provides for a method for detecting the presence of the genetic variation C22879A of the spike gene of SARS-CoV-2 wild-type in a sample, wherein said method comprises 1) contacting a sample with a) Forward Primer (I) comprising or consisting of an oligonucleotide having SEQ ID NO: 51, b) Reverse Primer (I) comprising or consisting of an oligonucleotide having SEQ ID NO: 52; and c) a mutant probe (I) comprising or consisting of or a variant of an oligonucleotide of SEQ ID NO:54 said mutant probe (I) being a detectably labeled oligonucleotide that is able to specifically hybridize to a target sequence (I) having a nucleotide sequence that comprises or consists essentially of SEQ ID NO:50; and wherein said mutant probe (I) oligonucleotide is preferably labeled with a fluorophore and a quencher of fluorescence of said fluorophore;

2) performing a primer extension reaction; and 3) determining whether the genetic variation C22879A is present in said sample, preferably by determining whether a fluorescent signal of said fluorophore has become detectable.

A further embodiment of the present invention provides for a method for detecting the presence of the genetic variation G23012A of the spike gene of SARS-CoV-2 wild-type in a sample, wherein said method comprises 1) contacting a sample with a) Forward Primer (J) comprising or consisting of an oligonucleotide having SEQ ID NO: 57, b) Reverse Primer (J) comprising or consisting of an oligonucleotide having SEQ ID NO: 58; and c) a mutant probe (J) comprising or consisting of or a variant of an oligonucleotide of SEQ ID NO:60 said mutant probe (J) being a detectably labeled oligonucleotide that is able to specifically hybridize to a target sequence (J) having a nucleotide sequence that comprises or consists essentially of SEQ ID NO:56; and wherein said mutant probe (J) oligonucleotide is preferably labeled with a fluorophore and a quencher of fluorescence of said fluorophore;

2) performing a primer extension reaction; and
3) determining whether the genetic variation G23012A is present in said sample, preferably by determining whether a fluorescent signal of said fluorophore has become detectable.

A further embodiment of the invention is a method for detecting the presence of a genetic variation (mutant) of SARS-CoV-2 wildtype in a sample, wherein said method comprises:
(I) incubating said sample in vitro in the presence of:
(1) a reverse transcriptase and a DNA polymerase; and
(2) amplification primers comprising a Forward Primer and a Reverse Primer said amplification primers being suitable for specifically hybridizing to a target sequence selected from oligonucleotides comprising the genetic variation of the spike gene of SARS-CoV-2 or a fragment thereof comprising said genetic variation; and
(3) a mutant probe, said mutant probe being an oligonucleotide that is able to specifically hybridize to a target sequence selected from the nucleotides comprising the genetic variation of the spike gene of SARS-CoV-2 or a fragment thereof, wherein said mutant probe oligonucleotide is labeled with a fluorophore and a quencher of fluorescence of said fluorophore,
wherein said incubation is in a reaction under conditions sufficient to permit:
(a) said Forward and Reverse Primers to mediate a polymerase chain reaction amplification of a region of the genetic variation (mutant) of SARS-CoV-2 wildtype to thereby produce amplified target sequence molecules, if said mutant of SARS-CoV-2 is present in said sample;
(b) said mutant probe to hybridize to said amplified target sequence molecules; and
(c) (1) said DNA polymerase has a 5'→3' exonuclease activity that hydrolyzes said hybridized mutant probe, to thereby separate said fluorophore thereof from said quencher thereof and cause a fluorescent signal to become detectable; or
(2) said hybridization of said mutant probe to said amplified target sequence molecule separates said fluorophore thereof from said quencher thereof and causes a fluorescent signal to become detectable; and
(II) determining whether said mutant of SARS-CoV-2 is present in said sample by determining whether a fluorescent signal of said fluorophore has become detectable; wherein preferably the oligonucleotide of the mutant probe is one selected from the group consisting of SEQ ID NO:6, SEQ ID NO:12, SEQ ID NO:18, SEQ ID NO:24, SEQ ID NO:30, SEQ ID NO:36, SEQ ID NO:42, SEQ ID NO:48, SEQ ID NO:54 and SEQ ID NO:60, preferably the oligonucleotide of the mutant probe is selected from the group consisting of SEQ ID NO:6 and SEQ ID NO:60 and SEQ ID NO:24.

Preferably said fluorophore has an excitation wavelength within the range of about 352-690 nm and an emission wavelength within the range of about 447-705 nm. Especially preferred are mutant probes wherein said fluorophore is HEX.

In a preferred aspect the method of the invention comprises real-time PCR.

In an especially preferred embodiment of the method said sample is contacted in the additional presence of:
(5) an wildtype probe, said wildtype probe being an oligonucleotide that is able to specifically hybridize to an oligonucleotide having a nucleotide sequence that comprises or consists essentially of the nucleotide sequence selected from the group consisting of SEQ ID NO:1, SEQ ID NO:7, SEQ ID NO:13, SEQ ID NO:19, SEQ ID NO:25, SEQ ID NO:31, SEQ ID NO:37, SEQ ID NO:43, SEQ ID NO:49 and SEQ ID NO:55; and wherein said wildtype probe oligonucleotide is labeled with a fluorophore and to a quencher of fluorescence of said fluorophore; wherein the fluorescence of said fluorophore of said wildtype probe is distinguishable from the fluorescence of said fluorophore of said mutant probe;
wherein said reaction is additionally incubated under conditions sufficient to permit:
(a) said amplification primers comprising Forward and Reverse Primers to mediate a polymerase chain reaction amplification of a region of the spike gene of SARS-CoV-2 wildtype as defined in one selected from the group consisting of SEQ ID NO:1, SEQ ID NO:7, SEQ ID NO:13, SEQ ID NO:19, SEQ ID NO:25, SEQ ID NO:31, SEQ ID NO:37, SEQ ID NO:43, SEQ ID NO:49 and SEQ ID NO:55 to thereby produce amplified spike gene oligonucleotide molecules, if said SARS-CoV-2 wildtype is present in said sample;
(b) said wildtype probe to hybridize to said amplified spike gene oligonucleotide molecules; and
(c) (1) said DNA polymerase has a 5'→3' exonuclease activity that hydrolyzes said hybridized wildtype probe, to thereby separate said fluorophore thereof from said quencher thereof and cause a fluorescent signal to become detectable; or
(2) said hybridization of said wildtype probe to said amplified spike gene oligonucleotide molecules separates said fluorophore thereof from said quencher thereof and causes a fluorescent signal to become detectable; and
wherein said SARS-CoV-2 wildtype or said mutant of SARS-CoV-2 respectively is determined to be present in said sample by determining whether a fluorescent signal of one of said wildtype probe or said mutant probe fluorophores has become detectable.

In a further preferred aspect of the method of the invention said sample is contacted in the additional presence of:
(5) an wildtype probe, said wildtype probe being an oligonucleotide that is able to specifically hybridize to an oligonucleotide having a nucleotide sequence that comprises or consists essentially of the nucleotide sequence selected from the group consisting of SEQ ID NO:1 and SEQ ID NO:55 and optionally SEQ ID NO:19; preferably SEQ ID NO:1 and SEQ ID NO:55 and SEQ ID NO:19; and wherein said wildtype probe oligonucleotide is labeled with a fluorophore and to a quencher of fluorescence of said fluorophore; wherein the fluorescence of said fluorophore of said wildtype probe is distinguishable from the fluorescence of said fluorophore of said mutant probe;
wherein said reaction is additionally incubated under conditions sufficient to permit:
(a) said amplification primers comprising Forward and Reverse Primers to mediate a polymerase chain reaction amplification of a region of the spike gene of SARS-CoV-2 wildtype as defined in one selected from the group consisting of SEQ ID NO:1 and SEQ ID NO:55 and optionally SEQ ID NO:19, preferably SEQ ID NO:1 and SEQ ID NO:55 and SEQ ID NO:19, to thereby produce amplified spike gene oligonucleotide molecules, if said SARS-CoV-2 wildtype is present in said sample;

(b) said wildtype probe to hybridize to said amplified spike gene oligonucleotide molecules; and (c) (1) said DNA polymerase has a 5'→3' exonuclease activity that hydrolyzes said hybridized wildtype probe, to thereby separate said fluorophore thereof from said quencher thereof and cause a fluorescent signal to become detectable; or (2) said hybridization of said wildtype probe to said amplified spike gene oligonucleotide molecules separates said fluorophore thereof from said quencher thereof and causes a fluorescent signal to become detectable; and wherein said SARS-CoV-2 wildtype or said mutant of SARS-CoV-2 respectively is determined to be present in said sample by determining whether a fluorescent signal of one of said wildtype probe or said mutant probe fluorophores has become detectable.

In a preferred embodiment of the method said fluorophore of said wildtype probe and said fluorophore of said mutant probe have an excitation wavelength within the range of about 352-690 nm and an emission wavelength within the range of about 447-705 nm.

In an especially preferred aspect of the method of the invention said wildtype probe is a fragment of an oligonucleotide of SARS-CoV-2 wild type said probe having a nucleotide sequence that comprises or consists essentially of one of the nucleotide sequences selected from SEQ ID NO:5, SEQ ID NO:11, SEQ ID NO:17, SEQ ID NO:23, SEQ ID NO:29, SEQ ID NO:35, SEQ ID NO:41, SEQ ID NO:47, SEQ ID NO:53 and SEQ ID NO:59.

In a further preferred aspect said wildtype probe is a fragment of an oligonucleotide of SARS-CoV-2 wild type said probe having a nucleotide sequence that consists essentially of one of the nucleotide sequences selected from SEQ ID NO:5 and SEQ ID NO:59 and optionally SEQ ID NO:23, especially the nucleotide sequences are selected from SEQ ID NO:5 and SEQ ID NO:59 and SEQ ID NO:23.

For the convenient handling of the users kits for PCR cycler are provided.

Therefore, in a further aspect of the invention a kit is provided said kit being for detecting the presence of SARS-CoV-2 and/or a mutant of SARS-CoV-2 in a sample, wherein said kit comprises one or more of the following systems A to J:

System A for the detection of genetic variation A23063T of the spike gene of SARS-CoV-2 comprising:
(1) a Forward Primer (A) having a nucleotide sequence that consists essentially of the nucleotide sequence of SEQ ID NO:3;
(2) a Reverse Primer (A) having a nucleotide sequence that consists essentially of the nucleotide sequence of SEQ ID NO:4; and
(3) probe(s) comprising
i) a wildtype probe (A) oligonucleotide which has a nucleotide sequence that comprises or is consisting essentially of the nucleotide sequence of SEQ ID NO:5 and which is preferably labeled with a fluorophore and a quencher of fluorescence of said fluorophore;
and/or
ii) a mutant probe (A) oligonucleotide which has a nucleotide sequence that comprises or is consisting essentially of the nucleotide sequence of SEQ ID NO:6 and which is preferably labeled with a fluorophore and a quencher of fluorescence of said fluorophore;
(4) optionally at least one target positive control oligonucleotide comprising SEQ ID NO:1 and/or SEQ ID NO:2;

System B for the detection of genetic variation del21765-770 of the spike gene of SARS-CoV-2 comprising:
(1) a Forward Primer (B) having a nucleotide sequence that consists essentially of the nucleotide sequence of SEQ ID NO:9;
(2) a Reverse Primer (B) having a nucleotide sequence that consists essentially of the nucleotide sequence of SEQ ID NO:10; and
(3) probe(s) comprising
i) a wildtype probe (B) oligonucleotide which has a nucleotide sequence that comprises or is consisting essentially of the nucleotide sequence of SEQ ID NO:11 and which is preferably labeled with a fluorophore and a quencher of fluorescence of said fluorophore;
and/or
ii) a mutant probe (B) oligonucleotide which has a nucleotide sequence that comprises or is consisting essentially of the nucleotide sequence of SEQ ID NO:12 and which is preferably labeled with a fluorophore and a quencher of fluorescence of said fluorophore;
(4) optionally at least one target positive control oligonucleotide comprising SEQ ID NO:7 and/or SEQ ID NO:8;

System C for the detection of genetic variation A23403G of the spike gene of SARS-CoV-2 comprising:
(1) a Forward Primer (C) having a nucleotide sequence that consists essentially of the nucleotide sequence of SEQ ID NO:15;
(2) a Reverse Primer (C) having a nucleotide sequence that consists essentially of the nucleotide sequence of SEQ ID NO:16; and
(3) probe(s) comprising
i) a wildtype probe (C) oligonucleotide which has a nucleotide sequence that comprises or is consisting essentially of the nucleotide sequence of SEQ ID NO:17 and which is preferably labeled with a fluorophore and a quencher of fluorescence of said fluorophore;
and/or
ii) a mutant probe (C) oligonucleotide which has a nucleotide sequence that comprises or is consisting essentially of the nucleotide sequence of SEQ ID NO:18 and which is preferably labeled with a fluorophore and a quencher of fluorescence of said fluorophore;
(4) optionally at least one target positive control oligonucleotide comprising SEQ ID NO:13 and/or SEQ ID NO:14;

System D for the detection of genetic variation G22813T of the spike gene of SARS-CoV-2 comprising:
(1) a Forward Primer (D) having a nucleotide sequence that consists essentially of the nucleotide sequence of SEQ ID NO:21;
(2) a Reverse Primer (D) having a nucleotide sequence that consists essentially of the nucleotide sequence of SEQ ID NO:22; and
(3) probe(s) comprising
i) a wildtype probe (D) oligonucleotide which has a nucleotide sequence that comprises or is consisting essentially of the nucleotide sequence of SEQ ID NO:23 and which is preferably labeled with a fluorophore and a quencher of fluorescence of said fluorophore;

and/or ii) a mutant probe (D) oligonucleotide which has a nucleotide sequence that comprises or is consisting essentially of the nucleotide sequence of SEQ ID NO:24 and which is preferably labeled with a fluorophore and a quencher of fluorescence of said fluorophore;

(4) optionally at least one target positive control oligonucleotide comprising SEQ ID NO:19 and/or SEQ ID NO:20;

System E for the detection of genetic variation C23604A of the spike gene of SARS-CoV-2 comprising:

(1) a Forward Primer (E) having a nucleotide sequence that consists essentially of the nucleotide sequence of SEQ ID NO:27;

(2) a Reverse Primer (E) having a nucleotide sequence that consists essentially of the nucleotide sequence of SEQ ID NO:28; and (3) probe(s) comprising i) a wildtype probe (E) oligonucleotide which has a nucleotide sequence that comprises or is consisting essentially of the nucleotide sequence of SEQ ID NO:29 and which is preferably labeled with a fluorophore and a quencher of fluorescence of said fluorophore;

and/or ii) a mutant probe (E) oligonucleotide which has a nucleotide sequence that comprises or is consisting essentially of the nucleotide sequence of SEQ ID NO:30 and which is preferably labeled with a fluorophore and a quencher of fluorescence of said fluorophore;

(4) optionally at least one target positive control oligonucleotide comprising SEQ ID NO:25 and/or SEQ ID NO:26;

System F for the detection of genetic variation C22227T of the spike gene of SARS-CoV-2 comprising:

(1) a Forward Primer (F) having a nucleotide sequence that consists essentially of the nucleotide sequence of SEQ ID NO:33;

(2) a Reverse Primer (F) having a nucleotide sequence that consists essentially of the nucleotide sequence of SEQ ID NO:34; and (3) probe(s) comprising i) a wildtype probe (F) oligonucleotide which has a nucleotide sequence that comprises or is consisting essentially of the nucleotide sequence of SEQ ID NO:35 and which is preferably labeled with a fluorophore and a quencher of fluorescence of said fluorophore;

and/or ii) a mutant probe (F) oligonucleotide which has a nucleotide sequence that comprises or is consisting essentially of the nucleotide sequence of SEQ ID NO:36 and which is preferably labeled with a fluorophore and a quencher of fluorescence of said fluorophore;

(4) optionally at least one target positive control oligonucleotide comprising SEQ ID NO:31 and/or SEQ ID NO:32;

System G for the detection of genetic variation G22992A of the spike gene of SARS-CoV-2 comprising:

(1) a Forward Primer (G) having a nucleotide sequence that consists essentially of the nucleotide sequence of SEQ ID NO:39;

(2) a Reverse Primer (G) having a nucleotide sequence that consists essentially of the nucleotide sequence of SEQ ID NO:40; and (3) probe(s) comprising i) a wildtype probe (G) oligonucleotide which has a nucleotide sequence that comprises or is consisting essentially of the nucleotide sequence of SEQ ID NO:41 and which is preferably labeled with a fluorophore and a quencher of fluorescence of said fluorophore;

and/or ii) a mutant probe (G) oligonucleotide which has a nucleotide sequence that comprises or is consisting essentially of the nucleotide sequence of SEQ ID NO:42 and which is preferably labeled with a fluorophore and a quencher of fluorescence of said fluorophore;

(4) optionally at least one target positive control oligonucleotide comprising SEQ ID NO:37 and/or SEQ ID NO:38;

System H for the detection of genetic variation G25088T of the spike gene of SARS-CoV-2 comprising:

(1) a Forward Primer (H) having a nucleotide sequence that consists essentially of the nucleotide sequence of SEQ ID NO:45;

(2) a Reverse Primer (H) having a nucleotide sequence that consists essentially of the nucleotide sequence of SEQ ID NO:46; and (3) probe(s) comprising i) a wildtype probe (H) oligonucleotide which has a nucleotide sequence that comprises or is consisting essentially of the nucleotide sequence of SEQ ID NO:47 and which is preferably labeled with a fluorophore and a quencher of fluorescence of said fluorophore;

and/or ii) a mutant probe (H) oligonucleotide which has a nucleotide sequence that comprises or is consisting essentially of the nucleotide sequence of SEQ ID NO:48 and which is preferably labeled with a fluorophore and a quencher of fluorescence of said fluorophore;

(4) optionally at least one target positive control oligonucleotide comprising SEQ ID NO:43 and/or SEQ ID NO:44;

System I for the detection of genetic variation C22879A of the spike gene of SARS-CoV-2 comprising:

(1) a Forward Primer (I) having a nucleotide sequence that consists essentially of the nucleotide sequence of SEQ ID NO:51;

(2) a Reverse Primer (I) having a nucleotide sequence that consists essentially of the nucleotide sequence of SEQ ID NO:52; and (3) probe(s) comprising i) a wildtype probe (I) oligonucleotide which has a nucleotide sequence that comprises or is consisting essentially of the nucleotide sequence of SEQ ID NO:53 and which is preferably labeled with a fluorophore and a quencher of fluorescence of said fluorophore;

and/or ii) a mutant probe (I) oligonucleotide which has a nucleotide sequence that comprises or is consisting essentially of the nucleotide sequence of SEQ ID NO:54 and which is preferably labeled with a fluorophore and a quencher of fluorescence of said fluorophore;
(4) optionally at least one target positive control oligonucleotide comprising SEQ ID NO:49 and/or SEQ ID NO:50; and System J for the detection of genetic variation G23012A of the spike gene of SARS-CoV-2 comprising:
(1) a Forward Primer (J) having a nucleotide sequence that consists essentially of the nucleotide sequence of SEQ ID NO:57;
(2) a Reverse Primer (J) having a nucleotide sequence that consists essentially of the nucleotide sequence of SEQ ID NO:58; and
(3) probe(s) comprising
i) a wildtype probe (J) oligonucleotide which has a nucleotide sequence that comprises or is consisting essentially of the nucleotide sequence of SEQ ID NO:59 and which is preferably labeled with a fluorophore and a quencher of fluorescence of said fluorophore;
and/or
ii) a mutant probe (J) oligonucleotide which has a nucleotide sequence that comprises or is consisting essentially of the nucleotide sequence of SEQ ID NO:60 and which is preferably labeled with a fluorophore and a quencher of fluorescence of said fluorophore;
(4) optionally at least one target positive control oligonucleotide comprising or consisting of SEQ ID NO:55 and/or SEQ ID NO:56.

A kit for detecting the presence of SARS-CoV-2 and/or a mutant of SARS-CoV-2 in a sample, wherein said kit comprises one or more of the following systems A and J and optionally D, preferably systems A, J and D:

System A for the detection of genetic variation A23063T of the spike gene of SARS-CoV-2 comprising:
(1) a Forward Primer (A) having a nucleotide sequence that consists essentially of the nucleotide sequence of SEQ ID NO:3;
(2) a Reverse Primer (A) having a nucleotide sequence that consists essentially of the nucleotide sequence of SEQ ID NO:4; and
(3) probe(s) comprising
i) a wildtype probe (A) oligonucleotide which has a nucleotide sequence that comprises or is consisting essentially of the nucleotide sequence of SEQ ID NO:5 and which is preferably labeled with a fluorophore and a quencher of fluorescence of said fluorophore;
and/or
ii) a mutant probe (A) oligonucleotide which has a nucleotide sequence that comprises or is consisting essentially of the nucleotide sequence of SEQ ID NO:6 and which is preferably labeled with a fluorophore and a quencher of fluorescence of said fluorophore;
(4) optionally at least one target positive control oligonucleotide comprising SEQ ID NO:1 and/or SEQ ID NO:2;

System J for the detection of genetic variation G23012A of the spike gene of SARS-CoV-2 comprising:
(1) a Forward Primer (J) having a nucleotide sequence that consists essentially of the nucleotide sequence of SEQ ID NO:57;
(2) a Reverse Primer (J) having a nucleotide sequence that consists essentially of the nucleotide sequence of SEQ ID NO:58; and
(3) probe(s) comprising
i) a wildtype probe (J) oligonucleotide which has a nucleotide sequence that comprises or is consisting essentially of the nucleotide sequence of SEQ ID NO:59 and which is preferably labeled with a fluorophore and a quencher of fluorescence of said fluorophore;
and/or
ii) a mutant probe (J) oligonucleotide which has a nucleotide sequence that comprises or is consisting essentially of the nucleotide sequence of SEQ ID NO:60 and which is preferably labeled with a fluorophore and a quencher of fluorescence of said fluorophore;
(4) optionally at least one target positive control oligonucleotide comprising SEQ ID NO:55 and/or SEQ ID NO:56.

System D for the detection of genetic variation G22813T of the spike gene of SARS-CoV-2 comprising:
(1) a Forward Primer (D) having a nucleotide sequence that consists essentially of the nucleotide sequence of SEQ ID NO:21;
(2) a Reverse Primer (D) having a nucleotide sequence that consists essentially of the nucleotide sequence of SEQ ID NO:22; and
(3) probe(s) comprising
i) a wildtype probe (D) oligonucleotide which has a nucleotide sequence that comprises or is consisting essentially of the nucleotide sequence of SEQ ID NO:23 and which is preferably labeled with a fluorophore and a quencher of fluorescence of said fluorophore;
and/or
ii) a mutant probe (D) oligonucleotide which has a nucleotide sequence that comprises or is consisting essentially of the nucleotide sequence of SEQ ID NO:24 and which is preferably labeled with a fluorophore and a quencher of fluorescence of said fluorophore;
(4) optionally at least one target positive control oligonucleotide comprising SEQ ID NO:19 and/or SEQ ID NO:20.

In a preferred embodiment the kit comprises two or more, three or more, four or more, five or more, especially 6, 7, 8, 9 or more of one of the systems A to J.

According to a further preferred aspect the kit comprises systems A to J.

Especially preferred is a kit which comprises system A and J and optionally one or more of systems B to I, especially A, J and D.

Preferably, each system is provided in a separate container.

A further aspect of the invention is the kit of the invention for use in the detection and determination SARS-CoV-2 and/or a mutant of SARS-CoV-2 in a sample.

A further embodiment is a method for the detection and determination of SARS-CoV-2 and/or a mutant of SARS-CoV-2 in a sample using the kit of the invention, the method comprising the step of
a) separately contacting the sample with one or more of systems A to J of a kit according to the invention;

b) performing a PCR with each of the contacted samples:
c) determining the presence of SARS-CoV-2 and/or a mutant of SARS-CoV-2 in the sample, preferably by fluorescence analysis.

Preferred is a method for the detection and determination of SARS-CoV-2 and/or a mutant of SARS-CoV-2 in a sample using the kit according to the invention the method comprising the step of
   a) separately contacting the sample with one or more of systems A and J and D of a kit of the invention;
   b) performing a PCR with each of the contacted samples:
   c) determining the presence of SARS-CoV-2 and/or a mutant of SARS-CoV-2 in the sample, preferably by fluorescence analysis.

Preferred is a method wherein the fluorescence signal for of the mutant probe is different from the fluorescence signal of the wildtype probe.

It has further been surprisingly found that two or more genetic variations of the SARS-CoV-2 wildtype can be detected simultaneously with the method of the present invention.

Thus, another embodiment of the present invention is a method for detecting the presence of two or more genetic variation (mutant) of SARS-CoV-2 wildtype in a sample, wherein said method comprises
   1) contacting a sample with two or more, preferably three or four or five or more of the following A to J:
   wherein A comprises
      (1) a Forward Primer (A) having a nucleotide sequence that consists essentially of the nucleotide sequence of SEQ ID NO:3;
      (2) a Reverse Primer (A) having a nucleotide sequence that consists essentially of the nucleotide sequence of SEQ ID NO:4; and
      (3) a mutant probe (A) oligonucleotide which has a nucleotide sequence that comprises or is consisting essentially of the nucleotide sequence of SEQ ID NO:6 and which is preferably labeled with a fluorophore and a quencher of fluorescence of said fluorophore;
   wherein B comprises
      (1) a Forward Primer (B) having a nucleotide sequence that consists essentially of the nucleotide sequence of SEQ ID NO:9;
      (2) a Reverse Primer (B) having a nucleotide sequence that consists essentially of the nucleotide sequence of SEQ ID NO:10; and
      (3) a mutant probe (B) oligonucleotide which has a nucleotide sequence that comprises or is consisting essentially of the nucleotide sequence of SEQ ID NO:12 and which is preferably labeled with a fluorophore and a quencher of fluorescence of said fluorophore;
   wherein C comprises
      (1) a Forward Primer (C) having a nucleotide sequence that consists essentially of the nucleotide sequence of SEQ ID NO:15;
      (2) a Reverse Primer (C) having a nucleotide sequence that consists essentially of the nucleotide sequence of SEQ ID NO:16; and
      (3) a mutant probe (C) oligonucleotide which has a nucleotide sequence that comprises or is consisting essentially of the nucleotide sequence of SEQ ID NO:18 and which is preferably labeled with a fluorophore and a quencher of fluorescence of said fluorophore;
   wherein D comprises
      (1) a Forward Primer (D) having a nucleotide sequence that consists essentially of the nucleotide sequence of SEQ ID NO:21;
      (2) a Reverse Primer (D) having a nucleotide sequence that consists essentially of the nucleotide sequence of SEQ ID NO:22; and
      (3) a mutant probe (D) oligonucleotide which has a nucleotide sequence that comprises or is consisting essentially of the nucleotide sequence of SEQ ID NO:24 and which is preferably labeled with a fluorophore and a quencher of fluorescence of said fluorophore;
   wherein E comprises
      (1) a Forward Primer (E) having a nucleotide sequence that consists essentially of the nucleotide sequence of SEQ ID NO:27;
      (2) a Reverse Primer (E) having a nucleotide sequence that consists essentially of the nucleotide sequence of SEQ ID NO:28; and
      (3) a mutant probe (E) oligonucleotide which has a nucleotide sequence that comprises or is consisting essentially of the nucleotide sequence of SEQ ID NO:30 and which is preferably labeled with a fluorophore and a quencher of fluorescence of said fluorophore;
   wherein F comprises
      (1) a Forward Primer (F) having a nucleotide sequence that consists essentially of the nucleotide sequence of SEQ ID NO:33;
      (2) a Reverse Primer (F) having a nucleotide sequence that consists essentially of the nucleotide sequence of SEQ ID NO:34; and
      (3) a mutant probe (F) oligonucleotide which has a nucleotide sequence that comprises or is consisting essentially of the nucleotide sequence of SEQ ID NO:36 and which is preferably labeled with a fluorophore and a quencher of fluorescence of said fluorophore;
   wherein G comprises
      (1) a Forward Primer (G) having a nucleotide sequence that consists essentially of the nucleotide sequence of SEQ ID NO:39;
      (2) a Reverse Primer (G) having a nucleotide sequence that consists essentially of the nucleotide sequence of SEQ ID NO:40; and
      (3) a mutant probe (G) oligonucleotide which has a nucleotide sequence that comprises or is consisting essentially of the nucleotide sequence of SEQ ID NO:42 and which is preferably labeled with a fluorophore and a quencher of fluorescence of said fluorophore;
   wherein H comprises
      (1) a Forward Primer (H) having a nucleotide sequence that consists essentially of the nucleotide sequence of SEQ ID NO:45;
      (2) a Reverse Primer (H) having a nucleotide sequence that consists essentially of the nucleotide sequence of SEQ ID NO:46; and
      (3) a mutant probe (H) oligonucleotide which has a nucleotide sequence that comprises or is consisting essentially of the nucleotide sequence of SEQ ID NO:48 and which is preferably labeled with a fluorophore and a quencher of fluorescence of said fluorophore;

wherein I comprises
- (1) a Forward Primer (I) having a nucleotide sequence that consists essentially of the nucleotide sequence of SEQ ID NO:51;
- (2) a Reverse Primer (I) having a nucleotide sequence that consists essentially of the nucleotide sequence of SEQ ID NO:52; and
- (3) a mutant probe (I) oligonucleotide which has a nucleotide sequence that comprises or is consisting essentially of the nucleotide sequence of SEQ ID NO:54 and which is preferably labeled with a fluorophore and a quencher of fluorescence of said fluorophore; and wherein J comprises
- (1) a Forward Primer (J) having a nucleotide sequence that consists essentially of the nucleotide sequence of SEQ ID NO:57;
- (2) a Reverse Primer (J) having a nucleotide sequence that consists essentially of the nucleotide sequence of SEQ ID NO:58; and
- (3) a mutant probe (J) oligonucleotide which has a nucleotide sequence that comprises or is consisting essentially of the nucleotide sequence of SEQ ID NO:60 and which is preferably labeled with a fluorophore and a quencher of fluorescence of said fluorophore;

2) performing a multiplex primer extension reaction; and
3) determining whether the genetic variation of the spike gene of SARS-CoV-2 or a fragment thereof is present in said sample, preferably by determining whether a fluorescent signal of said fluorophore has become detectable.

In particular the above-mentioned method is suitable for the detection of the genetic variation of the spike gene of SARS-CoV-2 selected from the group consisting of A23063T, del21765-770, A23403G, G22813T, C23604A, C22227T, G22992A, G25088T, C22879A and G23012A.

One aspect of the invention is a method for detecting the presence of genetic variation(s) (mutant) of SARS-CoV-2 wildtype in a sample, wherein said method comprises
1) contacting a sample with the following A and J and optionally D:

wherein A comprises
- (1) a Forward Primer (A) having a nucleotide sequence that consists essentially of the nucleotide sequence of SEQ ID NO:3;
- (2) a Reverse Primer (A) having a nucleotide sequence that consists essentially of the nucleotide sequence of SEQ ID NO:4; and
- (3) a mutant probe (A) oligonucleotide which has a nucleotide sequence that comprises or is consisting essentially of the nucleotide sequence of SEQ ID NO:6 and which is preferably labeled with a fluorophore and a quencher of fluorescence of said fluorophore;

and
wherein J comprises
- (1) a Forward Primer (J) having a nucleotide sequence that consists essentially of the nucleotide sequence of SEQ ID NO:57;
- (2) a Reverse Primer (J) having a nucleotide sequence that consists essentially of the nucleotide sequence of SEQ ID NO:58; and
- (3) a mutant probe (J) oligonucleotide which has a nucleotide sequence that comprises or is consisting essentially of the nucleotide sequence of SEQ ID NO:60 and which is preferably labeled with a fluorophore and a quencher of fluorescence of said fluorophore;

wherein D comprises
- (1) a Forward Primer (D) having a nucleotide sequence that consists essentially of the nucleotide sequence of SEQ ID NO:21;
- (2) a Reverse Primer (D) having a nucleotide sequence that consists essentially of the nucleotide sequence of SEQ ID NO:22; and
- (3) a mutant probe (D) oligonucleotide which has a nucleotide sequence that comprises or is consisting essentially of the nucleotide sequence of SEQ ID NO:24 and which is preferably labeled with a fluorophore and a quencher of fluorescence of said fluorophore;

2) performing a multiplex primer extension reaction; and
3) determining whether the genetic variation of the spike gene of SARS-CoV-2 or a fragment thereof is present in said sample, preferably by determining whether a fluorescent signal of said fluorophore has become detectable.

Preferably, the fluorophores of the mutant probes used in the multiplex primer extension reaction are distinguishable from each other.

In a preferred embodiment of the present invention said method being for detecting the presence of the genetic variation A23063T and one or more of the genetic variations selected from the group consisting of del21765-770, A23403G, G22813T, C23604A, C22227T, G22992A, G25088T, C22879A and G23012A of SARS-CoV-2 wildtype in a sample, wherein said method comprises
1) contacting a sample with A and one or more of B to J, preferably contacting a sample with A and J and optionally D.

Especially, the multiplex primer extension is a doublex or triplex or quadrouplex extension.

A specifically preferred embodiment of the present invention is a method for detecting the presence of the genetic variation A23063T and G23012A and optionally one or two or three or more of the genetic variations selected from the group consisting of del21765-770, A23403G, G22813T, C23604A, C22227T, G22992A, G25088T and C22879A comprising contacting a sample with A and J and optionally one or two or three or more of B to I.

Especially the present invention is a method for detecting the presence of the genetic variation A23063T and G23012A and G22813T comprising contacting a sample with A and J and D.

Preferably, the method is a method for detecting the presence of two or three or four or more of the genetic variations selected from the group consisting of A23063T, del21765-770, A23403G, G22813T, C23604A, C22227T, G22992A, G25088T, C22879A and G23012A of SARS-CoV-2 wildtype in a sample, wherein said method comprises
contacting a sample with A and B and optionally one or two or three or more of B to J; or
contacting a sample with A and C and optionally one or two or three or more of B and D to J; or
contacting a sample with A and D and one or two or three or more of B and C and E to J; or
contacting a sample with A and E and optionally one or two or three or more of B to D and F to J; or
contacting a sample with A and F and optionally one or two or three or more of B to E and G to J; or
contacting a sample with A and G and optionally one or two or three or more of B to F and H to J; or contacting a sample with A and H and optionally one or two or three or more of B to G and I and J; or contacting a sample with A and I and optionally one or two or three or more of B to H and J; or contacting a sample with A and J and one or two or three or more of B to I.

Advantageously the method can be conducted by simultaneously detecting the genetic variants which is efficient and convenient for the user and delivers clinical information within a short period of time for clinical people in the process of the treatment of a patient suffering from the a SARS-CoV-2 infection or infections of the respective mutants thereof.

Preferably, the genes and/or fragments are detected simultaneously, and more preferably, in a multiplex real-time PCR assay. Most preferably, amplification and detection are performed in a single reaction.

In a specifically preferred embodiment the variants A23063T and G23012A and G22813T and optionally N-gene of SARS-CoV-2 and/or RNAseP are detected. The simultaneous detection of the N-gene of SARS-CoV-2 supports the reliability and accuracy. Further the detection of human RNA can be used as a control for the reliability and correct operation of the method.

Typical and known primer and probes of the N-gene of SARS-CoV-2 as well as RNAseP are reflected in the following Table A. Preferably, the 2019 n-CoV_2 Primer and Probe can be used.

TABLE Aa

| Sequence ID No of the sequences of Table A | |
|---|---|
| Name | Seq ID NO |
| 2019-nCoV_N1-F | SEQ ID NO: 61 |
| 2019-nCoV_N1-R | SEQ ID NO: 62 |
| 2019-nCoV_N1-P | SEQ ID NO: 63 |
| 2019-nCoV_N2-F | SEQ ID NO: 64 |
| 2019-nCoV_N2-R | SEQ ID NO: 65 |
| 2019-nCoV_N2-P | SEQ ID NO: 66 |
| 2019-nCoV_N3-F | SEQ ID NO: 67 |
| 2019-nCoV_N3-R | SEQ ID NO: 68 |
| 2019-nCoV_N3-P | SEQ ID NO: 69 |
| RP-F | SEQ ID NO: 70 |
| RP-R | SEQ ID NO: 71 |
| RP-P | SEQ ID NO: 72 |

The method of the invention comprises preferably real-time PCR.

A further embodiment of the present invention is a kit for performing the above-mentioned method comprising at two or three or four or five or more of A to J, preferably A and J and optionally one or more of B to I.

A preferred embodiment of the present invention is a method for detecting the presence of variants A23063T and G23012A and optionally G22813T of SARS-CoV-2 wild-type in a sample, wherein said method comprises

| 2019 Novel Coronavirus (2019-nCoV) Real-Time rRT-PCR Panel Primers and Probes | | | | |
|---|---|---|---|---|
| Name | Description | Oligonucleotide Sequence (5'>3') | Label[1] | Working Conc. |
| 2019-nCoV_N1-F | 2019-nCoV_N1 Forward Primer | 5'-GAC CCC AAA ATC AGC GAA AT-3' | None | 20 μm |
| 2019-nCoV_N1-R | 2019-nCoV_N1 Reverse Primer | 5'-TCT GGT TAC TGC CAG TTG AAT CTG-3' | None | 20 μm |
| 2019-nCoV_N1-P | 2019-nCoV_N1 Probe | 5'-FAM-ACC CCG CAT TAC GTT TGG TGG ACC-BHQ1-3' | FAM, BHQ-1 | 5 μm |
| 2019-nCoV_N2-F | 2019-nCoV_N2 Forward Primer | 5'-TTA CAA ACA TTG GCC GCA AA-3' | None | 20 μm |
| 2019-nCoV_N2-R | 2019-nCoV_N2 Reverse Primer | 5'-GCG CGA CAT TCC GAA GAA-3' | None | 20 μm |
| 2019-nCoV_N2-P | 2019-nCoV_N2 Probe | 5'-FAM-ACA ATT TGC CCC CAG CGC TTC AG-BHQ1-3' | FAM, BHQ-1 | 5 μm |
| 2019-nCoV_N3-F | 2019-nCoV_N3 Forward Primer | 5'-GGG AGC CTT GAA TAC ACC AAA A-3' | None | 20 μm |
| 2019-nCoV_N3-R | 2019-nCoV_N3 Reverse Primer | 5'-TGT AGC ACG ATT GCA GCA TTG-3' | None | 20 μm |
| 2019-nCoV_N3-P | 2019-nCoV_N3 Probe | 5'-FAM-AYC ACA TTG GCA CCC GCA ATC CTG-BHQ1-3' | FAM-BHQ-1 | 5 μm |
| RP-F | RNAse P Forward Primer | 5'-AGA TTT GGA CCT GCG AGC G-3' | None | 20 μm |
| RP-R | RNAse P Reverse Primer | 5'-GAG CGG CTG TCT CCA CAA GT-3' | None | 20 μm |
| RP-P | RNAse P Probe | 5'-FAM - TTC TGA CCT GAA GGC TCT GCG CG-BHQ-1-3' | FAM, BHQ-1 | 5 μm |

[1]TaqMan® probes are labeled at the 5'-end with the reporter molecule 6-carboxyfluorescein (FAM) and with the quencher, Black Hole Quencher 1 (BHQ-1)(Biosearch Technologies, Inc., Novato, CA) at the 3'-end.

1) contacting a sample with:
   (1) a Forward Primer (A) having a nucleotide sequence that comprises or consists essentially of the nucleotide sequence of SEQ ID NO:3;
   (2) a Reverse Primer (A) having a nucleotide sequence that comprises or consists essentially of the nucleotide sequence of SEQ ID NO:4; and
   (3) a mutant probe (A) oligonucleotide which has a nucleotide sequence that comprises or is consisting essentially of the nucleotide sequence of SEQ ID NO:6 and which is preferably labeled with a fluorophore and a quencher of fluorescence of said fluorophore;
   (4) optionally a wildtype probe (A) oligonucleotide which has a nucleotide sequence that comprises or is consisting essentially of the nucleotide sequence of SEQ ID NO:5 and which is preferably labeled with a fluorophore and a quencher of fluorescence of said fluorophore; and further contacting the sample with
   (1) a Forward Primer (J) having a nucleotide sequence that comprises or consists essentially of the nucleotide sequence of SEQ ID NO:57;
   (2) a Reverse Primer (J) having a nucleotide sequence that comprises or consists essentially of the nucleotide sequence of SEQ ID NO:58;
   (3) a mutant probe (J) oligonucleotide which has a nucleotide sequence that comprises or is consisting essentially of the nucleotide sequence of SEQ ID NO:60 and which is preferably labeled with a fluorophore and a quencher of fluorescence of said fluorophore;
   (4) optionally a wildtype probe (J) oligonucleotide which has a nucleotide sequence that comprises or is consisting essentially of the nucleotide sequence of SEQ ID NO:59 and which is preferably labeled with a fluorophore and a quencher of fluorescence of said fluorophore; and further optionally contacting the sample with
   (1) a Forward Primer (D) having a nucleotide sequence that comprises or consists essentially of the nucleotide sequence of SEQ ID NO:21;
   (2) a Reverse Primer (D) having a nucleotide sequence that comprises or consists essentially of the nucleotide sequence of SEQ ID NO:22; and
   (3) a mutant probe (D) oligonucleotide which has a nucleotide sequence that comprises or is consisting essentially of the nucleotide sequence of SEQ ID NO:24 and which is preferably labeled with a fluorophore and a quencher of fluorescence of said fluorophore;
   (4) optionally a wildtype probe (D) oligonucleotide which has a nucleotide sequence that comprises or is consisting essentially of the nucleotide sequence of SEQ ID NO:23 and which is preferably labeled with a fluorophore and a quencher of fluorescence of said fluorophore;
2) performing a multiplex primer extension reaction; and
3) determining whether the genetic variants A23063T and/or G23012A and optionally G22813T of SARS-CoV-2 wildtype or a fragment thereof is present in said sample, preferably by determining whether a fluorescent signal of said fluorophore has become detectable.
Optionally, the samples are additionally contacted with control probes.

Preferably, mutant probes (A) and (J) and optionally (D) and optionally present wildtype probes (A) and (J) and (D) are distinguishably labeled.

DETAILED DESCRIPTION OF THE INVENTION

Figure 1:
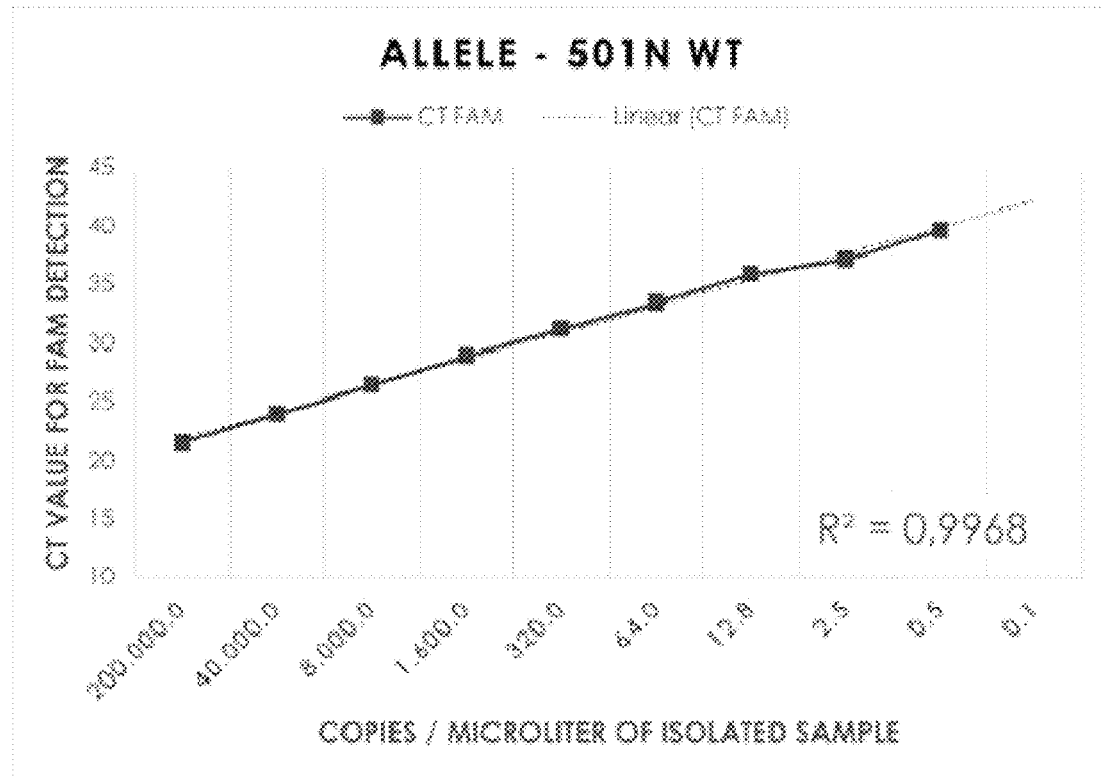
FIG. 1 shows the limits of detection of the qPCR method for SARS-CoV-2 wildtype.

As used herein, unless otherwise stated, the singular forms "a," "an," and "the" include plural reference. Thus, for example, a reference to "an oligonucleotide" includes a plurality of oligonucleotide molecules, and a reference to "a nucleic acid" is a reference to one or more nucleic acids.

As used herein, "about" means plus or minus 10% unless otherwise indicated.

As used herein, the term "sample" or "test sample" may include clinical samples, isolated nucleic acids, or isolated microorganisms. In preferred embodiments, a sample is obtained from a biological source (i.e., a "biological sample"), such as tissue, bodily fluid, or microorganisms collected from a subject. Sample sources include, but are not limited to, mucus, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). The term "patient sample" as used herein refers to a sample obtained from a human seeking diagnosis and/or treatment of a disease. Preferred sample sources include nasal swabs or washes.

"Genomic nucleic acid" or "genomic DNA" refers to some or all of the DNA from a chromosome. Genomic DNA may be intact or fragmented (e.g. digested with restriction endonucleases by methods known in the art). In some embodiments, genomic DNA may include sequence from all or a portion of a single gene or from multiple genes. In contrast, the term "total genomic nucleic acid" is used herein to refer to the full complement of DNA contained in the genome. Methods of purifying DNA and/or RNA from a variety of samples are well-known in the art.

As used herein, the term "oligonucleotide" refers to a short polymer composed of deoxyribonucleotides, ribonucleotides or any combination thereof.

Oligonucleotides are generally between about 10, 11, 12, 13, 14 or 15 to about 150 nucleotides in length, more preferably about 10, 11, 12, 13, 14, or 15 to about 70 nucleotides, and most preferably between about 15 to about 40 nucleotides in length. The single letter code for nucleotides is as described in the U.S. Patent Office Manual of Patent Examining Procedure, section 2422, table 1. In this regard, the nucleotide designation "R" means purine such as guanine or adenine, "Y" means pyrimidine such as cytosine or thymidine (uracil if RNA); and "M" means adenine or cytosine. An oligonucleotide may be used as a primer or as a probe.

The term "target nucleic acid" or "target sequence" as used herein refers to a sequence which includes a segment of nucleotides of interest to be amplified and detected. Copies of the target sequence which are generated during the amplification reaction are referred to as amplification products, amplimers, or amplicons. Target nucleic acid may be composed of segments of a chromosome, a complete gene with or without intergenic sequence, segments or portions of a gene with or without intergenic sequence, or sequences of nucleic acids for which probes or primers are designed. Target nucleic acids may include a wild-type sequence(s), a mutation, deletion or duplication, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein target nucleic acid may be DNA or RNA extracted from a cell or a nucleic acid copied or amplified therefrom, or may include extracted nucleic acids further converted using a bisulfite reaction.

A "fragment" in the context of a nucleic acid refers to a sequence of nucleotide residues which are at least about 5 nucleotides, at least about 7 nucleotides, at least about 9 nucleotides, at least about 11 nucleotides, or at least about 15 nucleotides. The fragment is typically less than about 300 nucleotides, less than about 100 nucleotides, less than about 75 nucleotides, less than about 50 nucleotides, or less than 40 nucleotides. In certain embodiments, the fragments can be used in polymerase chain reaction (PCR), various hybridization procedures, or microarray procedures to identify or amplify identical or related parts of mRNA or DNA molecules. A fragment or segment may uniquely identify each polynucleotide sequence of the present invention.

As used herein, the term "substantially identical", when referring to a nucleic acid, is one that has at least 80%, 85%, 90%, 95%, or 99% sequence identify to a reference nucleic acid sequence. The length of comparison is preferably the full length of the nucleic acid, but is generally at least 15 nucleotides, 20 nucleotides, 30 nucleotides, 40 nucleotides, 50 nucleotides, 75 nucleotides, 100 nucleotides, 125 nucleotides, or more.

By "isolated", when referring to a nucleic acid (e.g., an oligonucleotide) is meant a nucleic acid that is apart from a substantial portion of the genome in which it naturally occurs. For example, any nucleic acid that has been produced synthetically (e.g., by serial base condensation) is considered to be isolated. Likewise, nucleic acids that are recombinantly expressed, produced by a primer extension reaction (e.g., PCR), or otherwise excised from a genome are also considered to be isolated.

The term "complement" "complementary" or "complementarity" as used herein with reference to polynucleotides (i.e., a sequence of nucleotides such as an oligonucleotide or a target nucleic acid) refers to standard Watson/Crick pairing rules. The complement of a nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in natural nucleic acids may be included in the nucleic acids described herein; these include, for example, inosine, 7-deaza-guanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA.

The term "substantially complementary" as used herein means that two sequences specifically hybridize (defined below). The skilled artisan will understand that substantially complementary sequences need not hybridize along their entire length.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid also is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% or 100% sequence identity. Sequence identity can be determined using a commercially available computer program with a default setting that employs algorithms well known in the art (e.g., BLAST). As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Equations for calculating $T_m$ and conditions for nucleic acid hybridization are known in the art.

Oligonucleotides used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

The term "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplicon" or "amplification product". While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods (see, e.g., Saiki, "Amplification of Genomic DNA" in PCR Protocols, Innis et al., Eds., Academic Press, San Diego, CA 1990, pp 13-20; Wharam, et al., Nucleic Acids Res. 29(11):E54-E54 (2001); Hafner, et al., Biotechniques 30(4):852-856, 858, 860 (2001); Zhong, et al., Biotechniques 30(4):852-856, 858, 860 (2001)).

As used herein, the term "detecting" used in the context of detecting a signal from a detectable label to indicate the presence of a target nucleic acid in the sample does not require the method to provide 100% sensitivity and/or 100% specificity. As is well known, "sensitivity" is the probability that a test is positive, given that the subject has a target nucleic acid sequence, while "specificity" is the probability that a test is negative, given that the subject does not have the target nucleic acid sequence. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

As used herein, a "primer" for amplification is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal expression and/or amplification. The term "primer" as used herein includes all forms of primers that may be synthesized including peptide nucleic acid primers, locked nucleic acid primers, phosphorothioate-modified primers, labeled primers, and the like. As used herein, a "forward primer" is a primer that is complementary to the anti-sense strand of dsDNA. A "reverse primer" is complementary to the sense-strand of dsDNA. A "primer pair" refers to the combination of a forward primer and a reverse primer, each specific for the same target nucleic acid. As used herein, "Scorpion primer" or "Scorpion probe" refers to an oligonucleotide having a 3' primer with a 5' extended probe tail having a hairpin structure which possesses a fluorophore/quencher pair. Optionally, the Scorpion primer/probe further contains an amplification blocker (e.g., hexethylene glycol ("HEG") separating the probe moiety from the primer moiety.

As used herein, the term "Scorpion detection system" refers to a method for real-time PCR. This method utilizes a bi-functional molecule (referred to herein as a "Scorpion"), which contains a PCR primer element covalently linked by a polymerase-blocking group to a probe element. Additionally, each Scorpion molecule contains a fluorophore that interacts with a quencher to reduce the background fluorescence.

As used herein "TaqMan® PCR detection system" refers to a method for real time PCR. In this method, a TaqMan® probe which hybridizes to the nucleic acid segment amplified is included in the PCR reaction mix. The TaqMan® probe includes a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

By "primer extension reaction" is meant a synthetic reaction in which an oligonucleotide primer hybridizes to a target nucleic acid and a complementary copy of the target nucleic acid is produced by the polymerase-dependent 3'-addition of individual complementary nucleotides. In preferred embodiments, the primer extension reaction is PCR.

The term "multiplex primer extension reaction" as used herein refers to a primer extension reaction that is capable of simultaneously producing complementary copies of two or more target nucleic acids within the same reaction vessel. Each reaction product is primed using a distinct primer pair. A multiplex reaction may further include specific probes for each product that are detectably labeled with different detectable moieties. In preferred embodiments, the multiplex primer extension reaction is a multiplex PCR in which two or more products within the same reaction vessel are amplified.

By "suitable for amplifying," when referring to oligonucleotide primer or primer pairs, is meant primers that specifically hybridize to a target nucleic acid and are capable of providing an initiation site for a primer extension reaction in which a complementary copy of the target nucleic acid is synthesized.

In a further aspect, the invention provides target nucleic acids for pathogens capable of causing SARS-CoV-2, influenza A, and/or influenza B. Specifically, the invention provides isolated nucleic acid(s) that are at least about 90% identical (e.g., about 95% identical, about 99% identical, or 100% identical) to at least 20 contiguous nucleotides (e.g., 25, 30, 35, 40, 50, 75, 90, or more) of the target sequences referred to in Tables 1 to 10 or complements thereof. In a preferred embodiment, the target nucleic acids are less than about 300, 250, 200, 175, 150, or 125 contiguous nucleotides in length. In one preferred embodiment, the target nucleic acids contain a nucleotide sequence that is substantially identical to at least 20 contiguous nucleotides of the target sequences referred to in Tables 1 to 10, or complements thereof.

The oligonucleotide probe is preferably labeled with a detectable fluorescent marker.

In certain preferred embodiments of the above aspects, one or more of the primers suitable for amplifying the genes or fragments is a Scorpion primer. Preferably, the Scorpion primer includes an oligonucleotide probe sequence and an oligonucleotide primer sequence each of which individually conform to the requirements of an oligonucleotide primer and probe, respectively. More preferably, the Scorpion primers have the sequence of SEQ ID NOs: XZ, 15, 19, or complements thereof.

In some preferred embodiments of the above aspects, the primers and probes of the invention are 10-50 (e.g., 12, 14, 16, 18, 20, 22, 25, 30, 35, 40, or 45) nucleotides in length and are substantially identical, preferably 100% identical to the corresponding sequences of reflected in Tables 1 to 10, or complements thereof.

In preferred embodiments, the probe is an oligonucleotide complementary to the target sequence.

In other preferred embodiments of the above aspects, the gene fragments consist of at least 15, at least 20, at least 30, at least 40, at least 50, at least 75, at least 100 nucleotides that have a nucleotide sequence that is substantially identical or identical to the nucleotide sequence of the reference gene.

It is recognized that any of the foregoing genes or fragments may be assayed individually to identify the individual mutants of SARS-CoV-2, or may be assayed in combination with each other Furthermore, any of the foregoing methods, alone or in combination with clinical evaluation or other diagnostic methods (e.g. lung X-ray), may be used to diagnose an individual as having SARS-CoV-2 or mutants thereof. Units, prefixes, and symbols may be denoted in their accepted SI form.

Unless otherwise indicated, nucleic acids are written left to right in 5' to 3' orientation; amino acid sequences are written left to right in amino to carboxy orientation. Amino acids may be referred to herein by either their commonly known three letter symbols or by the one-letter symbols recommended by the IUP AC-IUBMB Nomenclature Commission. Nucleotides, likewise, may be referred to by their commonly accepted single-letter codes.

Biological Sample Collection and Preparation

Specimens from which target nucleic acids can be detected and quantified with the methods of the present invention are from sterile and/or non-sterile sites. Sterile sites from which specimens can be taken are body fluids such as blood (whole blood, serum, plasma), urine, cerebrospinal fluid (CSF), synovial fluid, pleural fluid, pericardial fluid, intraocular fluid, tissue biopsies or endotracheal aspirates. Non-sterile sites from which specimens can be taken are e.g., sputum, stool, swabs from e.g. skin, inguinal, nasal, pharyngeal and/or throat.

In one embodiment, the method provides for the extraction of nucleic acids from the subject's nasal cavity for use as the testing template followed by one-step RT-PCR using reverse transcription to convert target RNA to cDNA followed by the simultaneous amplification and detection of the target template.

The nucleic acid (DNA and/or RNA) may be isolated from the sample according to any methods well known to those of skill in the art. If necessary, the sample may be collected or concentrated by centrifugation and the like. The cells of the sample may be subjected to lysis, such as by treatment with enzymes, heat surfactants, ultrasonication or a combination thereof. The lysis treatment is performed in order to obtain a sufficient amount of DNA derived from the viral pathogens, if present in the sample, to detect using polymerase chain reaction.

Various methods of DNA extraction are suitable for isolating the DNA. Suitable methods include phenol and chloroform extraction (see Maniatis et al., Molecular Cloning, A Laboratory Manual, 2d, Cold Spring Harbor Laboratory Press, page 16.54 (1989)). Numerous commercial kits also yield suitable DNA including, but not limited to, QIAamp™ mini blood kit, QIAamp™ Mini Viral RNA kit, Agencourt Genfind™, Roche Cobas© Roche MagNA Pure© or phenol xhloro form extraction using Eppendorf Phase Lock Gels®.

In one embodiment, a nucleic acid isolation step is used that isolates both RNA and DNA in one reaction. In an alternate embodiment, RNA and DNA may be isolated independently and then combined for use in the methods of the invention. In yet another alternate embodiment, when only one type of nucleic acid is required to be isolated (such as when all the disease agents and secondary disease agents of interest have the same type of nucleic acid genome), nucleic acid isolation methods that isolate only RNA or DNA may be used. The nucleic acid isolation techniques and protocols described herein may be used to isolate nucleic acid from a variety of patient samples or sources.

In one embodiment, a dual RNA/DNA isolation method is used employing a trizol based reagent for initial isolation of RNA and DNA from patient samples. Upon contact with patient samples, the phenol and high salt reagents in the trizol effectively inactivate any disease agent or secondary disease agent that may be present in the patient sample. In order to allow for the dual isolation of RNA and DNA in the same phase with a single step, the pH of the trizol solution may be adjusted towards neutral (instead of acidic). After the RNA and DNA are isolated from the patient samples, a silica-based column may be used to further isolate the RNA and DNA. The use of silica-based columns allows for wash steps to be performed quickly and efficiently while minimizing the possibility of contamination. The wash steps may be used to remove PCR and RT-PCR inhibitors. The column method for nucleic acid purification is advantageous as it can be used with different types of patient samples and the spin and wash steps effectively remove PCR or RT-PCR inhibitors. In one embodiment, the nucleic isolation is earned out using the dual RNA/DNA isolation kit provided by QIAamp® Viral RNA Mini Spin Kit (Qiagen, Valencia, CA).

Target Nucleic Acids and Primers

In various embodiments of the present invention, oligonucleotide primers and probes are used in the methods described herein to amplify and detect target sequences of SARS-CoV-2 and/or mutants thereof. In certain preferred embodiments, target nucleic acids include the S gene COVID-19 genome. In addition, primers can also be used to amplify one or more control nucleic acid sequences The target nucleic acids described herein may be detected singly or in a multiplex format, utilizing individual labels for each target.

The skilled artisan is capable of designing and preparing primers that are appropriate for amplifying a target sequence in view of this disclosure. The length of the amplification primers for use in the present invention depends on several factors including the nucleotide sequence identity and the temperature at which these nucleic acids are hybridized or used during in vitro nucleic acid amplification.

Primers that amplify a nucleic acid molecule can be designed using, for example, a computer program such as OLIGO (Molecular Biology Insights, Inc., Cascade, CO). Important features when designing oligonucleotides to be used as amplification primers include, but are not limited to, an appropriate siVe amplification product to facilitate detection (e.g., by electrophoresis or real-time PCR), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 15 to 40 nucleotides in length.

Designing oligonucleotides to be used as hybridization probes can be performed in a manner similar to the design of primers. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally 15 to 60 nucleotides in length.

Amplification of Nucleic Acids

Nucleic acid samples or target nucleic acids may be amplified by various methods known to the skilled artisan. Preferably. PCR is used to amplify nucleic acids of interest. Briefly, in PCR, two primer sequences are prepared that are complementary to regions on opposite complementary strands of the marker sequence. An excess of deoxynucleotide triphosphates are added to a reaction mixture along with a DNA polymerase, e.g., Taq polymerase.

If the target sequence is present in a sample, the primers will bind to the sequence and the polymerase will cause the primers to be extended along the target sequence by adding on nucleotides. By raising and lowering the temperature of the reaction mixture, the extended primers will dissociate from the target nucleic acid to form reaction products, excess primers will bind to the target nucleic acid and to the reaction products and the process is repeated, thereby generating amplification products. Cycling parameters can be varied, depending on the length of the amplification products to be extended. An internal positive amplification control can be included in the sample, utilizing oligonucleotide primers and/or probes. The control can be used to monitor both the conversion process and any subsequent amplification.

In a suitable embodiment, PCR is performed using a Scorpion primer/probe combination. Scorpion probes, as used in the present invention include a 3' primer with a 5' extended probe tail having a hairpin structure which possesses a fluorophore/quencher pair.

The probe tail is "protected" from replication in the 5' to 3' direction by the inclusion of hexethylene glycol (HEG) which blocks the polymerase from replicating the probe. During the first round of amplification the 3' target-specific primer anneals to the target and is extended such that the Scorpion is now incorporated into the newly synthesized strand, which possesses a newly synthesized target region for the 5' probe. During the next round of denaturation and annealing, the probe region of the Scorpion hairpin loop will hybridize to the target, thus separating the fluorophore and quencher and creating a measurable signal. Such probes are described in Whitcombe et al., Nature Biotech 17:804-807 (1999).

In one embodiment, the target nucleic acids are amplified in a multiplex amplification reaction. This is typically applied for the detection of two or more mutants. A variety of multiplex amplification strategies are known in the art and may be used with the methods of the invention. The multiplex amplification strategy may use PCR, RT-PCR or a combination thereof depending on the type of nucleic acid. For example, if an RNA genome is present, RT-PCR may be utilized. The PCR enzyme may be an enzyme with both a reverse transcription and polymerase function. Furthermore, the PCR enzyme may be capable of "hot start" reactions as is known in the art.

Detection of Amplified Nucleic Acids

Amplification of nucleic acids can be detected by any of a number of methods well-known in the art such as gel electrophoresis, column chromatography, hybridization with a probe, sequencing, melting curve analysis, or "real-time" detection.

In one approach, sequences from two or more fragments of interest are amplified in the same reaction vessel (i.e. "multiplex PCR") Detection can take place by measuring the end-point of the reaction or in "real time." For real-time detection, primers and/or probes may be detectably labeled to allow differences in fluorescence when the primers become incorporated or when the probes are hybridized, for example, and amplified m an instrument capable of monitoring the change in fluorescence during the reaction Real-time detection methods for nucleic acid amplification are well known and include, for example, the TaqMan© system, the Scorpion bi-functional molecule, and the use of intercalating dyes for double stranded nucleic acid.

In end-point detection, the amplicon(s) could be detected by first size-separating the amplicons, then detecting the size-separated amplicons. The separation of amplicons of different sizes can be accomplished by, for example, gel electrophoresis, column chromatography, or capillary electrophoresis. These and other separation methods are well-known in the art. In one example, amplicons of about 10 to about 150 base pairs whose sizes differ by 10 or more base pairs can be separated, for example, on a 4% to 5% agarose gel (a 2% to 3% agarose gel for about 150 to about 300 base pair amplicons), or a 6% to 10% polyacrylamide gel The separated nucleic acids can then be stained with a dye such as ethidium bromide and the size of the resulting stained band or bands can be compared to a standard DNA ladder.

In another embodiment, two or more fragments of interest are amplified in separate reaction vessels If the amplification is specific, that is, one primer pair amplifies for one fragment of interest but not the other, detection of amplification is sufficient to distinguish between the two types—size separation would not be required.

In some embodiments, amplified nucleic acids are detected by hybridization with a specific probe. Probe oligonucleotides, complementary to a portion of the amplified target sequence may be used to detect amplified fragments. Hybridization may be detected in real time or in non-real time. Amplified nucleic acids for each of the target sequences may be detected simultaneously (i.e., in the same reaction vessel) or individually (i.e., in separate reaction vessels). In preferred embodiments, the amplified DNA is detected simultaneously, using two or more distinguishably-labeled, gene-specific oligonucleotide probes, one which hybridizes to the first target sequence, one which hybridizes to the second target sequence, and so forth.

The probe may be detectably labeled by methods known in the art. Useful labels include, e.g., fluorescent dyes (e.g., Cy5©, Cy3©, FITC, rhodamine, lanthamide phosphors, Texas red, FAM, JOE, Cal Fluor Red 610©, Quasar 670©), $^{32}P$, $^{35}S$, $^{3}H$, $^{14}C$, $^{125}I$, $^{131}I$, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected.

One general method for real time PCR uses fluorescent probes such as the TaqMan® probes, molecular beacons, and Scorpions. Real-time PCR quantitates the initial amount of the template with more specificity, sensitivity and reproducibility, than other forms of quantitative PCR, which detect the amount of final amplified product. Real-time PCR does not detect the size of the amplicon. The probes employed in Scorpion and TaqMan® technologies are based on the principle of fluorescence quenching and involve a donor fluorophore and a quenching moiety.

In a preferred embodiment, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher.

As a result of donating energy to the quencher moiety, the donor fluorophore will itself emit less light at a particular emission frequency than it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and Scorpion type probes.

In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a longer wavelength. Proximal quenching requires very close positioning of the donor and quencher moiety, while FRET quenching, also distance related, occurs over a greater distance (generally 1-10 nm, the energy transfer depending on R-6, where R is the distance between the donor and the acceptor). Thus, when FRET quenching is involved, the quenching moiety is an acceptor fluorophore that has an excitation frequency spectrum that overlaps with the donor emission frequency spectrum.

When quenching by FRET is employed, the assay may detect an increase in donor fluorophore fluorescence resulting from increased distance between the donor and the quencher (acceptor fluorophore) or a decrease in acceptor fluorophore emission resulting from decreased distance between the donor and the quencher (acceptor fluorophore).

Suitable fluorescent moieties include the following fluorophores known in the art: 4-acetamido-4'-isothiocyanatostilbene-2,2'disulfonic acid, acridine and derivatives (acridine, acridine isothiocyanate) Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes), 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Black Hole Quencher™ (BHQ™) dyes (biosearch Technologies), BOD1 PY® R-6G, BOP IPY® 530/550, BODIPY® FL, Brilliant Yellow, coumarin and derivatives (coumarin, 7-amino-4-methylcoumarin (AMC, Coumarin 120), 7-amino-4-trifluoromethylcouluarin (Coumarin 151)), Cy2©, Cy3©, Cy3.5©, Cy5©, Cy5.5©, cyanosine, 4',6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, diethylene-triamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansylchloride), 4-(4'-dimethylaminophenylazo)benzoic acid (DABCYL), 4-dimethylaminophenylazophenyl-4'-isothiocyanate (DABITC), Eclipse™ (Epoch Biosciences Inc.), eosin and derivatives (eosin, eosin isothiocyanate), erythrosin and derivatives (erythrosin B, erythrosin isothiocyanate), ethidium, fluorescein and derivatives (5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachloro-fluorescein (TET)), fluorescamine, IRI 44, IRI 446, Malachite Green isothiocyanate, 4-methyl-umbelliferone, ortho cresolphthalein, nitrotyrosine, pararosaniline, Phenol Red, B-phycoerythrin, R-phycoerythrin, o-phthaldialdehyde, Oregon Green©, propidium iodide, pyrene and derivatives (pyrene, pyrene butyrate, succinimidyl-1-pyrene butyrate), QSY© 7, QSY® 9, QSY® 21, QSY® 35 (Molecular Probes), Reactive Red 4 (Cibacron® Brilliant Red 3B-A), rhodamine and derivatives (6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, sulforhodamine B, sulforhodamine 101, sulfonyl chloride derivative of sulforhodamine 101 (Texas Red)), N,N,N',N'-tctramethyl-6-carboxyrhodamine (TAMRA), tetramethyl rhodamine, tetramethyl rhodamine isothiocyanate (TRITC), riboflavin, rosolic acid, terbium chelate derivatives.

Other fluorescent nucleotide analogs can be used (see, e.g., Jameson, Meth. Enzymol. 278:363-390 (1997); Zhu, Nucl. Acids Res. 22:3418-3422 (1994)). U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

Suitable quenchers are selected based on the fluorescence spectrum of the particular fluorophore. Useful quenchers include, for example, the Black Hole™ quenchers BHQ-I, BHQ-2, and BHQ-3 (Biosearch Technologies, Inc.), and the ATTO-series of quenchers (ATTO 540Q, ATTO 580Q, and ATTO 612Q; Atto-Tec GmbH).

The detectable label can be incorporated into, associated with or conjugated to a nucleic acid. The label can be attached by spacer aims of various lengths to reduce potential steric hindrance or impact on other useful or desired properties (see, e.g., Mansfield, 9 Mol Cell Probes 145-156 (1995)). Detectable labels can be incorporated into nucleic acids by covalent or non-covalent means, e.g. by transcription, such as by random-primer labeling using Klenow polymerase, or nick translation, or amplification, or equivalent as is known in the art. For example, a nucleotide base is conjugated to a detectable moiety, such as a fluorescent dye, and then incorporated into nucleic acids during nucleic acid synthesis or amplification. In one embodiment, the pathogens are detected in 3 channels.

With Scorpion detection systems, sequence-specific priming and PCR product detection is achieved using a single molecule The Scorpion probe maintains a stem-loop configuration in the unhybridized state. The fluorophore is quenched by a moiety coupled to the 5' end, although in suitable embodiments, the fluorophore is attached to the 5' end and is quenched by a moiety coupled to the 3' end The 3' portion of the stem also contains a sequence that is complementary to the extension product of the primer. This sequence is linked to the 5' end of the Scorpion probe via a non-amplifiable monomer. After extension using the Scorpion primer, the specific probe sequence is able to bind to its complement within the extended amplicon thus opening up the hairpin loop This prevents fluorescence from being quenched and a signal is observed A specific target is amplified by the reverse primer and the primer portion of the Scorpion, resulting m an extension product.

A fluorescent signal is generated due to the separation of the fluorophore from the quencher resulting from the binding of the probe element of the Scorpion to the extension product.

TaqMan® probes (Held, et al, Genome Res 6 986-994, 1996) use the fluorogenic 5' exonuclease activity of Taq polymerase to measure the amount of target sequences in cDNA samples TaqMan® probes are oligonucleotides that contain a donor fluorophore usually at or near the 5' base, and a quenching moiety typically at or near the 3' base The quencher moiety may be a dye such as TAMRA or may be a non-fluorescent molecule such as 4-(4-dimethylaminophenylazo)benzoic acid (DABCYL) (see Tyagi et al., 16 Nature Biotechnology 49-53 (1998)). When irradiated, the excited fluorescent donor transfers energy to the nearby quenching moiety by FRET rather than fluorescing Thus, the close proximity of the donor and quencher prevents emission of donor fluorescence while the probe is intact.

TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

In a suitable embodiment, real time PCR is performed using any suitable instrument capable of detecting fluorescence from one or more fluorescent labels. For example, real time detection on the instrument (e.g., a ABI Prism® 7900HT sequence detector) monitors fluorescence and calculates the measure of reporter signal, or Rn value, during each PCR cycle. The threshold cycle, or Ct value, is the cycle at which fluorescence intersects the threshold value. The threshold value is determined by the sequence detection system software or manually.

Where a fluorescent dye is used to determine the melting temperature of a nucleic acid in the method, the fluorescent dye may emit a signal that can be distinguished from a signal emitted by any other of the different fluorescent dyes that are used to label the oligonucleotides. In some embodiments, the fluorescent dye for determining the melting temperature of a nucleic acid may be excited by different wavelength energy than any other of the different fluorescent dyes that are used to label the oligonucleotides. In some embodiments, the second fluorescent dye for determining the melting temperature of the detected nucleic acid is an intercalating agent. Suitable intercalating agents may include, but are not limited to SYBR™ Green 1 dye, SYBR™ dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO-1, TOTO-I, YOYO-3, TOTO-3, POPO-I, BOBO-I, POPO-3, BOBO-3, LOLO-I, JOJO-I, cyanine dimers, YO-PRO-I, TO-PRO-I, YO-PRO-3, TO-PRO-3, TO-PRO-5, PO-PRO-I, BO-PRO-I, PO-PRO-3, BO-PRO-3, LO-PROI, JO-PRO-I, and mixture thereof. In suitable embodiments, the selected intercalating agent is SYBR™ Green 1 dye.

By detecting the temperature at which the fluorescence signal is lost, the melting temperature can be determined. For example, amplified target nucleic acids may have a melting temperature that differs by at least about 1° C., more preferably by at least about 2° C., or even more preferably by at least about 4° C. from the melting temperature of any other amplified target nucleic acids. By observing differences in the melting temperature(s) of the gene or gene fragment targets from the respective amplification products, one can confirm the presence or absence of the pathogenic genes in the sample.

For various genetic variations of the SARS-CoV-2 wild-type specific systems which can be used for the specific mutants are reflected in Table 1 to 10.

TABLE 1

PCR information for the detection of Mutant N501Y

| Spike Protein

TABLE 1-continued

PCR information for the detection of Mutant N501Y

| | Sequence 5'-3' | SEQ ID |
|---|---|---|
| Target Sequence (A) wildtype | ACTTTCCTTTACAATCATATGGTTTCCAACCCACTAATGGTGTTGGTTACCAACCATACAGAG | NO: 1 |
| Target Sequence (A) Mutant N501Y | ACTTTCCTTTACAATCATATGGTTTCCAACCCACTTATGGTGTTGGTTACCAACCATACAGAG | NO: 2 |
| Forward Primer (A) | ACTTTCCTTTACAATCATATGG | NO: 3 |
| Reverse Primer (A) | CTCTGTATGGTTGGTAACC | NO: 4 |
| Wildtype Probe (A) | TCCAACCCACTAATGGTG | NO: 5 |
| Mutant Probe (A) | TCCAACCCACTTATGGTG | NO: 6 |

TABLE 2

PCR information for the detection of Mutant del HV69/70

| Spike Protein Variation | Genetic Variation | Target Sequence Location at Spike gene (S gene) | Source of Mutant information |
|---|---|---|---|
| del HV69/70 | del21765-770 | 21714 to 21795 | Preliminary genomic characterisation of an emergent SARS-CoV-2 lineage in the UK defined by a novel set of spike mutations - SARS-CoV-2 coronavirus / nCoV-2019 Genomic Epidemiology - Virological |

| | Sequence 5'-3' | SEQ ID |
|---|---|---|
| Target Sequence (B) wildtype | CTCAGGACTTGTTCTTACCTTTCTTTTCCAATGTTACTTGGTTCCATGCTATACATGTCTCTGGGACCAATGGTACTAAGAG | NO: 7 |
| Target Sequence (B) Mutant del HV69/70 | CTCAGGACTTGTTCTTACCTTTCTTTTCCAATGTTACTTGGTTCCATGCTATCTCTGGGACCAATGGTACTAAGAG | NO: 8 |
| Forward Primer (B) | CTCAGGACTTGTTCTTACC | NO: 9 |
| Reverse Primer (B) | CTCTTAGTACCATTGGTCC | NO: 10 |
| Wildtype Probe (B) | TCCATGCTATACATGTCTCT | NO: 11 |
| Mutant Probe (B) | ACTTGGTTCCATGCTATCTCT | NO: 12 |

TABLE 3

PCR information for the detection of Mutant 0614G

| Spike Protein Variation | Genetic Variation | Target Sequence Location at Spike gene (S gene) | Source of Mutant information |
|---|---|---|---|
| D614G | A23403G | 23360 to 23431 | https://doi.org/10.1016/j.ijid.2020.05.071 |

| | Sequence 5'-3' | SEQ ID |
|---|---|---|
| Target Sequence (C) wildtype | CCAGGAACAAATACTTCTAACCAGGTTGCTGTTCTTTATCAGGATGTTAACTGCACAGAAGTCCCTGTTGCT | NO: 13 |
| Target Sequence (C) Mutant D614G | CCAGGAACAAATACTTCTAACCAGGTTGCTGTTCTTTATCAGGGTGTTAACTGCACAGAAGTCCCTGTTGCT | NO: 14 |
| Forward Primer (C) | CCAGGAACAAATACTTCTAACC | NO: 15 |
| Reverse Primer (C) | AGCAACAGGGACTTCTG | NO: 16 |
| Wildtype Probe (C) | TGTTCTTTATCAGGATGTTAACTG | NO: 17 |
| Mutant Probe (C) | TGTTCTTTATCAGGGTGTTAACT | NO: 18 |

TABLE 4

PCR information for the detection of Mutant K417N

| Spike Protein Variation | Genetic Variation | Target Sequence Location at Spike gene (S gene) | Source of Mutant information |
|---|---|---|---|
| K417N | G22813T | 22782 to 22855 | doi: https://doi.org/10.1101/2020.12.23.424283 |

| | Sequence 5'-3' | SEQ ID |
|---|---|---|
| Target Sequence (D) wildtype | TCAGACAAATCGCTCCAGGGCAAACTGGAAAGATTGCTGATTATAATTATAAATTACCAGATGATTTTACAGGC | NO: 19 |
| Target Sequence (D) Mutant K417N | TCAGACAAATCGCTCCAGGGCAAACTGGAAATATTGCTGATTATAATTATAAATTACCAGATGATTTTACAGGC | NO: 20 |
| Forward Primer (D) | TCAGACAAATCGCTCCA | NO: 21 |
| Reverse Primer (D) | GCCTGTAAAATCATCTGGTA | NO: 22 |
| Wildtype Probe (D) | CAAACTGGAAAGATTGCTG | NO: 23 |
| Mutant Probe (D) | CAAACTGGAAATATTGCTG | NO: 24 |

TABLE 5

PCR information for the detection of Mutant P681H

| Spike Protein Variation | Genetic Variation | Target Sequence Location at Spike gene (S gene) | Source of Mutant information |
|---|---|---|---|
| P681H | C23604A | 23566 to 23634 | |

| | Sequence 5'-3' | SEQ ID |
|---|---|---|
| Target Sequence (E) wildtype | AGGTATATGCGCTAGTTATCAGACTCAGACTAATTCTCCTCG GCGGGCACGTAGTGTAGCTAGTCAATC | NO: 25 |
| Target Sequence (E) Mutant P681H | AGGTATATGCGCTAGTTATCAGACTCAGACTAATTCTCATCG GCGGGCACGTAGTGTAGCTAGTCAATC | NO: 26 |
| Forward Primer (E) | AGGTATATGCGCTAGTTATCAGA | NO: 27 |
| Reverse Primer (E) | GATTGACTAGCTACACTACGT | NO: 28 |
| Wildtype Probe (E) | ACTAATTCTCCTCGGCG | NO: 29 |
| Mutant Probe (E) | ACTAATTCTCATCGGCG | NO: 30 |

TABLE 6

PCR information for the detection of Mutant A222V

| Spike Protein Variation | Genetic Variation | Target Sequence Location at Spike gene (S gene) | Source of Mutant information |
|---|---|---|---|
| A222V | C22227T | 22185 to 22264 | doi: https://doi.org/10.1101/2020.11.28.20237016 |

| | Sequence 5'-3' | SEQ ID |
|---|---|---|
| Target Sequence (F) wildtype | CGCCTATTAATTTAGTGCGTGATCTCCCTCAGGGTTTTTCGGCT TTAGAACCATTGGTAGATTTGCCAATAGGTATTAAC | NO: 31 |
| Target Sequence (F) Mutant A222V | CGCCTATTAATTTAGTGCGTGATCTCCCTCAGGGTTTTTCGGTT TTAGAACCATTGGTAGATTTGCCAATAGGTATTAAC | NO: 32 |
| Forward Primer (F) | CGCCTATTAATTTAGTGCGT | NO: 33 |
| Reverse Primer (F) | GTTAATACCTATTGGCAAATCTAC | NO: 34 |
| Wildtype Probe (F) | AGGGTTTTTCGGCTTTAGAAC | NO: 35 |
| Mutant Probe (F) | AGGGTTTTTCGGTTTTAGAAC | NO: 36 |

TABLE 7

PCR information for the detection of Mutant S477N

| Spike Protein Variation | Genetic Variation | Target Sequence Location at Spike gene (S gene) | Source of Mutant information |
|---|---|---|---|
| S477N | G22992A | 22956 to 23037 | doi: https://doi.org/10.1101/2020.10.25.20219063 |

| | Sequence 5'-3' | SEQ ID |
|---|---|---|
| Target Sequence (G) wildtype | AGAGAGATATTTCAACTGAAATCTATCAGGCCGGTAGCACACC TTGTAATGGTGTTGAAGGTTTTAATTGTTACTTTCCTTT | NO: 37 |
| Target Sequence (G) Mutant S477N | AGAGAGATATTTCAACTGAAATCTATCAGGCCGGTAACACACC TTGTAATGGTGTTGAAGGTTTTAATTGTTACTTTCCTTT | NO: 38 |
| Forward Primer (G) | AGAGAGATATTTCAACTGAAATCT | NO: 39 |
| Reverse Primer (G) | AAAGGAAAGTAACAATTAAAACCT | NO: 40 |
| Wildtype Probe (G) | AGGCCGGTAGCACAC | NO: 41 |
| Mutant Probe (G) | AGGCCGGTAACACAC | NO: 42 |

TABLE 8

PCR information for the detection of Mutant V1176F

| Spike Protein Variation | Genetic Variation | Target Sequence Location at Spike gene (S gene) | Source of Mutant information |
|---|---|---|---|
| V1176F | G25088T | 25046 to 25123 | DOI: 10.1101/2020.05.21.108563 |

| | Sequence 5'-3' | SEQ ID |
|---|---|---|
| Target Sequence (H) wildtype | CCAGATGTTGATTTAGGTGACATCTCTGGCATTAATGCTTCAGT TGTAAACATTCAAAAAGAAATTGACCGCCTCAAT | NO: 43 |
| Target Sequence (H) Mutant V1176F | CCAGATGTTGATTTAGGTGACATCTCTGGCATTAATGCTTCATT TGTAAACATTCAAAAAGAAATTGACCGCCTCAAT | NO: 44 |
| Forward Primer (H) | CCAGATGTTGATTTAGGTGAC | NO: 45 |
| Reverse Primer (H) | ATTGAGGCGGTCAATTTC | NO: 46 |
| Wildtype Probe (H) | TGGCATTAATGCTTCAGTTGTAAA | NO: 47 |
| Mutant Probe (H) | TGGCATTAATGCTTCATTTGTAAA | NO: 48 |

TABLE 9

PCR information for the detection of Mutant N439K

| Spike Protein Variation | Genetic Variation | Target Sequence Location at Spike gene (S gene) | Source of Mutant information |
|---|---|---|---|
| N439K | C22879A | 22840 to 22916 | DOI: https://doi.org/10.1016/j.cell.2021.01.037 |

| | Sequence 5'-3' | SEQ ID |
|---|---|---|
| Target Sequence (I) wildtype | AGATGATTTTACAGGCTGCGTTATAGCTTGGAATTCTAACAATC TTGATTCTAAGGTTGGTGGTAATTATAATTACC | NO: 49 |
| Target Sequence (I) Mutant N439K | AGATGATTTTACAGGCTGCGTTATAGCTTGGAATTCTAAAAATC TTGATTCTAAGGTTGGTGGTAATTATAATTACC | NO: 50 |
| Forward Primer (I) | AGATGATTTTACAGGCTGC | NO: 51 |
| Reverse Primer (I) | GGTAATTATAATTACCACCAACCT | NO: 52 |
| Wildtype Probe (I) | TAGCTTGGAATTCTAACAATCTTGA | NO: 53 |
| Mutant Probe (I) | TAGCTTGGAATTCTAAAAATCTTGA | NO: 54 |

TABLE 10

PCR information for the detection of Mutant E484K

| Spike Protein Variation | Genetic Variation | Target Sequence Location at Spike gene (S gene) | Source of Mutant information |
|---|---|---|---|
| E484K | G23012A | 22956 to 23049 | doi: https://doi.org/10.1101/2021.01.26.21250224 |

| | Sequence 5'-3' | SEQ ID |
|---|---|---|
| Target Sequence (J) wildtype | AGAGAGATATTTCAACTGAAATCTATCAGGCCGGTAGCACAC CTTGTAATGGTGTTGAAGGTTTTAATTGTTACTTTCCTTTACAA TCATATGG | NO: 55 |
| Target Sequence (J) Mutant E484K | AGAGAGATATTTCAACTGAAATCTATCAGGCCGGTAGCACAC CTTGTAATGGTGTTAAAGGTTTTAATTGTTACTTTCCTTTACAA TCATATGG | NO: 56 |
| Forward Primer (J) | AGAGAGATATTTCAACTGAAATCT | NO: 57 |
| Reverse Primer (J) | CCATATGATTGTAAAGGAAAGTAAC | NO: 58 |
| Wildtype Probe (J) | TTGTAATGGTGTTGAAGGTTTTA | NO: 59 |
| Mutant Probe (J) | TTGTAATGGTGTTAAAGGTTTTA | NO: 60 |

The present invention is directed to methods for assaying for the presence of SARS-CoV-2 and SARS-CoV-2 mutants in a sample, including a clinical sample, and to oligonucleotides, reagents and kits useful in such assays. In particular, the present invention is directed to such assays that are rapid, accurate and specific for the detection of SARS-CoV-2.

As used herein, an assay for the detection of SARS-CoV-2 is preferably said to be "specific" for SARS-CoV-2 if it can be conducted under conditions that permit it to detect SARS-CoV-2 without exhibiting cross-reactivity to human DNA, or to DNA (or cDNA) of other pathogens, especially other coronavirus pathogens. In particular, an assay for the detection of SARS-CoV-2 is said to be specific for SARS-CoV-2 if it can be conducted under conditions that permit it to detect SARS-CoV-2 without exhibiting cross-reactivity to DNA (or cDNA) of Influenza A, Influenza B, Respiratory Syncytial Virus, Group A *Streptococcus* (*Streptococcus pyogenes*), Parainfluenza I, Parainfluenza III, *Haemophilus parainfluenzae*, Enterovirus or Adenovirus, or to SARS-CoV, MERS-CoV, or bat-derived Severe Acute Respiratory Syndrome-like coronaviruses, such as bat-SL-CoVZC45 or bat-SL-CoVZXC21. More preferably, an assay for the detection of SARS-CoV-2 is said to be specific for SARS-CoV-2 if it can be conducted under conditions that permit it to detect SARS-CoV-2 without exhibiting cross-reactivity to DNA (or cDNA) of Adenovirus 1, *Bordetella pertussis*, *Chlamydophila pneumoniae*, Coronavirus 229E, Coronavirus NL63, Coronavirus OC43, Enterovirus 68, *Haemophilus influenzae*, Human metapneumovirus (hMPV-9), Influenza A H3N2 (Hong Kong 8/68), Influenza B (Phuket 3073/2013), *Legionella* pneumophilia, MERS-Coronavirus, *Mycobacterium tuberculosis*, Parainfluenza Type 1, Parainfluenza Type 2, Parainfluenza Type 3, Parainfluenza Type 4A, Rhinovirus B14, RSV A Long, RSV B Washington, SARS-Coronavirus, SARS-Coronavirus HKU39849, *Streptococcus pneumoniae, Streptococcus pyogenes*, human leukocytes, or pooled human nasal fluid.

Further, the assay or methods of the present invention are usually "specific" in the that variants of SARS-CoV-2 wildtype can be distinguished from each other and from the wildtype respectively.

As used herein, an assay for the detection of SARS-CoV-2 is preferably said to be "accurate" for SARS-CoV-2 if it is capable of detecting a viral dose of 400 copies/ml of SARS-CoV-2 with an LoD of at least 80%, and of detecting a viral dose of 500 copies/ml of SARS-CoV-2 with an LoD of at least 90%.

As used herein, an assay for the detection of SARS-CoV-2 is said to be "rapid" for SARS-CoV-2 if it is capable of providing a determination of the presence or absence of SARS-CoV-2 preferably within 2 hours, and more preferably within 90 minutes and most preferably, within 1 hour after the commencement of the assay.

III. Preferred Assays for the Detection of SARS-CoV-2 and Mutants of SARS-CoV-2

A. Preferred Assay Formats

The present invention provides an assay for detecting the presence of SARS-CoV-2 in a sample, preferably a clinical sample. Such detection may be accomplished in situ or in vitro, but is preferably conducted in vitro. The clinical samples that may be evaluated include any that may contain SARS-CoV-2 or mutants thereof, and include blood samples, bronchoalveolar lavage fluid specimens, fecal samples, fibrobronchoscope brush biopsy samples, nasal swab samples, nasopharyngeal swab samples, pharyngeal swab sample, sputum samples and urine samples.

Preferably, however, the employed sample will be a nasal swab sample, a nasopharyngeal swab sample, a pharyngeal swab sample, or a sputum sample, and most preferably, the employed clinical sample will be a nasopharyngeal swab sample. In one embodiment, the sample will be pre-treated to extract RNA that may be present in the sample. Alternatively, and more preferably, the sample will be evaluated without prior RNA extraction.

The present invention preferably uses a real-time reverse transcriptase polymerase chain reaction (rRT-PCR) assay to detect the presence of SARS-CoV-2 and/or mutants of SARS-CoV in clinical samples. rRT-PCR assays are well known and widely deployed in diagnostic virology (see, e.g., Pang, J. et al. (2020) "Potential Rapid Diagnostics, Vaccine and Therapeutics for 2019 Novel Coronavirus (2019-nCoV): A Systematic Review," J. Clin. Med. 26; 9(3)E623 doi: 10.3390/jcm9030623; Kralik, P. et al. (2017) "A Basic Guide to Real-Time PCR in Microbial Diagnostics: Definitions, Parameters, and Everything," Front. Microbiol. 8:108. doi: 10.3389/fmicb.2017.00108).

To more easily describe the rRT-PCR assays of the present invention, such assays may be envisioned as involving multiple reaction steps:

(1) the reverse transcription of SARS-CoV-2 RNA that may be present in the clinical sample that is to be evaluated for SARS-CoV-2 or mutants of SARS-CoV-2 presence;

(2) the PCR-mediated amplification of the SARS-CoV-2 cDNA produced from such reverse transcription;

(3) the hybridization of SARS-CoV-2-specific probes to such amplification products; (4) the double-strand-dependent 5"→3" exonuclease cleavage of the hybridized SARS-CoV-2-specific probes; and (5) the detection of the unquenched probe fluorophores signifying that the evaluated clinical sample contained SARS-CoV-2.

It will be understood that such steps may be conducted separately (for example, in two or more reaction chambers, or with reagents for the different steps being added at differing times, etc.). However, it is preferred that such steps are to be conducted within the same reaction chamber, and that all reagents needed for the rRT-PCR assays of the present invention are to be provided to the reaction chamber at the start of the assay. It will also be understood that although the polymerase chain reaction (PCR) (see, e.g. Ghannam, M. G. et al. (2020) "Biochemistry, Polymerase Chain Reaction (PCR)," StatPearls Publishing, Treasure Is.; pp 0.1-4; Lorenz, T. C. (2012) "Polymerase Chain Reaction: Basic Protocol Plus Troubleshooting And Optimization Strategies," J. Vis. Exp. 2012 May 22; (63):e3998; pp. 1-15) is the preferred method of amplifying SARS-CoV-2 cDNA produced via reverse transcription, other DNA amplification technologies could alternatively be employed.

Accordingly, in a preferred embodiment, the rRT-PCR assays of the present invention comprise incubating a clinical sample in the presence of a DNA polymerase, a reverse transcriptase, one pair of specific primers for the SARS-CoV-2 wildtype and the mutant of SARS-CoV-2, preferably two probes which are specific for SARS-CoV-2 wildtype and the respective mutant thereof, (typically, at least one probe for the SARS-CoV-2 wildtype and one probe for the mutant of the SARS-CoV-2 wildtype for each region being amplified by an employed pair of primers), deoxynucleotide triphosphates (dNTPs) and buffers. The conditions of the incubation are cycled to permit the reverse transcription of SARS-CoV-2 RNA, the amplification of SARS-CoV-2 cDNA, the hybridization of SARS-CoV-2 or mutants of SARS-CoV-2-specific probes to such cDNA, the cleavage of the hybridized SARS-CoV-2-specific probes or mutant of SARS-CoV-2-specific probes and the detection of unquenched probe fluorophores.

The rRT-PCR assays of the present invention employs at least one set of at least one "Forward" primer that hybridizes to a polynucleotide portion of a first strand of a DNA molecule, and at least one "Reverse" primer that hybridizes to a polynucleotide portion of a second (and complementary) strand of such DNA molecule.

Preferably, such Forward and Reverse primers will permit the amplification of a region a region of the S gene (spike gene), which encodes the virus spike surface glycoprotein and is required for host cell targeting; the SARS-CoV-2 spike surface glycoprotein is a key protein for specifically characterizing a coronavirus as being SARS-CoV-2 (Chen, Y. et al. (2020) "Structure Analysis Of The Receptor Binding Of 2019-Ncov," Biochem. Biophys. Res. Commun. 525: 135-140; Masters, P. S. (2006) "The Molecular Biology Of Coronaviruses," Adv. Virus Res. 66:193-292).

The amplification of the targets alone is sufficient for the specific determination of SARS-CoV-2 or a specific mutant of the SARS-CoV-2 in samples. It is, however, preferred to assay for SARS-CoV-2 by amplifying both such targets.

The presence of such amplified molecules is preferably detected using probes that are capable of hybridizing to a oligonucleotide region present within the oligonucleotide that is amplified by the above-described SARS-CoV-2- and mutant of SARS-Cov-2 specific primers (see Tables 1 to 10). Such detection can be accomplished using any suitable method, e.g., molecular beacon probes, scorpion primer-probes, TaqMan probes, etc. (Navarro, E. et al. (2015) "Real-Time PCR Detection Chemistry," Clin. Chim. Acta 439:231-250). All of these methods employ an oligonucleotide that is labeled with a fluorophore and complexed to a quencher of the fluorescence of that fluorophore.

A wide variety of fluorophores and quenchers are known and are commercially available (e.g., Biosearch Technologies, Gene Link), and may be used in accordance with the methods of the present invention. Preferred fluorophores include the fluorophores Biosearch Blue, Alexa488, FAM, Oregon Green, Rhodamine Green-X, NBD-X, TET, Alexa430, BODIPY R6G-X, CAL Fluor Gold 540, JOE, Yakima Yellow, Alexa 532, VIC, HEX, and CAL Fluor Orange 560 (which have an excitation wavelength in the range of about 352-538 nm and an emission wavelength in the range of about 447-559 nm, and whose fluorescence can be quenched with the quencher BHQ1), or the fluorophores RBG, Alexa555, BODIPY 564/570, BODIPY TMR-X, Quasar 570, Cy3, Alexa 546, NED, TAMRA, Rhodamine Red-X, BODIPY 581/591, Redmond Red, CAL Fluor Red 590, Cy3.5, ROX, Alexa 568, CAL Fluor Red 610, BODIPY TR-X, Texas Red, CAL Fluor Red 635, Pulsar 650, Cy5, Quasar 670, CY5.5, Alexa 594, BODIPY 630/650-X, or Quasar 705 (which have an excitation wavelength in the range of about 524-690 nm and an emission wavelength in the range of about 557-705 nm, and whose fluorescence can be quenched with the quencher BHQ2). The preferred SARS-CoV-2-specific TaqMan probes of the present invention are labeled with either the fluorophore 2',7'-dimethoxy-4',5'-dichloro-6-carboxyfluorescein ("JOE") or the fluorophore 5(6)-carboxyfluorescein ("FAM") on their 5' termini. JOE is a xanthene fluorophore with an emission in yellow range (absorption wavelength of 520 nm; emission wavelength of 548 nm). FAM is a carboxyfluorescein molecule with an absorption wavelength of 495 nm and an emission wavelength of 517 nm; it is typically provided as a mixture of two isomers (5-FAM and 6-FAM). Quasar 670 is similar to cyanine dyes, and has an absorption wavelength of 647 nm and an emission wavelength of 670 nm.

The black hole quencher 1 ("BHQ1") is a preferred quencher for FAM and JOE fluorophores. BHQ1 quenches fluorescent signals of 480-580 nm and has an absorption maximum at 534 nm.

The black hole quencher 2 ("BHQ2") is a preferred quencher for Quasar 670. BHQ2 quenches fluorescent signals of 560-670 nm and has an absorption maximum at 579 nm.

JOE, FAM, Quasar 670, BHQ1 and BHQ2 are widely available commercially (e.g., Sigma Aldrich; Biosearch Technologies, etc.) and are coupled to oligonucleotides using methods that are well known (see, e.g., Zearfoss, N. R. et al. (2012) "End-Labeling Oligonucleotides with Chemical Tags After Synthesis," Meth. Mol. Biol. 941:181-193). Oligonucleotide probes of any desired sequence labeled may be obtained commercially (e.g., ThermoFisher Scientific) already labeled with a desired fluorophore and complexed with a desired quencher.

As discussed above, the proximity of the quencher of a TaqMan probe to the fluorophore of the probe results in a quenching of the fluorescent signal. Incubation of the probe in the presence of a double-strand-dependent 5'→3' exonuclease (such as the 5"→3" exonuclease activity of Taq polymerase) cleaves the probe when it has hybridized to a complementary target sequence, thus separating the fluorophore from the quencher and permitting the production of a detectable fluorescent signal.

The chemistry and design of "TaqMan" probes is reviewed by Holland, P. M. et al. (1991) ("Detection Of Specific Polymerase Chain Reaction Product By Utilizing The 5'→3' Exonuclease Activity Of *Thermus aquaticus* DNA Polymerase," Proc. Natl. Acad. Sci. (U.S.A.) 88(16): 7276-7280), by Navarro, E. et al. (2015) ("Real-Time PCR Detection Chemistry," Clin. Chim. Acta 439:231-250), and by Gasparic, B. M. et al. (2010) ("Comparison Of Nine Different Real-Time PCR Chemistries For Qualitative And Quantitative Applications In GMO Detection," Anal. Bioanal. Chem. 396(6):2023-2029).

Molecular beacon probes can alternatively be employed to detect amplified SARS-CoV-2 oligonucleotides in accordance with the present invention. Molecular beacon probes are also labeled with a fluorophore and complexed to a quencher. However, in such probes, the quenching of the fluorescence of the fluorophore only occurs when the quencher is directly adjacent to the fluorophore. Molecular beacon probes are thus designed to adopt a hairpin structure while free in solution (thus bringing the fluorescent dye and quencher into close proximity with one another). When a molecular beacon probe hybridizes to a target, the fluorophore is separated from the quencher, and the fluorescence of the fluorophore becomes detectable. Unlike TaqMan probes, molecular beacon probes are designed to remain intact during the amplification reaction, and must rebind to target in every cycle for signal measurement. The chemistry and design of molecular beacon probes is reviewed by Han, S. X. et al. (2013) ("Molecular Beacons: A Novel Optical Diagnostic Tool," Arch. Immunol. Ther. Exp. (Warsz). 61(2):139-148), by Navarro, E. et al. (2015) ("Real-Time PCR Detection Chemistry," Clin. Chim. Acta 439:231-250), by Goel, G. et al. (2005) ("Molecular Beacon: A Multitask Probe," J. Appl. Microbiol. 99(3):435-442) and by Zheng, J. et al. (2015) ("Rationally Designed Molecular Beacons For Bioanalytical And Biomedical Applications," Chem. Soc. Rev. 44(10):3036-3055).

Scorpion primer-probes (Whitcombe, D. et al. (1999) "Detection Of PCR Products Using Self-Probing Amplicons And Fluorescence," Nat. Biotechnol. 17(8):804-807) can alternatively be employed to detect amplified SARS-CoV-2 or SARS-CoV-2 mutant oligonucleotides in accordance with the present invention. Scorpion primer-probes are also designed to adopt a hairpin structure while free in solution, and are also labeled with a fluorophore at their 5' terminus and complexed to a quencher at their 3' terminus. Scorpion primer-probes differ from molecular beacon probes in that their 3'-end is attached to their 5'-end by a hexathylene glycol (HEG) blocker. Such attachment prevents the polymerase-mediated extension of the 3' terminus of the scorpion primer-probe. However, after the scorpion primer-probe has bound to its target DNA, the polymerase copies the sequence of nucleotides from its 3'-end. In the next denaturation step, the specific sequence of the scorpion primer-probe binds to the complementary region within the same strand of newly amplified DNA. This hybridization opens the hairpin structure and, as a result, separates the molecules fluorophore from its quencher and permits fluorescence to be detected.

In a preferred embodiment, the probes of the present invention are TaqMan probes. As described above, such probes are labeled on their 5' termini with a fluorophore, and are complexed on their 3' termini with a quencher of the fluorescence of that fluorophore. In order to simultaneously detect the amplification of two polynucleotide portions of SARS-CoV-2, two TaqMan probes (wildtype probe and mutant probe) are employed that have different fluorophores (with differing and distinguishable emission wavelengths); the employed quenchers may be the same or different. It has surprisingly been found that in each system the detection of mutants is highly specific. Thus, a discrimination between the wildtype and the specific mutant in each system (see Tables 1 to 10) can be achieved.

In one embodiment of the invention, the 5' terminus of the Mutant Probe is labeled with the fluorophore HEX, and the 3' terminus of such probe is complexed to the quencher BHQ1 and the 5' terminus of the Wildtype Probe is labeled with the fluorophore FAM, and the 3' terminus of such probe is complexed to the quencher BHQ1. In an alternative embodiment, the 5' terminus of the Mutant Probe is labeled with the fluorophore FAM, and the 5' terminus of the Wildtype Probe is labeled with the fluorophore HEX. The use of such two fluorophores permits both probes to be used in the same assay.

The preferred primers and probes described in Table 1 to 10 were designed for the specific detection of SARS-CoV-2 and the respective specific mutant. Each target on its own has been shown to provide sensitive and specific detection of SARS-CoV-2 or the respective mutant with no detection of, or cross-reactivity to, other coronaviruses. The invention includes oligonucleotides whose nucleotide sequences consist of, consist essentially of, or are "variants" of such preferred primers and probes. As used herein, an oligonucleotide is a "variant" of another oligonucleotide if it retains the function of such oligonucleotide (e.g., acting as a specific primer or probe), but:

(1) lacks 1, 2, 3, 4, 5, 6, 7, 8, 9, or 10 nucleotides of the nucleotides of such primer or probe, or
(2) lacks 1, 2, 3, 4, 5, 6, 7, 8, 9, or 10 of the 10 3' terminal nucleotides of such primer or probe, or
(3) lacks 1, 2, 3, 4, 5, 6, 7, 8, 9, or 10 of the 10 5' terminal nucleotides of such primer or probe, or
(4) has a sequence that differs from that of such primer or probe in having 1, 2, 3, 4, 5, 6, 7, 8, 9, 10 or more than 10 additional nucleotides, or
(5) has a sequence that differs from that of such primer or probe in having 1, 2, 3, 4, 5, 6, 7, 8, 9, 10 or more than 10 substitution nucleotides in lieu of the nucleotides present in such primer or probe, or
(6) possesses a combination of such (1)-(5).

B. Preferred SARS-CoV-2 and Mutant of SARS-CoV-2-Specific Primers

1. Preferred Primers

The set of primers of each system reflected in tables 1 to 10 comprise a "Forward Primer" and a "Reverse Primer," whose sequences are suitable for amplifying a region of the SARS-CoV-2 spike gene. Although any Forward and Reverse Primers capable of mediating such amplification may be employed in accordance with the present invention, it is preferred to employ Forward and Reverse Primers that possess distinctive advantages and which are reflected in Tables 1 to 10. The preferred Forward Primer of the present invention comprises, consists essentially of, or consists of, the sequences reflected in Table 1 to 10.

Accordingly, these primers can amplify a double-stranded polynucleotide having the sequence of nucleotides the S Gene of SARS-CoV-2. Such preferred "Forward Primer" and preferred "Reverse Primer" have distinctive attributes for use in the detection of SARS-CoV-2.

While it is preferred to detect the presence of the S Gene using primers that consist of the sequences mentioned in Table 1 to 10, the invention contemplates that other primers that consist essentially of the primer sequences as mentioned in Tables 1 to 10 (in that they possess 1, 2, 3, 4, 5, 6, 7, 8, 9, or 10 additional nucleotide residues, but retain the ability to specifically hybridize to DNA molecules comprising the target nucleotide sequence mentioned in Table 1 to 10, and more preferably retain the ability to specifically hybridize to DNA molecules having the nucleotide sequence of complement of the nucleotide sequence or the nucleotide sequence of complement of the nucleotide sequence of or "variants" of such primers that retain the ability to specifically hybridize to DNA molecules having the nucleotide sequence mentioned in Tables 1 to 10.

Such "Variant Primers" may, for example:

(1) lack 1, 2, 3, 4 or 5 nucleotides of forward primer or reverse primer, or
(2) lack 1, 2, 3, 4 or 5 of the 10 3' terminal nucleotides of the sequence of forward primer or reverse primer, or
(3) lack 1, 2, 3, 4, 5, 6, 7, 8, 9, or 10 of the 10 5' terminal nucleotides of the forward primer or reverse, or
(4) have a sequence that differs from that of the explicitly mentioned primers in Table 1 to 10 in having 1, 2, 3, 4, 5, 6, 7, 8, 9, 10 or more than 10 additional nucleotides, or
(5) have a sequence that differs from that of the explicitly mentioned primers in Table 1 to 10 in that 1, 2, 3, 4, 5, 6, 7, 8, 9, 10 or more than 10 substitution nucleotides in lieu of the nucleotides present in SEQ ID NO:1 or of SEQ ID NO:2, or
(6) combinations of such (1)-(5).

One embodiment of the present invention is the forward primer (A) and/or reverse primer (A) as reflected in Table 1 for use in a PCR method to detect the genetic variation A23063T of SARS-CoV-2, preferably together with mutant probe (A) and/or wildtype probe (A).

One embodiment of the present invention is the forward primer (B) and/or reverse primer (B) as reflected in Table 2 for use in a PCR method to detect the genetic variation del21765-770 of SARS-CoV-2, preferably together with mutant probe (B) and/or wildtype probe (B).

One embodiment of the present invention is the forward primer (C) and/or reverse primer (C) as reflected in Table 3 for use in a PCR method to detect the genetic variation A23403G of SARS-CoV-2, preferably together with mutant probe (C) and/or wildtype probe (C).

One embodiment of the present invention is the forward primer (D) and/or reverse primer (D) as reflected in Table 4 for use in a PCR method to detect the genetic variation G22813T of SARS-CoV-2, preferably together with mutant probe (D) and/or wildtype probe (D).

One embodiment of the present invention is the forward primer (E) and/or reverse primer (E) as reflected in Table 5 for use in a PCR method to detect the genetic variation C23604A of SARS-CoV-2, preferably together with mutant probe (E) and/or wildtype probe (E).

One embodiment of the present invention is the forward primer (F) and/or reverse primer (F) as reflected in Table 6 for use in a PCR method to detect the genetic variation C22227T of SARS-CoV-2, preferably together with mutant probe (F) and/or wildtype probe (F).

One embodiment of the present invention is the forward primer (G) and/or reverse primer (G) as reflected in Table 7 for use in a PCR method to detect the genetic variation G22992A of SARS-CoV-2, preferably together with mutant probe (G) and/or wildtype probe (G).

One embodiment of the present invention is the forward primer (H) and/or reverse primer (H) as reflected in Table 8 for use in a PCR method to detect the genetic variation G25088T of SARS-CoV-2, preferably together with mutant probe (H) and/or wildtype probe (H).

One embodiment of the present invention is the forward primer (I) and/or reverse primer (I) as reflected in Table 9 for use in a PCR method to detect the genetic variation C22879A of SARS-CoV-2, preferably together with mutant probe (I) and/or wildtype probe (I).

One embodiment of the present invention is the forward primer (J) and/or reverse primer (J) as reflected in Table 10 for use in a PCR method to detect the genetic variation G23012A of SARS-CoV-2, preferably together with mutant probe (J) and/or wildtype probe (J).

C. Preferred SARS-CoV-2-Specific Probes and SARS-CoV-2 Mutant Probes

1. Preferred Probe

The preferred probe for detecting the region of S-Gene and mutations thereof that is amplified by the above-described preferred Primers are shown in Tables 1 to 10.

D. Distinctive Attributes of the Preferred Primers and Probes of the Present Invention The assays of the present invention possess particular distinctive attributes that distinguish such assays from the assays of the prior art. One characteristic of the present invention relates to the use of one SARS-CoV-2 target region in which a specific genetic variation occurs as a basis for the detection in an rRT-PCR assay. Thus, the rRT-PCR assays of the present invention preferably employ only one pair of Forward and Reverse primers but two probes, namely the wildtype probe and respective mutant probe so as to be capable of specifically amplifying one polynucleotide region of SARS-CoV-2 RNA either the wildtype or the mutant.

The assays of the present invention employ probes that are unique to SARS-CoV-2 and mutants of SARS-CoV-2 and detect SARS-CoV-2 mutants and wildtype under conditions in which non-SARS-CoV-2 pathogens are not detected. In a further attribute, the assays of the present invention employ very fast system primers that are designed to mediate the same degree of amplification under the same reaction parameters and temperatures.

The melting temperatures (Tm) of PCR primers determine their kinetics of denaturation from complementary oligonucleotides and their kinetics of annealing to complementary oligonucleotides (see, SantaLucia, J. (1998) A Unified View Of Polymer, Dumbbell, And Oligonucleotide DNA Nearest-Neighbor Thermodynamics," Proc. Natl. Acad. Sci. (U.S.A.) 95:1460-1465; von Ahsen, N. et al. (1999) "Application Of A Thermodynamic Nearest-Neighbor Model To Estimate Nucleic Acid Stability And Optimize Probe Design: Prediction Of Melting Points Of Multiple Mutations Of Apolipoprotein B-3500 And Factor V With A Hybridization Probe Genotyping Assay On The Lightcycler," Clin. Chem. 45(12):2094-2101).

Primer pairs that exhibit "substantially identical melting temperatures" (i.e., 2° C., more preferably, ±1° C., still more preferably ±0.5° C., and most preferably ±0.1° C., as calculated using the method of SantaLucia, J. (1998)) maximize the overall yield of the products that they amplify, and the rate at which such products are produced. Significantly, the preferred Forward and Reverse Primers of the present invention exhibit such substantially identical melting temperatures, which is a further distinction of the present invention.

The preferred Forward and Reverse S Gene Primers of the present invention also exhibit substantially identical melting temperatures, which is a further distinction of the present invention.

In designing an rRT-PCR assay, it is desirable for the employed TaqMan probe to have a Tm that is 5-10° C. higher than the employed amplification primers. The employed Probes have a difference from the Tm of the preferred Primers of the present invention. Thus, each of the preferred TaqMan probes of the present invention exhibit a desired Tm and the two preferred TaqMan probes (wildtype and mutant) of the present invention exhibit preferably substantially different Tms. These are further distinctions of the present invention.

E. Preferred Platform for Conducting the Assays of the Present Invention

In a preferred embodiment, the above-described preferred primers and probes assay the presence of SARS-CoV-2 using a Direct Amplification Disc (DiaSorin Molecular LLC) and SIMPLEXA® Direct Chemistry (DiaSorin Molecular LLC), as processed by a LIAISON® MDX (DiaSorin Molecular LLC) rRt-PCR platform. The operating principles of DiaSorin Molecular LLC's LIAISON® MDX rRt-PCR platform, SIMPLEXA® Direct Chemistry and Direct Amplification Disc are disclosed in U.S. Pat. No. 9,067,205, US Patent Publn. No. 2012/0291565 A1, EP 2499498 B1, EP 2709760 B1, all herein incorporated by reference in their entireties.

In brief, the LIAISON® MDX (DiaSorin) rRt-PCR platform is a compact and portable thermocycler that additionally provides centrifugation and reaction processing capabilities. The device is capable of mediating sample heating (>5° C./sec) and cooling (>4° C./sec), and of regulating temperature to ±0.5° C. (in the range from room temperature to 99° C.). The LIAISON® MDX rRt-PCR platform has the ability to excite fluorescent labels at 475 nm, 475 nm, 520 nm, 580 nm, and 640 nm, and to measure fluorescence at 520 nm, 560 nm, 610 nm and 682 nm, respectively.

The Direct Amplification Disc is radially oriented, multi-chambered, fluidic device that is capable of processing the amplification of target sequences (if present) in up to 8 (50 µL) clinical samples at a time. The samples may be provided directly to the Direct Amplification Disc, as cellular material or lysates, without any prior DNA or RNA extraction.

F. Kits

The invention additionally includes kits for conducting the above-described assays. In one embodiment, such kits will include one or more containers containing reagents for specifically detecting the SARS-CoV-2 wildtype and SARS-CoV-2 mutants.

Typically, a kit of the invention comprises at least two separate container, said container being a a) container for an enzyme mix, preferably comprising a reverse transcriptase enzyme, a polymerase such as Taq polymerase; and optionally HotStart antibodies; and
b) a container comprising primers and probes; and
c) optionally a container for buffer and/or target positive control oligonucleotides.

Typical positive controls are wildtype target sequence and/or mutant target sequence. The respective target sequences are reflected in Tables 1 to 10.

G. Examples

The Examples have been conducted with the following general setup as reflected in Table B:

TABLE B

| Component | Concentrations | Supplier |
|---|---|---|
| Enzyme Mix[1] | 0.15 U/µl Units MMLV Reverse Transcriptase | New England Biolabs |
| | 0.05 Units/µl Taq Polymerase | New England Biolabs |
| | 4 ng/µl HotStart Antibody | Takara |
| PCR Buffer[2] | 10 mM Tris-HCl | Merck/Sigma Aldrich |
| | 50 mM KCl | Merck/Sigma Aldrich |
| | 2 mM MgCl2 | Merck/Sigma Aldrich |
| | 0.2 mM dATP | Merck/Sigma Aldrich |
| | 0.2 mM dTTP | Merck/Sigma Aldrich |
| | 0.2 mM dCTP | Merck/Sigma Aldrich |
| | 0.2 mM dGTP | Merck/Sigma Aldrich |
| Assay Mix[3] | 0.6 µM Forward Primer | Microsynth |
| | 0.6 µM Reverse Primer | Microsynth |
| | 0.12 µM Wildtype Probe | Microsynth |
| | 0.12 µM Mutant Probe | Microsynth |

[1]Enzyme Mix additionally comprises a Storage Buffer
[2]PCR Buffer is one component of MTS Buffer which additionally comprises ROX dye for optional normalization
[3]solved in 10 mM Tris pH 7.4

The forward primer, reverse primer, wildtype probe and mutant probe oligonucleotides are reflected in Tables 1 to 10.

In the Examples, 20 µL of qPCR reaction mixture were prepared for each qPCR sample. To avoid pipetting errors, a mastermix comprising MTS Buffer, Enzyme Mix, Assay Mix and $H_2O$ was prepared which was placed in the wells of a Microamp 96well Fast PCR Plate, 0.1 ml vessel volume, before addition of the respective Sample. The composition of a qPCR reaction mixture (total volume 20 µL) was as shown below:

4 µl MTS Buffer (PCR Puffer, ROX dye for optional normalization)
1 µl Enzyme Mix
4 µl $H_2O$
1 µl Assay Mix
10 µl Sample The Sample was either SARS-CoV-2 UK Variant [N501Y] RNA, SARS-CoV-2 Wildtype RNA, or target positive controls (TPC) of SARS-CoV-2 UK Variant [N501Y] or SARS-CoV-2 Wildtype. The SARS-CoV-2 UK Variant [N501Y] RNA and SARS-CoV-2 Wildtype RNA was isolated from patients tested positive on SARS-CoV-2 and were made available by the "Rijksinstituut voor Volksgezondheid en Milieu", Netherlands. The TPCs are DNA plasmids comprising the corresponding DNA sequences of SARS-CoV-2 UK Variant [N501Y] RNA and SARS-CoV-2 Wildtype RNA.

Each qPCR reaction (20 µl reaction volume as described previously) was carried out with the following PCR setup:

Microamp 96well Fast PCR Plates, 0.1 ml vessel volume, were used. As qPCR cycler, the 7500 FAST qPCR Cycler of Applied Biosystems was used. 4 replicates per sample were prepared and investigated.

The qPCR program used in the Examples is shown in Table C:

TABLE C qPCR program used in the Examples.

| STEP | CYCLES | TEMPERATURE | DURATION |
|---|---|---|---|
| Pre-PCR Read[1] | 1 | 50° C. | 1 minute |
| Reverse Transcription | 1 | 50° C. | 5 minutes |
| Initial Denaturation | 1 | 95° C. | 5 minutes |
| Amplification | 45 | 95° C. | 5 seconds |
| | | 57° C.[2] | 45 seconds |
| Post-PCR Read[1] | 1 | 50° C. | 1 minute |

[1]The genotyping/ allelic discrimination option of the qPCR device with pre- and post-PCR reads at 50° C. was used.
[2]Data Collection was enabled for FAM™ (wildtype), HEX/VIC (N501Y mutant) and ROX for passive reference (results not shown).

Example 1—Determination of SARS-CoV-2 Wildtype Detection Limit

To determine the limit of detection of the qPCR method for SARS-CoV-2 Wildtype, the following serial dilution of SARS-CoV-2 Wildtype RNA was prepared (Table D):

TABLE D

| Sample | Copy Number of SARS-CoV-2 Wildtype RNA in the samples | Copy Number per 20 µl PCR reaction |
|---|---|---|
| 1 | 200,000 | 2,000,000 |
| 2 | 40,000 | 400,000 |
| 3 | 8,000 | 80,000 |
| 4 | 1,600 | 16,000 |
| 5 | 320 | 3,200 |
| 6 | 64 | 640 |
| 7 | 12.8 | 128 |
| 8 | 2.5 | 25 |
| 9 | 0.5 | 5 |
| 10 | 0.1 | 1 |
| 11 | 0.02 | 0.2 |
| 12 | H2O | H2O |

The qPCR reaction mixtures were prepared and the qPCR reactions were carried out as described previously. The results of the qPCR reaction are shown in FIG. 1.

Example 2—Determination of SARS-CoV-2 UK Variant [N501Y] Detection Limit

To determine the limit of detection of the qPCR method for SARS-CoV-2 UK variant [N501Y], the following serial dilution of SARS-CoV-2 UK variant [N501Y] RNA was prepared (Table E):

TABLE E

| Sample | Copy Number of SARS-CoV-2 UK variant [N501Y] RNA in the samples | Copy Number per 20 µl PCR reaction |
|---|---|---|
| 1 | 10,000 | 100,000 |
| 2 | 3,300 | 33,000 |
| 3 | 1,100 | 11,000 |
| 4 | 370 | 3,700 |
| 5 | 123.4 | 1,234 |
| 6 | 41.1 | 411 |
| 7 | 13.7 | 137 |
| 8 | 4.5 | 45 |
| 9 | 1.5 | 15 |
| 10 | 0.6 | 6 |
| 11 | 0.17 | 1.7 |
| 12 | $H_2O$ | $H_2O$ |

Figure 2:
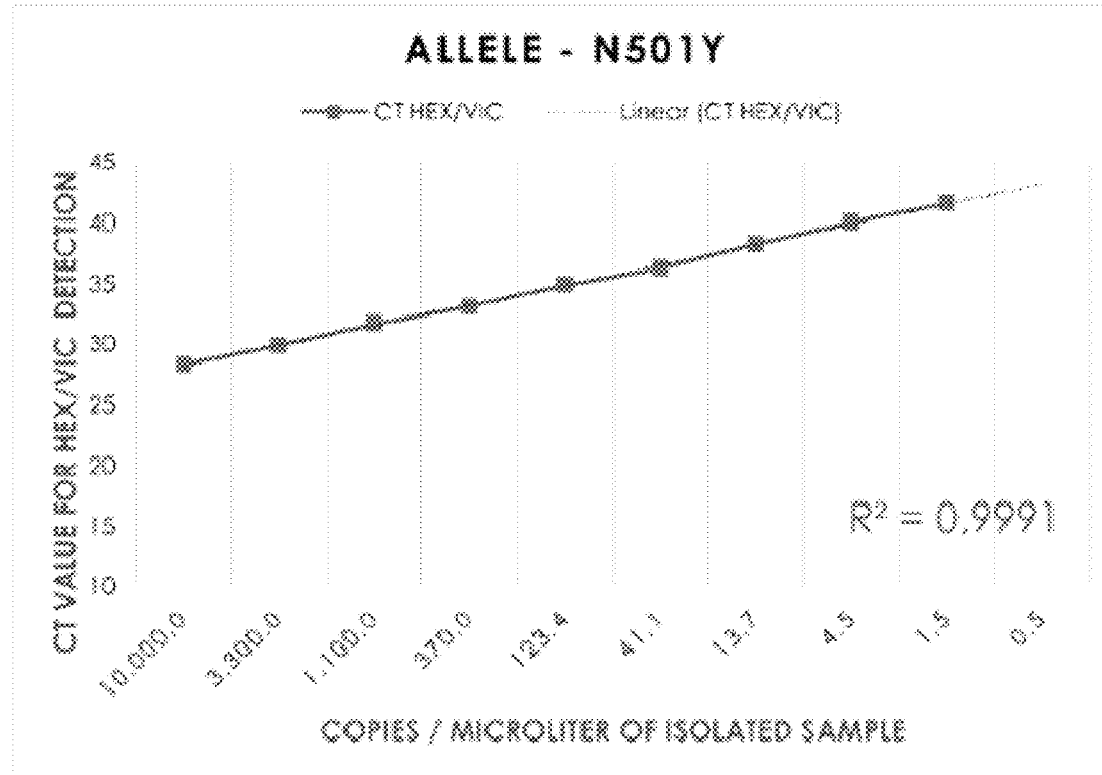
FIG. 2 shows the limits of detection of the qPCR method for SARS-CoV-2 UK variant [N501Y].

The qPCR reaction mixtures were prepared and the qPCR reactions were carried out as described previously. The results of the qPCR reaction are shown in FIG. 2.

TABLE F

Clinical validation of Wildtype SARS-CoV-2

| | | Screen for mutant N501Y | |
|---|---|---|---|
| Reference Method | n | positive | negative |
| Positive | 93 | A = 92 | B = 1 |
| Negative | 76 | C = 0 | D = 76 |
| Clinical sensitivity = [a/(a + c)] × 100 = [92/(92 + 0)] × 100 = | | | 100% |
| Clinical specificity = [d/(b + d)] × 100 = [76/(1 + 76] × 100 = | | | 98.70% |

TABLE G

Clinical validation of Mutant N501Y of SARS-CoV-2

| | | Mutant Screen N501Y | |
|---|---|---|---|
| Reference Method | n | positive | negative |
| Positive[3] | 15 | A = 15 | B = 0 |
| Negative | 74 | C = 0 | D = 74 |
| Clinical sensitivity = [a/(a + c)] × 100 = [15/(15 + 0)] × 100 = | | | 100% |
| Clinical specificity = [d/(b + d)] × 100 = [74/(0 + 74] × 100 = | | | 100% |

Example 3—Determination of the Specificity of the Mutant Probe (A) and the Wildtype Probe (A) Reflected in Table 1

To determine the specificity of the mutant probe (A) and the wildtype probe (A) reflected in Table 1, qPCR reactions were performed using as a Sample either the SARS-CoV-2 UK Variant [N501Y] RNA or SARS-CoV-2 Wildtype RNA described previously, the Enzyme Mix and the MTS Buffer as previously described and the Assay Mix comprising Forward Primer (A) of SEQ ID NO: 3, Reverse Primer (A) of SEQ ID NO: 4, the mutant probe (A) of SEQ ID NO: 6, and the wildtype probe (A) of SEQ ID NO: 5. 20 µL qPCR reaction samples were prepared as described previously. The copy number of the Sample in the qPCR sample was as reflected.

As a negative control, qPCR samples comprising 10 µL water instead of the Sample were prepared. The qPCR program described in Table C was used.

Figure 3:
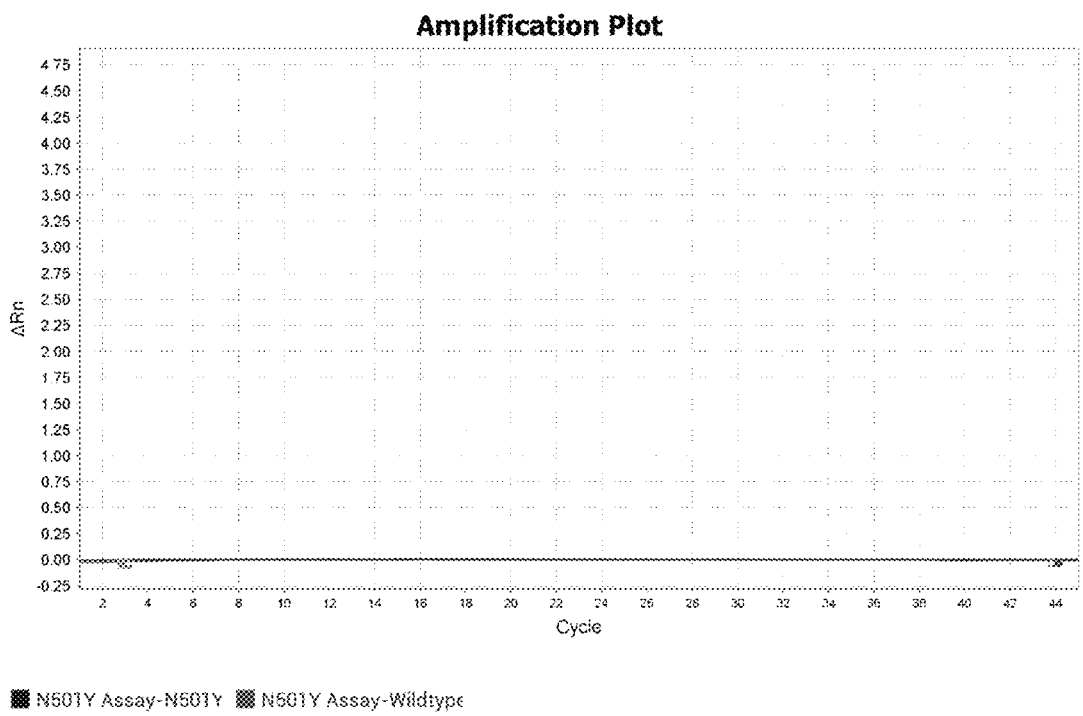
FIG. 3 shows the amplification plot of the negative water control.
Figure 4:
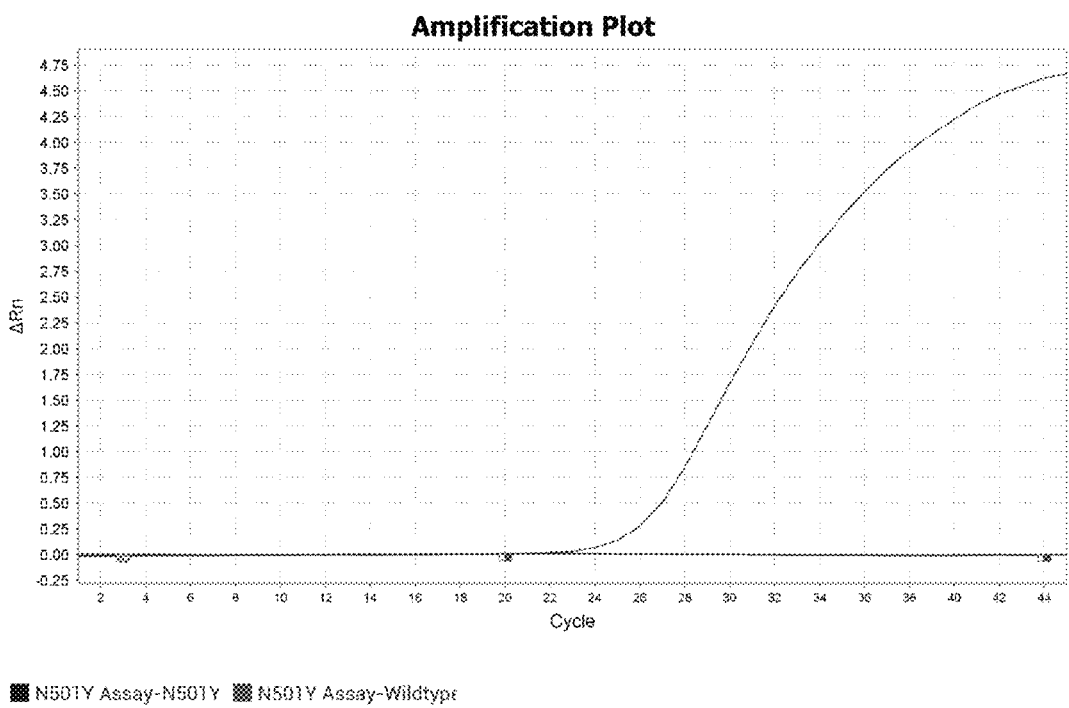
FIG. 4 shows the amplification plot of a sample containing SARS-CoV-2 Wildtype RNA.
Figure 5:
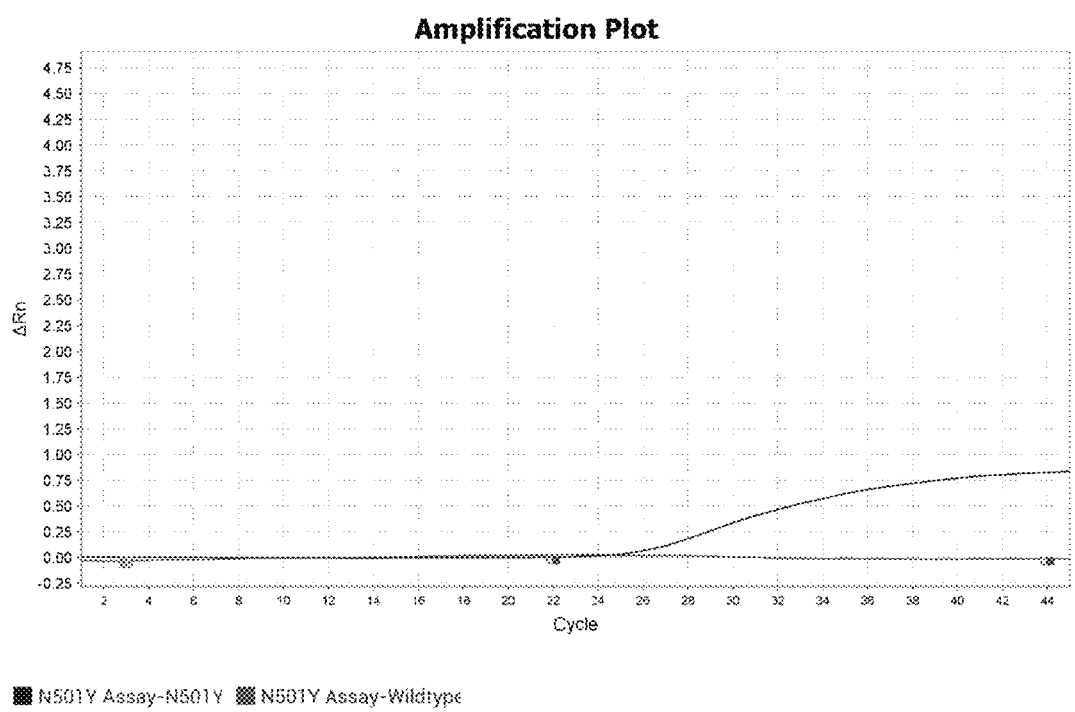
FIG. 5 shows the amplification plot of a sample containing SARS-CoV-2 UK Variant [N501Y] RNA.

The amplification plots showing the results of the qPCR reactions are shown in FIGS. 3, 4, and 5. FIG. 3 shows the amplification plot of the negative water control. As can be seen, neither in the FAM-channel (wildtype probe (A) channel) nor in the HEX-channel (mutant probe (A) channel) a fluorescence signal can be detected.

FIG. 4 shows the amplification plot of a sample containing SARS-CoV-2 Wildtype RNA. Here, in the FAM-channel (wildtype probe (A) channel) a fluorescence signal can be detected. Surprisingly, no signal can be detected in the HEX-channel (mutant probe (A) channel). The specificity of the wildtype probe (A) to the SARS-CoV-2 Wildtype RNA is really high, while the mutant probe (A) does not bind to the Wildtype RNA at all.

FIG. 5 shows the amplification plot of a sample containing SARS-CoV-2 UK Variant [N501Y] RNA. Here, in the HEX-channel (mutant probe (A) channel) a fluorescence signal can be detected. Surprisingly, no signal can be detected in the FAM-channel (wildtype probe (A) channel). The specificity of the mutant probe (A) to the SARS-CoV-2 UK Variant [N501Y] RNA is very high, while the wildtype probe (A) does not bind to the SARS-CoV-2 UK Variant [N501Y] RNA at all.

Figure 6:
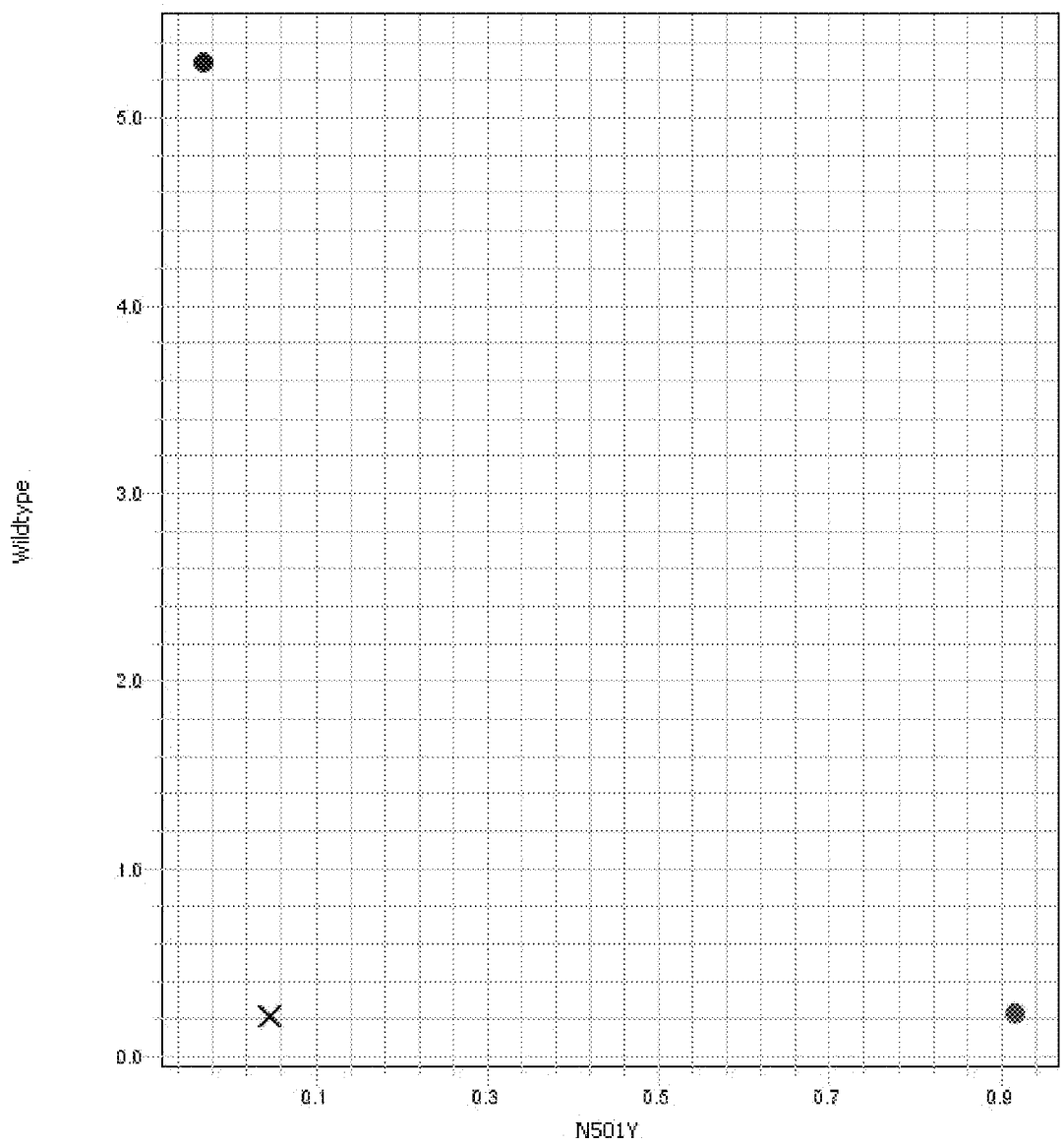
FIG. 6 describes the result of the allelic discrimination plot.

FIG. 6 describes the result of the allelic discrimination plot.

Comparison Study—Specificity of the Probes of the Invention Compared to Other Probes

TABLE H

Mutant Probe (A) of the invention "0" and comparative probes "-4", "-2", "+2" and "+4"

| Name of probe | Sequence (Sequence 5'-3' Modification 5'-FAM & 3'-BHQ-1) | Seq ID NO | Note |
|---|---|---|---|
| -4 | TCC AAC CCA CTT AT | 73 | 1) |
| -2 | TCC AAC CCA CTT ATG G | 74 | 2) |
| 0 | TCC AAC CCA CTT ATG GTG | 6 | 3) |
| +2 | TCC AAC CCA CTT ATG GTG TT | 75 | 4) |
| +4 | TCC AAC CCA CTT ATG GTG TTG G | 76 | 5) |

Note
1) 4 bp shortened on 3' end
2) 2 bp shortened on 3' end
3) Mutant probe (A) of the invention
4) 2 bp lengthened on 3' end
5) 4 bp lengthened on 3' end To determine the specificity of the mutant probe (A) and the wildtype probe (A) reflected in Table 1, qPCR reactions were performed using as a Sample either the SARS-CoV-2 UK Variant [N501Y] RNA (B.1.1.7 RNA) or SARS-CoV-2 Wildtype RNA described previously, the Enzyme Mix and the MTS Buffer as previously described and the Assay Mix comprising Forward Primer (A) of SEQ ID NO: 3, Reverse Primer (A) of SEQ ID NO: 4, the mutant probe (A) of SEQ ID NO: 6, and the wildtype probe (A) of SEQ ID NO: 5. 20 µL qPCR reaction samples were prepared as described previously.

Figure 7:
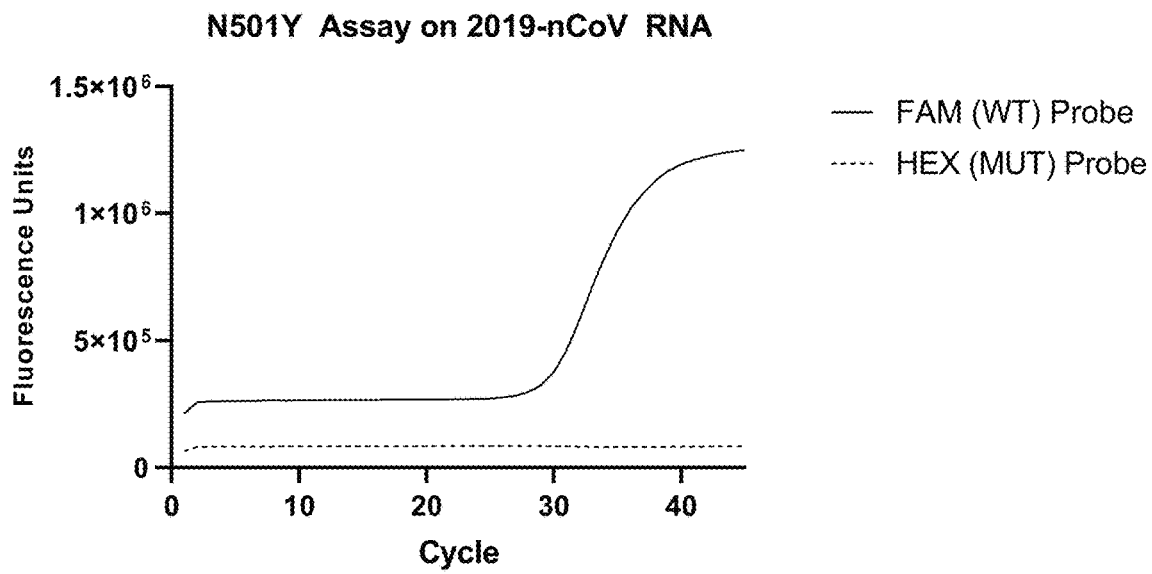
FIG. 7 shows high selectivity for wildtype probes of the invention (FAM (WT) Probe) on a SARS-CoV-2 wildtype sample.
Figure 10:
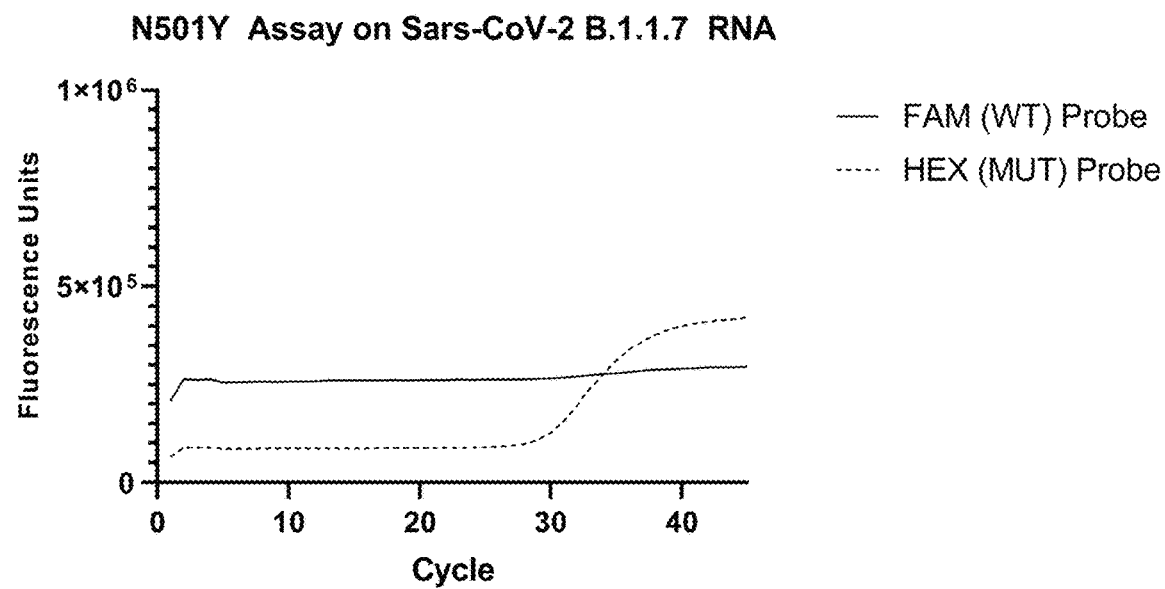
FIG. 10 shows high specificity for a mutant probe of the invention compared to a wildtype probe of the invention on SARS-CoV-2 mutant sample (B.1.1.7)

FIGS. 7 and 10 show the high specificity of the wildtype probe (A) and mutant probe (A). "FAM(WT) Probe" means wildtype probe (A) labeled with FAM and "HEX (MUT) Probe" means mutant probe (A) labeled with HEX.

With the same set up probes "−4", "−2", "+2" and "+4" have been tested and compared to mutant probe (A) of the invention.

Figure 8:
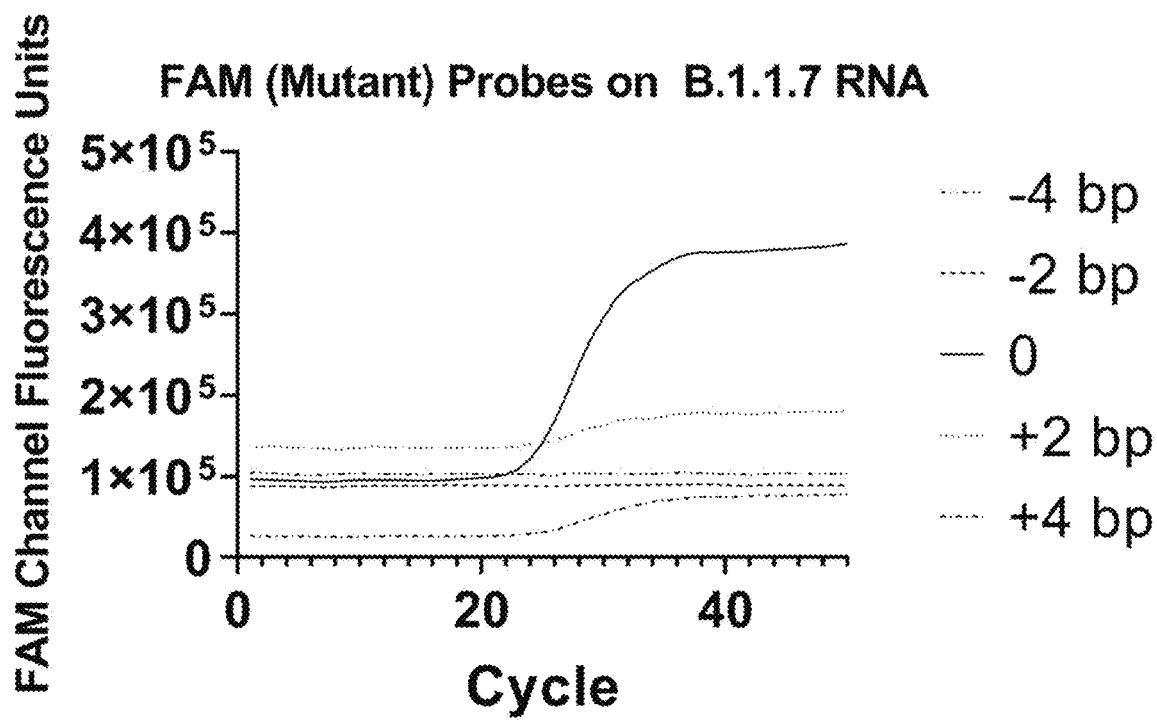
FIG. 8 shows high selectivity for mutant probes ("0") of the invention for a mutant SARS-CoV-2 sample compared to modified mutant probes.

FIG. 8 shows that the mutant probe (A) of the invention which is labeled with FAM (FAM (Mutant) Probe "0") is highly specific for the UK variant B.1.1.7 (genetic variation A23063T) compared to modified mutant probes "−4", "−2", "+2" and "+4".

Figure 9:
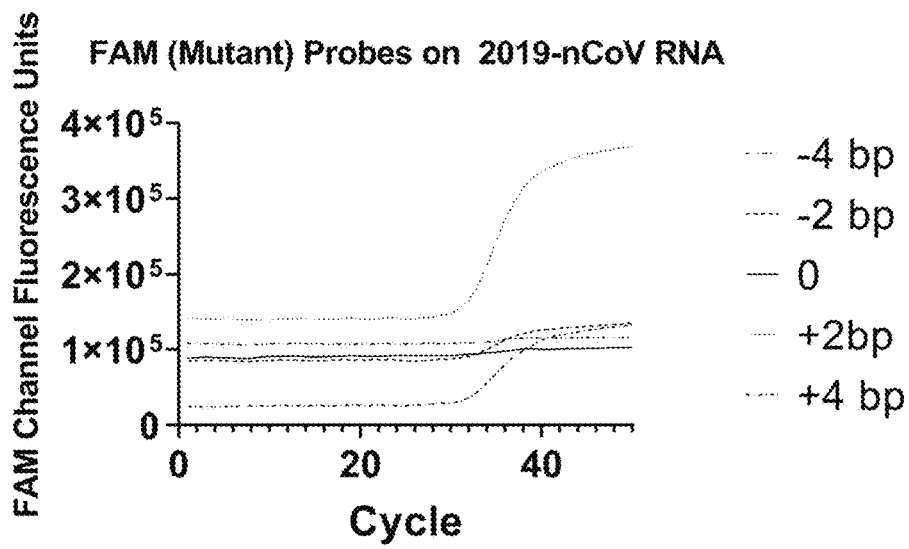
FIG. 9 shows that the mutant probes of the inventions do not significantly provide signals for wildtype SARS-CoV-2 samples.

FIG. 9 shows that mutant probe (A) of the invention which is labeled with FAM (FAM (Mutant) Probe "0") is almost not binding compared to modified mutant probes "−4", "−2" "+2" and "+4".

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

The invention claimed is:

1. An oligonucleotide, having a 5' terminus and a 3' terminus, wherein said oligonucleotide is detectably labeled and has a nucleotide sequence that consists of one of the nucleotide sequences selected from SEQ ID NO:6 and SEQ ID NO: 24,
wherein said oligonucleotide has a 5' terminus that is labeled with a fluorophore and a 3' terminus that is connected or complexed to a quencher of fluorescence of said fluorophore.

2. The oligonucleotide according to claim 1, wherein said oligonucleotide is a mutant probe of SARS-COV-2 said probe having a nucleotide sequence that consists of one of the nucleotide sequences selected from SEQ ID NO: 6 and SEQ ID NO:24; and wherein said oligonucleotide has a 5' terminus that is labeled with Hexachlorofluorescein (HEX) and a 3' terminus that is connected or complexed to a quencher.

3. A method for detecting the presence of a genetic variation (mutant) of SARS-COV-2 wildtype in a sample, wherein the genetic variation of the spike gene of SARS-COV-2 is selected from the group consisting of A23063T and/or G22813T and optionally G23012A, wherein said method comprises
1) contacting a sample with
   a) amplification primers specifically hybridizing to a target sequence selected from oligonucleotides comprising said genetic variation of the spike gene of SARS-COV-2 or a fragment thereof comprising said genetic variation;
   b) a mutant probe having a nucleotide sequence that consists of the nucleotide sequences SEQ ID NO:6 and/or SEQ ID NO: 24 and optionally SEQ ID NO: 60 said mutant probe being a detectably labeled oligonucleotide that is able to specifically hybridize to said genetic variation of the spike gene of SARS-COV-2 or a fragment thereof, wherein said mutant probe is preferably labeled with a fluorophore and a quencher of fluorescence of said fluorophore,
2) performing a primer extension reaction; and
3) determining whether said genetic variation of the spike gene of SARS-COV-2 or a fragment thereof is present in said sample, preferably-by determining whether a fluorescent signal of said fluorophore has become detectable.

4. Method according to claim 3 wherein the oligonucleotides of the target sequence comprising the genetic variation comprise or are consisting of one of SEQ ID NO:2 and SEQ ID NO: 20 and optionally SEQ ID NO: 56.

5. Method according to claim 3 wherein said method comprises
1) contacting a sample with
   a) amplification primers specifically hybridizing to a target sequence selected from the group consisting of one of SEQ ID NO:2 or SEQ ID NO: 20 or and optionally SEQ ID NO: 56;
   b) a mutant probe said mutant probe being a detectably labeled oligonucleotide that is able to specifically hybridize to the genetic variation of the spike gene of SARS-COV-2 or a fragment thereof, wherein said mutant probe is labeled with a fluorophore and a quencher of fluorescence of said fluorophore, and wherein the oligonucleotides of the mutant probe are selected from the group consisting of SEQ ID NO:6 and/or SEQ ID NO: 24 and optionally SEQ ID NO: 60;
2) performing a primer extension reaction; and
3) determining whether the genetic variation of the spike gene of SARS-COV-2 or a fragment thereof is present in said sample by determining whether a fluorescent signal of said fluorophore has become detectable, wherein
ii) presence of the target sequence SEQ ID NO:56 or presence of said sequence within the nucleotide sequences of the sample; and use of a mutant probe having an oligonucleotide consisting of SEQ ID NO:60 indicates the genetic variation G23012A; and
ii) presence of the target sequence SEQ ID NO:20 or presence of said sequence within the nucleotide sequences of the sample; and use of a mutant probe having an oligonucleotide consisting of SEQ ID NO:24 indicates the genetic variation G22813T; and
iii) presence of the target sequence SEQ ID NO:56 or presence of said sequence within the nucleotide sequences of the sample; and use of a mutant probe having an oligonucleotide consisting of SEQ ID NO:60 indicates the genetic variation G23012A.

6. Method according to claim 3 for detecting the presence of the genetic variation A23063T of the spike gene of SARS-COV-2 wildtype in a sample, wherein said method comprises
1) contacting a sample with
   a) Forward Primer (A) comprising or consisting of an oligonucleotide having SEQ ID NO: 3,
   b) Reverse Primer (A) comprising or consisting of an oligonucleotide having SEQ ID NO: 4; and
   c) a mutant probe (A) consisting of an oligonucleotide of SEQ ID NO:6 said mutant probe (A) being a detectably labeled oligonucleotide that is able to specifically hybridize to a target sequence (A) having a nucleotide sequence that comprises or consists essentially of SEQ ID NO:2; and wherein said mutant probe (A) oligonucleotide is labeled with a fluorophore and a quencher of fluorescence of said fluorophore;

2) performing a primer extension reaction; and
3) determining whether the genetic variation A23063T is present in said sample, by determining whether a fluorescent signal of said fluorophore has become detectable.

7. Method according to claim 3 for detecting the presence of the genetic variation G22813T of the spike gene of SARS-COV-2 wildtype in a sample, wherein said method comprises 1) contacting a sample with
   a) Forward Primer (D) comprising or consisting of an oligonucleotide having SEQ ID NO: 21,
   b) Reverse Primer (D) comprising or consisting of an oligonucleotide having SEQ ID NO: 22; and
   c) a mutant probe (D) consisting of an oligonucleotide of SEQ ID NO:24 said mutant probe (D) being a detectably labeled oligonucleotide that is able to specifically hybridize to a target sequence (D) having a nucleotide sequence that comprises or consists essentially of SEQ ID NO:20; and
   wherein said mutant probe (D) oligonucleotide is labeled with a fluorophore and a quencher of fluorescence of said fluorophore;

2) performing a primer extension reaction; and
3) determining whether the genetic variation G22813T is present in said sample, by determining whether a fluorescent signal of said fluorophore has become detectable.

8. A method for detecting the presence of a genetic variation (mutant) of SARS-COV-2 wildtype in a sample, wherein said method comprises:

(I) incubating said sample in vitro in the presence of:
(1) a reverse transcriptase and a DNA polymerase; and
(2) amplification primers comprising a Forward Primer and a Reverse Primer said amplification primers being suitable for specifically hybridizing to a target sequence selected from oligonucleotides comprising the genetic variation of the spike gene of SARS-COV-2 or a fragment thereof comprising said genetic variation; and
(3) a mutant probe, said mutant probe being an oligonucleotide that is able to specifically hybridize to a target sequence selected from the nucleotides comprising the genetic variation of the spike gene of SARS-COV-2 or a fragment thereof, wherein said mutant probe oligonucleotide is labeled with a fluorophore and a quencher of fluorescence of said fluorophore, wherein said incubation is in a reaction under conditions sufficient to permit:
(a) said Forward and Reverse Primers to mediate a polymerase chain reaction amplification of a region of the genetic variation (mutant) of SARS-COV-2 wildtype to thereby produce amplified target sequence molecules, if said mutant of SARS-COV-2 is present in said sample;
(b) said mutant probe to hybridize to said amplified target sequence molecules; and
(c) (1) said DNA polymerase has a 5'→3' exonuclease activity that hydrolyzes said hybridized mutant probe, to thereby separate said fluorophore thereof from said quencher thereof and cause a fluorescent signal to become detectable; or
(2) said hybridization of said mutant probe to said amplified target sequence molecule separates said fluorophore thereof from said quencher thereof and causes a fluorescent signal to become detectable; and
(II) determining whether said mutant of SARS-COV-2 is present in said sample by determining whether a fluorescent signal of said fluorophore has become detectable;
wherein the oligonucleotides of the mutant probe are selected from the group consisting of SEQ ID NO:6 and SEQ ID NO:24.

9. Method of claim 3 wherein said method comprises real-time PCR.

10. Method of claim 3, wherein said sample is contacted in the additional presence of:
(5) an wildtype probe, said wildtype probe being an oligonucleotide that is able to specifically hybridize to an oligonucleotide having a nucleotide sequence that comprises or consists essentially of the nucleotide sequence selected from the group consisting of SEQ ID NO:1 and SEQ ID NO: 19 and optionally SEQ ID NO: 55; and wherein said wildtype probe oligonucleotide is labeled with a fluorophore and to a quencher of fluorescence of said fluorophore; wherein the fluorescence of said fluorophore of said wildtype probe is distinguishable from the fluorescence of said fluorophore of said mutant probe;
wherein said reaction is additionally incubated under conditions sufficient to permit:
(a) said amplification primers comprising Forward and Reverse Primers to mediate a polymerase chain reaction amplification of a region of the spike gene of SARS-COV-2 wildtype as defined in one selected from the group consisting of SEQ ID NO:1 and SEQ ID NO: 19 and optionally SEQ ID NO: 55 to thereby produce amplified spike gene oligonucleotide molecules, if said SARS-COV-2 wildtype is present in said sample;
(b) said wildtype probe to hybridize to said amplified spike gene oligonucleotide molecules; and
(c) (1) said DNA polymerase has a 5'→3' exonuclease activity that hydrolyzes said hybridized wildtype probe, to thereby separate said fluorophore thereof from said quencher thereof and cause a fluorescent signal to become detectable; or
(2) said hybridization of said wildtype probe to said amplified spike gene oligonucleotide molecules separates said fluorophore thereof from said quencher thereof and causes a fluorescent signal to become detectable; and
wherein said SARS-COV-2 wildtype or said mutant of SARS-COV-2 respectively is determined to be present in said sample by determining whether a fluorescent signal of one of said wildtype probe or said mutant probe fluorophores has become detectable.

11. Method of claim 10 wherein said wildtype probe is a fragment of an oligonucleotide of SARS-COV-2 wild type said probe having a nucleotide sequence that consists of one of the nucleotide sequences selected from SEQ ID NO:5 and SEQ ID NO: 23 and optionally SEQ ID NO: 59.

12. A kit for detecting the presence of SARS-COV-2 and/or a mutant of SARS-COV-2 in a sample, wherein said kit comprises one or more of the following systems A and D and optionally system J:

System A for the detection of genetic variation A23063T of the spike gene of SARS-CoV-2 comprising:

(1) a Forward Primer (A) having a nucleotide sequence that consists essentially of the nucleotide sequence of SEQ ID NO:3;
(2) a Reverse Primer (A) having a nucleotide sequence that consists essentially of the nucleotide sequence of SEQ ID NO:4; and
(3) probe(s) comprising
i) a mutant probe (A) oligonucleotide which has a nucleotide sequence that is consisting of the nucleotide sequence of SEQ ID NO:6 and which is labeled with a fluorophore and a quencher of fluorescence of said fluorophore; and
optionally
ii) a wildtype probe (A) oligonucleotide which has a nucleotide sequence that is consisting of the nucleotide sequence of SEQ ID NO:5 and which is labeled with a fluorophore and a quencher of fluorescence of said fluorophore;
(4) optionally at least one target positive control oligonucleotide comprising SEQ ID NO: 1 and/or SEQ ID NO:2;
System D for the detection of genetic variation G22813T of the spike gene of SARS-CoV-2 comprising:
(1) a Forward Primer (D) having a nucleotide sequence that consists essentially of the nucleotide sequence of SEQ ID NO:21;
(2) a Reverse Primer (D) having a nucleotide sequence that consists essentially of the nucleotide sequence of SEQ ID NO:22; and
(3) probe(s) comprising
i) a mutant probe (D) oligonucleotide which has a nucleotide sequence that is consisting of the nucleotide sequence of SEQ ID NO:24 and which is labeled with a fluorophore and a quencher of fluorescence of said fluorophore; and
optionally
ii) a wildtype probe (D) oligonucleotide which has a nucleotide sequence that is consisting of the nucleotide sequence of SEQ ID NO:23 and which is labeled with a fluorophore and a quencher of fluorescence of said fluorophore;
(4) optionally at least one target positive control oligonucleotide comprising SEQ ID NO: 19 and/or SEQ ID NO:20;
System J for the detection of genetic variation G23012A of the spike gene of SARS-CoV-2 comprising:
(1) a Forward Primer (J) having a nucleotide sequence that consists essentially of the nucleotide sequence of SEQ ID NO:57;
(2) a Reverse Primer (J) having a nucleotide sequence that consists essentially of the nucleotide sequence of SEQ ID NO:58; and
(3) probe(s) comprising
i) a mutant probe (J) oligonucleotide which has a nucleotide sequence that is consisting of the nucleotide sequence of SEQ ID NO:60 and which is labeled with a fluorophore and a quencher of fluorescence of said fluorophore; and
optionally
ii) a wildtype probe (J) oligonucleotide which has a nucleotide sequence that is consisting of the nucleotide sequence of SEQ ID NO:59 and which is labeled with a fluorophore and a quencher of fluorescence of said fluorophore;
(4) optionally at least one target positive control oligonucleotide comprising SEQ ID NO:55 and/or SEQ ID NO:56.

13. Method for the detection and determination of SARS-COV-2 and/or a mutant of SARS-COV-2 in a sample using the kit according to claim 12, the method comprising the step of
a) separately contacting the sample with one or more of systems A and D and optionally system J of the kit according to claim 12;
b) performing a PCR with each of the contacted samples:
c) determining the presence of SARS-COV-2 and/or a mutant of SARS-COV-2 in the sample, by fluorescence analysis.

14. A method for detecting the presence of genetic variation(s) (mutant) of SARS-COV-2 wildtype in a sample, wherein said method comprises
1) contacting a sample with the following A and D and optionally J:
wherein A comprises
(1) a Forward Primer (A) having a nucleotide sequence that consists essentially of the nucleotide sequence of SEQ ID NO:3;
(2) a Reverse Primer (A) having a nucleotide sequence that consists essentially of the nucleotide sequence of SEQ ID NO:4; and
(3) a mutant probe (A) oligonucleotide which has a nucleotide sequence that is consisting of the nucleotide sequence of SEQ ID NO:6 and which is labeled with a fluorophore and a quencher of fluorescence of said fluorophore;
wherein D comprises
(1) a Forward Primer (D) having a nucleotide sequence that consists essentially of the nucleotide sequence of SEQ ID NO:21;
(2) a Reverse Primer (D) having a nucleotide sequence that consists essentially of the nucleotide sequence of SEQ ID NO:22; and
(3) a mutant probe (D) oligonucleotide which has a nucleotide sequence that is consisting of the nucleotide sequence of SEQ ID NO:24 and which is labeled with a fluorophore and a quencher of fluorescence of said fluorophore; and
wherein J comprises
(1) a Forward Primer (J) having a nucleotide sequence that consists essentially of the nucleotide sequence of SEQ ID NO:57;
(2) a Reverse Primer (J) having a nucleotide sequence that consists essentially of the nucleotide sequence of SEQ ID NO:58; and
(3) a mutant probe (J) oligonucleotide which has a nucleotide sequence that is consisting of the nucleotide sequence of SEQ ID NO:60 and which is labeled with a fluorophore and a quencher of fluorescence of said fluorophore;
2) performing a multiplex primer extension reaction; and
3) determining whether the genetic variation of the spike gene of SARS-COV-2 or a fragment thereof is present in said sample, by determining whether a fluorescent signal of said fluorophore has become detectable.

15. The oligonucleotide according to claim 2, wherein said quencher is a black hole quencher 1 (BHQ1).

16. The oligonucleotide according to claim 2, wherein said quencher is a black hole quencher 1 (BHQ1) comprising a moiety of 4'-(2-Nitro-4-toluyldiazo)-2'-methoxy-5'-methyl-azobenzene-4"-(N-ethyl)-N-ethyl.

* * * * *